US012029793B2

(12) United States Patent
Reshetnyak et al.

(10) Patent No.: US 12,029,793 B2
(45) Date of Patent: *Jul. 9, 2024

(54) pH LOW INSERTION PEPTIDE TARGETED DELIVERY OF POTENT CYTOTOXIC COMPOUNDS

(71) Applicants: University of Rhode Island Board of Trustees, Kingston, RI (US); Yale University, New Haven, CT (US)

(72) Inventors: Yana K. Reshetnyak, Saunderstown, RI (US); Oleg A. Andreev, Saunderstown, RI (US); Anna Moshnikova, Warwick, RI (US); Donald M. Engelman, New Haven, CT (US)

(73) Assignees: Yale University, New Haven, CT (US); University of Rhode Island Board of Trustees, Kingston, RI (US)

( * ) Notice: Subject to any disclaimer, the term of this patent is extended or adjusted under 35 U.S.C. 154(b) by 115 days.

This patent is subject to a terminal disclaimer.

(21) Appl. No.: 16/774,966

(22) Filed: Jan. 28, 2020

(65) Prior Publication Data

US 2020/0237926 A1    Jul. 30, 2020

Related U.S. Application Data

(60) Provisional application No. 62/797,881, filed on Jan. 28, 2019.

(51) Int. Cl.
| | |
|---|---|
| A61K 47/64 | (2017.01) |
| A61K 9/00 | (2006.01) |
| A61K 31/4745 | (2006.01) |
| A61K 31/5386 | (2006.01) |
| A61K 31/7036 | (2006.01) |
| A61K 38/12 | (2006.01) |
| A61K 47/60 | (2017.01) |
| A61P 35/00 | (2006.01) |

(52) U.S. Cl.
CPC ........ *A61K 47/6425* (2017.08); *A61K 9/0014* (2013.01); *A61K 9/0034* (2013.01); *A61K 31/4745* (2013.01); *A61K 31/5386* (2013.01); *A61K 31/7036* (2013.01); *A61K 38/12* (2013.01); *A61K 47/60* (2017.08); *A61K 47/6415* (2017.08); *A61P 35/00* (2018.01)

(58) Field of Classification Search
CPC ............ A61K 31/4745; A61K 31/5386; A61K 31/7036; A61K 38/12; A61K 47/60; A61K 47/64; A61K 47/6415; A61K 47/6425; A61K 9/0014; A61K 9/0034; A61P 35/00

See application file for complete search history.

(56) References Cited

U.S. PATENT DOCUMENTS

| | | | |
|---|---|---|---|
| 8,076,451 B2 | 12/2011 | Reshetnyak et al. | |
| 8,703,909 B2 | 4/2014 | Reshetnyak et al. | |
| 8,846,081 B2 | 9/2014 | Reshetnyak et al. | |
| 9,289,508 B2 | 3/2016 | Reshetnyak et al. | |
| 9,623,082 B2 * | 4/2017 | Copik .................... | A61P 37/02 |
| 9,676,823 B2 | 6/2017 | Reshetnyak et al. | |
| 9,814,781 B2 | 11/2017 | Reshetnyak et al. | |
| 10,512,606 B2 | 12/2019 | Reshetnyak et al. | |
| 11,229,710 B2 | 1/2022 | Reshetnyak et al. | |
| 2008/0233107 A1 | 9/2008 | Reshetnyak et al. | |
| 2012/0039990 A1 | 2/2012 | Reshetnyak et al. | |
| 2012/0142042 A1 | 6/2012 | Reshetnyak et al. | |
| 2015/0051153 A1 | 2/2015 | Reshetnyak et al. | |
| 2015/0190471 A1 * | 7/2015 | Copik .................... | A61P 37/02 |
| | | | 435/375 |
| 2015/0191508 A1 | 7/2015 | Reshetnyak et al. | |
| 2016/0082119 A1 | 3/2016 | Gonzalez et al. | |
| 2016/0256560 A1 | 9/2016 | Reshetnyak et al. | |
| 2017/0081418 A1 | 3/2017 | Kraus et al. | |
| 2017/0267727 A1 | 9/2017 | Thevenin et al. | |
| 2018/0064648 A1 | 3/2018 | Reshetnyak et al. | |
| 2018/0117183 A1 | 5/2018 | Reshetnyak et al. | |
| 2018/0221500 A1 | 8/2018 | Reshetnyak et al. | |
| 2018/0369425 A1 | 12/2018 | Reshetnyak et al. | |
| 2019/0382448 A1 * | 12/2019 | Reshetnyak ....... | A61K 49/0043 |
| 2020/0237926 A1 * | 7/2020 | Reshetnyak ....... | A61K 47/6425 |
| 2020/0246420 A1 * | 8/2020 | Reshetnyak ......... | A61K 38/195 |
| 2020/0323882 A1 * | 10/2020 | Reshetnyak ........... | A61K 45/06 |
| 2021/0283281 A1 * | 9/2021 | Lewis .................... | C07K 14/00 |

(Continued)

OTHER PUBLICATIONS

Damelin et al. Anti-EFNA4 Calicheamicin Conjugates Effectively Target Triple-Negative Breast and Ovarian TumorInitiating Cells to Result in Sustained Tumor Regressions. Clinical Cancer Research. vol. 21, No. 18, pp. 4173-4165. Sep. 15, 2015. (Year: 2015).*

Altschul et al. (1990) "Basic Local Alignment Search Tool", Journal of Molecular Biology, 215:403-410.

Altschul et al. (1997) "Gapped BLAST and PSI-Blast: a New Generation of Protein Database Search Programs", Nucleic Acids Research, 25(17):3389-3402.

Burns et al. (Apr. 6, 2015) "Inhibition of Cancer Cell Proliferation and Breast Tumor Targeting of pHLIP-Monomethyl Auristatin E Conjugates", Molecular Pharmaceutics, 12(4):1250-1258.

(Continued)

*Primary Examiner* — Marcela M Cordero Garcia
(74) *Attorney, Agent, or Firm* — Sterne, Kessler, Goldstein & Fox P.L.L.C.

(57) ABSTRACT

The invention features a composition comprising a potent cytotoxic compound and a pH low insertion peptide, where, e.g., the cytotoxic compound cannot be used alone due to a lack of targeting. The pH low insertion peptide targets cytotoxic compounds to acidic diseased tissue, translocates cytotoxic compounds across plasma membranes into the cytosols of cells in acidic diseased tissues and induces cell death predominantly in the targeted acidic diseased tissue.

69 Claims, 15 Drawing Sheets
(10 of 15 Drawing Sheet(s) Filed in Color)
Specification includes a Sequence Listing.

(56) References Cited

U.S. PATENT DOCUMENTS

2022/0088208 A1* 3/2022 Reshetnyak ............ A61K 39/39

OTHER PUBLICATIONS

Burns et al. (Feb. 6, 2017) "Therapeutic Efficacy of a Family of pHLIP-MMAF Conjugates in Cancer Cells and Mouse Models", Molecular Pharmaceutics, 14(2):415-422.
Florento et al. (Mar. 1, 2012) "Comparison of Cytotoxic Activity of Anticancer Drugs against Various Human Tumor Cell Lines Using In Vitro Cell-Based Approach", International Journal of Biomedical Science, 8(1):76-80.
Henikoff et al. (Nov. 15, 1992) "Amino Acid Substitution Matrices from Protein Blocks", Proceedings of the National Academy of Sciences of the United States of America, 89(22):10915-10919.
Kummar et al. (May 30, 2006) "Drug Development in Oncology: Classical Cytotoxics and Molecularly Targeted Agents", British Journal of Clinical Pharmacology, 62(1):15-26.
Moshnikova et al. (Feb. 19, 2013) "Anti-Proliferative Effect of pHLIP-Amanitin", Biochemistry, 52(7):1171-1178.
Needleman et al. (Mar. 28, 1970) "A General Method Applicable to the Search for Similarities in the Amino Acid Sequence of Two Proteins", Journal of Molecular Biology, 48(3):443-453.
Pearson et al. (Apr. 1988) "Improved Tools for Biological Sequence Comparison", Proceedings of the National Academy of Sciences, 85:2444-2448.
Smith et al. (Dec. 1981) "Comparison of Biosequences", Advances in Applied Mathematics, 2(4):482-489.
Wyatt et al. (Mar. 20, 2018) "Peptides of pHLIP Family for Targeted Intracellular and Extracellular Delivery of Cargo Molecules to Tumors", Proceedings of the National Academy of Sciences of the United States of America, 115(12):E2811-E2818.
Kim EG, Kim KM. Strategies and Advancement in Antibody-Drug Conjugate Optimization for Targeted Cancer Therapeutics. Biomol Ther (Seoul). Nov. 2015;23(6):493-509. doi: 10.4062/biomolther. 2015.116. Epub Nov. 1, 2015. PMID: 26535074; PMCID: PMC4624065.
Co-pending, U.S. Appl. No. 18/331,904, inventors: Reshetnyak et al., filed Jun. 8, 2023 (Not Published).

* cited by examiner

FIG. 1
FIG. 2A
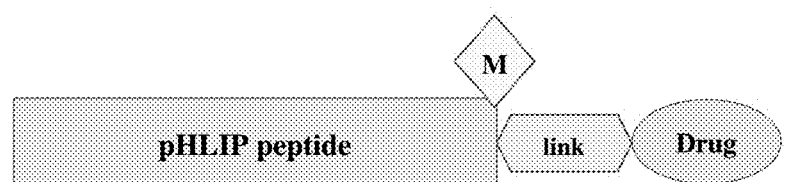
FIG. 2B
FIG. 2C
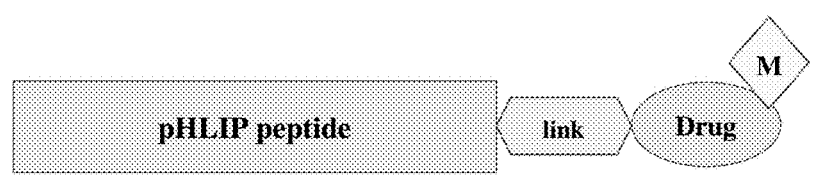
FIG. 3
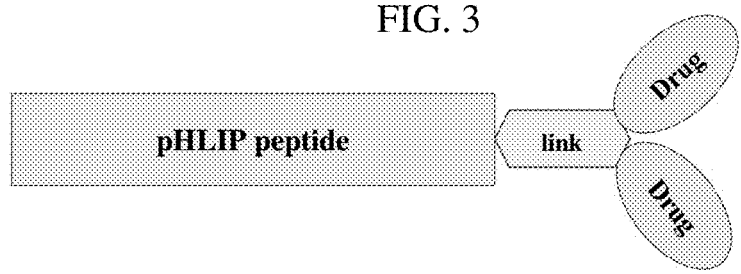

# pH LOW INSERTION PEPTIDE TARGETED DELIVERY OF POTENT CYTOTOXIC COMPOUNDS

RELATED APPLICATIONS

This application claims the benefit of priority under 35 U.S.C. § 119(e) to U.S. Provisional Application No. 62/797,881, filed Jan. 28, 2019, the entire contents of which is incorporated herein by reference in its entirety.

STATEMENT AS TO FEDERALLY SPONSORED RESEARCH

This invention was made with government support under R01 GM073857 awarded by the National Institute of General Medical Sciences of the National Institutes of Health. The government has certain rights in the invention.

INCORPORATION BY REFERENCE OF SEQUENCE LISTING

The contents of the sequence listing text file named "40984-514001WO_SL.txt", which was created on Jan. 27, 2020 and is 96,467 bytes in size, is hereby incorporated by reference in its entirety.

FIELD OF THE INVENTION

The present invention relates to chemotherapy.

BACKGROUND

Conventional methods of cancer treatment, such as non-targeted chemotherapy, are toxic and do not distinguish between normal and tumor tissues very well, and are therefore limited in their use by harmful side effects for patients. In contrast to conventional chemotherapy, targeted therapies are more efficacious and safer, and have gained increasing interest in recent years. The targeted delivery of potent cytotoxic drugs to diseased cells promises to maximize their therapeutic effects while reducing side effects. The main goal of targeted therapy is to deliver cytotoxic molecules to cells in diseased tissue while avoiding significant delivery to normal tissue.

SUMMARY OF THE INVENTION

The invention provides a solution to the problem of specific targeting of and intracellular delivery of potent cytotoxic compounds to cells in acidic diseased tissues, to induce cell death predominantly in the targeted tissue while sparing healthy cells.

Extracellular acidosis is ubiquitous in tumors, including both primary tumors and metastases, as a consequence of their rapid metabolism. Tumor cells stabilize their cytoplasmic pH by exporting the acidity to the extracellular environment. As a result of the acidic flux and the membrane potential, the extracellular pH is lowest at the surfaces of cancer cells, where it is significantly lower than either the normal physiological tissue pH or the bulk extracellular pH in tumors. The low pH region persists at the cancer cell surface even in well-perfused tumor areas. The acidity on the surfaces of cancer cells is a targetable characteristic that is not subject to clonal selection, and the level of acidity is a predictor of tumor invasion and aggression, since more rapidly growing tumor cells are more acidic. A pH Low Insertion Peptide (pHLIP©) is a water-soluble membrane peptide that interacts weakly with a cell membrane at neutral pH, without insertion into the lipid bilayer; however, at slightly acidic pH (<7.0), pHLIP© inserts into the cell membrane and forms a stable transmembrane helix. By binding a pHLIP®, or pHLIP® equivalent, to a cytotoxic compound, it is possible to specifically target and deliver the cytotoxic compound directly to the cancerous cells and into their cytosols, due to their acidic cell surfaces.

Delivering potent cytotoxic compounds using pHLIP® peptides therefore allows selective targeting of a diseased tissue (e.g. a tumor) to increase treatment efficacy. A significant advantage of this approach is that the targeted delivery of cytotoxic compounds mediated by the pHLIP© constructs described herein is associated with few side effects for the patient, which is the main problem in the use of potent cytotoxic compounds. As a result, the used of the pHLIP® constructs described herein is associated with an increase of the therapeutic index and an increase of the therapeutic window.

Accordingly, the invention features a composition comprising a potent cytotoxic compound and a pHLIP® peptide, e.g., where the cytotoxic compound comprises a small molecule that induces cell death. The cytotoxic compound is typically 2,000 Dalton in mass or less. The potent cytotoxic compound cannot be used alone, since it can induce significant toxicity in normal tissues, possibly leading to life-threatening side effects, e.g., as defined to be Adverse Events of Grade 3-5 according to the NCI guideline of Common Terminology Criteria for Adverse Events (CTCAE) v5.0, Nov. 27, 2017. Such potent cytotoxic compounds can be only used as part of targeted therapy. Examples of potent cytotoxic compounds can be selected from the classes of tubulin inhibitors, RNA polymerase inhibitors and DNA damaging agents. Examples of cytotoxic tubulin binding compounds include maytansines, chemical derivatives of maytansine (maytansinoids) and analogs of maytansine. These compounds bind to the tubulin maytansine binding site and destabilize microtubule assembly.

Cytotoxic compounds are compounds that inhibit cell growth or promote cell death when proximate to or absorbed by a cell, and moreover, when delivered to a cell (either to the interior of a target cell or to the cell surface), are capable of killing the cell or otherwise inhibiting the proliferation of the cell. Potent cytotoxic compounds are so lethal such that they cannot be administered alone. For example, in chemotherapy as a treatment of cancer often relies on the ability of cytotoxic agents to kill or damage cells which are reproducing; which preferentially targets rapidly dividing cancer cells. For example, potent cytotoxic compounds kill normal cells at a clinically unacceptable level and thus must be specifically delivered to cancer cells (or other undesirable cells), e.g., via a highly specific cancer targeting tool such as the pHLIP® peptides described herein. Thus, a significant advantage of the compositions and methods described herein is that the use of pHLIP® peptides renders previously clinically unacceptable drugs now acceptable for safe and efficacious clinical use.

Examples of cytotoxic RNA polymerase binding compounds include amatoxins, including alpha-amanitin and chemical derivatives and analogs of alpha-amanitin, which bind RNA polymerase and stop protein synthesis.

Exemplary cytotoxic DNA-damaging compounds include: i) enediyne antitumor antibiotics including calicheamicin compounds and chemical derivatives and analogs of calicheamicin, which bind in the DNA minor groove and cause strand scission; and ii) topoisomerase I inhibitor compounds, including camptothecin and its structural analog, exatecan and other chemical derivatives and analogs of exatecan, which bind and stabilize the complex of topoisomerase I and DNA, resulting in DNA damage.

The invention provides a solution to the problem, because pHLIP® peptide sequences mediate the targeting of tumor cell acidity and subsequent specific delivery of the potent cytotoxic compound into cells in a diseased tissue. The delivery is based on direct translocation of the compound across the plasma membrane (bypassing endocytotic uptake) into the cytoplasm of a targeted cell, while exhibiting little or no translocation into a normal cell. Thus, exploiting the pHLIP® peptide to allow the use of potent cytotoxic compounds as targeted highly specific chemotherapy agents.

As used herein, the term "Drug" includes a cytotoxic compound, e.g., a potent cytotoxic compound. For example, the potent cytotoxic compound cannot be used alone, since it can induce significant toxicity in normal tissues, possibly leading to life-threatening side effects, e.g., as defined to be Adverse Events of Grade 3-5 according to the NCI guideline of Common Terminology Criteria for Adverse Events (CT-CAE) v5.0, Nov. 27, 2017, hereby incorporated by reference. Other references regarding potency of cytotoxic compound and methods of evaluating potency include Kummar, S. et al. Br J Clin Pharmacol (2006) 62(1); pages 15-26 and Florento L. et al Int J Biomed Sci. (2012) 8(1); pages 76-80, incorporated herein by reference in their entireties. Such potent cytotoxic compounds can be only used as part of targeted therapy.

In some embodiments, the composition further comprises a linker between the cytotoxic compound (Drug) and the pHLIP© peptide. Exemplary linkers include a disulfide bond or an acid-labile bond. In some examples, the linker is cleavable. Exemplary cleavable linkers include those that are self-immolating. Self-immolative elimination is a spontaneous and irreversible disassembly of a multicomponent compound into its constituent fragments through a cascade of electronic elimination processes. Self-immolative elimination is driven by an increase in entropy coupled with the irreversible formation of thermodynamically stable products (e.g. $CO_2$). Such linkers have an advantage in that the cargo/therapeutic agent (drug) can be released in an unmodified form if it has an appropriate —$NH_2$ or —OH group, depicted in the schematic below:

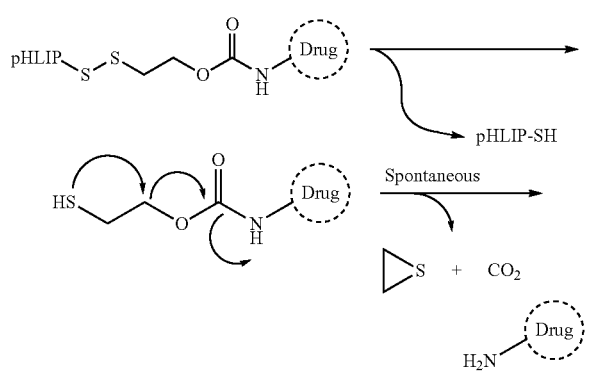

Such linkers have an advantage in that a potent cargo/therapeutic agent is released in an unmodified form. Examples also include linkers with a disulfide bond that is cleaved after delivery.

A modulator of polarity is optionally included in the composition. Such a modulator changes the overall polarity of the construct to optimize delivery to tumor cells or a tumor mass. For example, if the cargo renders the composition too polar, a modulator agent is added to make the overall composition less polar, or if the cargo is not polar enough, a modulator is added to make the composition more polar. For example, linkers comprising such modulators have an advantage in enhancing the efficiency of drug delivery into the cytosol or improving the targeting of tumors relative to normal tissues. In some examples, the construct may include a polar modulator; in other examples (such as in the case of a polar drug), the construct may include a more hydrophobic modulator to promote delivery into the cell. For example, when the cargo is polar (Log P←−0.4), the hydrophobic modulator will increase the Log P of [cargo-modulator] (Log P>−0.4). If cargo is hydrophobic Log P>2.5, the polar modulator will decrease Log P of [cargo-modulator] (Log P<2.5). Non-limiting examples of modulators are fatty acids, PEG polymers, hydrophobic fluorescent dyes, cyclic peptides.

In some examples, the composition comprises 2 or more pHLIP® peptides. Exemplary constructs comprise the following structure: Peptide-Link-B, in which Wherein "Peptide" is a first pHLIP® peptide comprising the sequence ADDQNPWRAYLDLLFPTDTLLLDLLWXA (SEQ ID NO: 1) or ADQDNPWRAYLDLLFPTDTLLLDLLWXA (SEQ ID NO: 2), "B" is a second pHLIP® peptide comprising the sequence ADDQNPWRAYLDLLFPTDTLLLD-LLWXA (SEQ ID NO: 1) or ADQDNPWRAYLDLL-FPTDTLLLDLLWXA (SEQ ID NO: 2), wherein upper case "X" indicates any amino acid residue and can include lysine (Lys), Cysteine (Cys), or an Azido-containing amino acid; and "Link" is a polyethylene glycol linker, and each "-" is a covalent bond.

Also within the invention is a method of tumor treatment comprising administering to a subject a composition comprising a potent cytotoxic compound and a pHLIP© peptide as described above. In some examples, the potent cytotoxic compound is a compound that disrupts microtubule function and induces cell death. In some examples, the potent cytotoxic compound is a compound that causes DNA strand scission and induces cell death. In some examples, the potent cytotoxic compound is a compound that binds RNA polymerase, stops protein synthesis and induces cell death. For example, the subject comprises a tumor.

The composition is administered using methods well known in the art; e.g., the composition is injected directly into a tumor mass, or administered locally by intravesical instillation, or by topical application, or the composition is systemically administered. Because of the targeting properties of the pHLIP® construct, the cytotoxic compound is specifically targeted to tumor cells and delivered into their cytoplasms.

Certain implementations comprise a formulation for a parenteral, a local, or a systemic administration comprising a pHLIP®-linker-Drug, as disclosed herein. Formulations comprising a pHLIP®-linker-Drug for intravenous, intraarterial, intraperitoneal, intracerebral, intracerebroventricular, intrathecal, intracardiac, intracavernous, intraosseous, intraocular, subcutaneous, or intravitreal administration are also provided.

In an aspect, provided herein is a formulation comprising a pHLIP®-linker-Drug for intramuscular, intradermal, transdermal, transmucosal, intralesional, subcutaneous, topical, epicutaneous, extra-amniotic, intravaginal, intravesical, nasal, or oral administration. The present subject matter also includes a formulation for intravesical instillation comprising a pHLIP®-linker-Drug as disclosed herein. In some embodiments, the formulation is used for the treatment of cancer (e.g., solid tumors) or other acidic diseased tissues.

Also provided herein is a formulation comprising a pHLIP©-linker-Drug that comprises multiple pHLIP® peptides for systemic administration. In certain embodiments, the formulation is used for the treatment of cancer or inflammation or atherosclerosis or targeting of senescent cells.

Provided herein is a method of treating cancer or inflammation or atherosclerosis or targeting of senescent cells in a subject, comprising administering to the subject an effective amount of a pH-triggered compound, wherein the compound comprises a cytotoxic compound. Non-limiting examples of cancer include bladder cancer, colon cancer, prostate cancer, breast cancer, lung cancer, skin cancer, liver cancer, bone cancer, ovarian cancer, stomach cancer, pancreatic cancer, testicular cancer, and brain cancer. In some embodiments, the cancer is bladder cancer.

Also included herein are methods for detecting and/or imaging diseased tissue (such as cancer tissue) in a subject comprising administering to the subject with a pHLIP©-Linker-Drug conjugated with imaging agent (I.A.), such as I.A.-pHLIP®-Linker-Drug.

Because of the presence of pHLIP® in the composition, the cytotoxic compound is delivered predominantly to acidic diseased tissue to induce a biological effect, cell death, predominantly in the targeted tissue. For example, the therapeutic index of the cytotoxic compound delivered in the presence of pHLIP®, e.g., in a composition that comprises both components (e.g., the pHLIP® peptide and cytotoxic compound), is at least 10%, 20%, 50%, 2-fold, 5-fold, or greater than the therapeutic index of the cytotoxic compound delivered in the absence of pHLIP® in the composition.

The composition targets the potent cytotoxic compound preferentially to a diseased tissue compared to a healthy tissue, thereby minimizing damage to the healthy tissue. In the absence of pHLIP®, the potent cytotoxic compound induces undesirable and life threatening side effects, including some or all of the following: pulmonary toxicity, neurotoxicity, ototoxicity, nephrotoxicity, hepatotoxicity, tachycardia, myelosuppression, deep vein thrombosis, oral mucositis, dysgeusia, anorexia, nausea, vomiting, diarrhea or constipation, abdominal pain, cognitive dysfunction, anxiety, depression, muscle fatigue and others. Conversely, in the presence of pHLIP®, these side effects are not observed.

Included herein are pharmaceutical compositions comprising a pH-triggered compound and a pharmaceutically acceptable carrier.

As used herein, "effective" when referring to an amount of a compound refers to the quantity of the compound that is sufficient to yield a desired response without undue adverse side effects commensurate with a reasonable benefit/risk ratio when used in the manner of this disclosure.

In some embodiments, a subject is a mammal. In certain embodiments, the mammal is a rodent (e.g., a mouse or a rat), a primate (e.g., a chimpanzee, a gorilla, a monkey, a gibbon, a baboon), a cow, a camel, a dog, a cat, a horse, a llama, a sheep, or a goat. In preferred embodiments, the subject is a human.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a diagram of a pHLIP® construct with a drug that is a cytotoxic compound.

FIGS. 2A-C are diagrams of pHLIP® constructs with a drug and a modulator (M) molecule. The modulator could be attached to pHLIP® peptide (FIG. 2A), linker (FIG. 2B) or Drug (FIG. 2C).

FIG. 3 is a diagram of a pHLIP® construct with 2 (or more) drugs. The drugs can be the same or different.

DETAILED DESCRIPTION

Figure 4A:
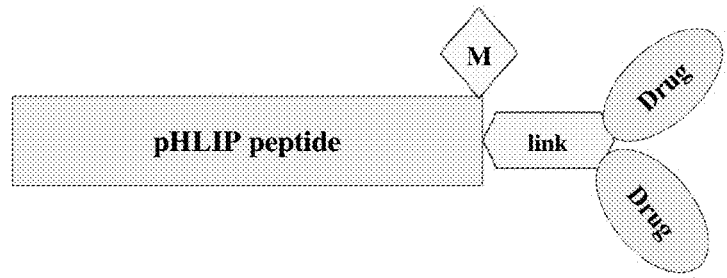
FIGS. 4A-C are diagrams of pHLIP® constructs with 2 (or more) drugs and a M molecule. The drugs can be the same or different. The modulator could be attached to pHLIP® peptide (FIG. 4A), linker (FIG. 4B) or Drug (FIG. 4C).

The invention provides compositions comprising of peptides with a higher affinity to membrane lipid bilayers at low pH than at normal pH, conjugated with cytotoxic drugs, to enable targeting of acidic tissue cells and delivery of the drugs into the cells by transmembrane insertion. Current drugs cannot distinguish very well between diseased and healthy tissue, thus affecting both, leading to life threatening side effects and a limited efficacy of treatment. Some compounds in current use, such as Doxorubicin, actually target normal tissues more than tumor tissues. In particular, potent cytotoxic compounds cannot be used alone due to their life-threatening side effects. However, such cytotoxic compounds might be used as a part of targeted therapy.

The compositions and methods are used to target tumors using pHLIP© to specifically deliver cytotoxic compounds into cells in diseased tissue (cancer) and thus to promote cell death predominantly within the targeted tissue. The invention provides 3 major features: i) targeting of cytotoxic compounds to tumors to induce cell killing predominantly within tumors; ii) sparing of normal cells in healthy organs and tissues to reduce the life threatening side effects associated with the use of the cytotoxic compounds alone; and iii) direct delivery of the cytotoxic compounds across cell membranes in diseased tissues, thus avoiding endosomal uptake, which would require endosomal escape of the cytotoxic compound for it to have its effect.

Advantages of pHLIP® Targeted Delivery of Potent Cytotoxic Compounds

Various protein biomarkers overexpressed at the surfaces of cells in diseased tissue could be targeted, thus increasing efficacy of the treatment. Although many biomarkers exist that can be exploited to improve tumor targeting and treatment outcomes, such as various receptors overexpressed at the surfaces of some cancer cells, nevertheless, useful markers are not present in all tumors. Further, the heterogeneity of the cancer cell population in an individual tumor and between tumors of various patients limits the effective use of biomarker targeting technologies. In addition, rapid mutation increases the likelihood of the selection of cancer cell phenotypes that do not express high levels of the targeted biomarker. Biomarker targeting can act as a selection method that leads to the development of drug resistance and poor patient outcomes.

Thus, a current challenge in the field of targeted chemotherapy is to search for alternative, more reliable biomarkers for tumor cell targeting. Also important are methods of intracellular delivery of potent cytotoxic drugs. If targeting could be coupled with delivery, a very important advance would be in hand. The compositions and methods described herein accomplish these objectives and thus represent significant advantages over previous approaches.

Tubulin Inhibitors

Tubulin inhibitors are drugs that interfere directly with the tubulin system. Tubulin is the major building block of microtubules, which are present in almost all eukaryotic cells, and is comprised of α-tubulin and β-tubulin subunits. Dynamic assembly and disassembly of microtubules is involved in many cellular processes such as cell structure maintenance, cell division, and intracellular transport. Disruption of microtubules induces cell cycle arrest in the G2/M phase, which makes microtubules an attractive target for drug discovery. Most tubulin inhibitors used in the clinic are natural products and their synthetic derivatives. Microtubule/tubulin inhibitors include agents promoting tubulin polymerization and stabilizing microtubule structures to block the dynamic assembly/disassembly needed for function (e.g., paclitaxel, epothilones, discodermolide and taccalonolides), and other agents inhibiting tubulin polymerization and destabilizing microtubule structures so that the microtubules cannot form (such as maytansinoids, auristatins, vinblastine and vincristine). These inhibitors are further separated into six distinct classes based on their tubulin binding sites: maytansine, vinca, taxane, colchicine, pironetin, and laulimalide/peloruside binding sites. Molecules that bind to the taxane and laulimalide/peloruside site stabilize microtubules, while compounds targeting the maytansine, colchicine, vinblastine or pironetin site destabilize microtubules.

RNA Polymerase Inhibitors

Inhibitors of RNA polymerases prevent transcription of genetic information from DNA into RNA, which stops protein synthesis, ribozyme production and the regulatory functions of RNA, leading to cell death. Some compounds (e.g., (cytarabine or cytosine arabinoside) have multiple mechanism of actions including binding to DNA and RNA polymerases and DNA. Some other compounds including rifamycins (e.g., rifampicin (or rifampin), rifabutin, rifapentine, rifalazil, and rifaximin) and amanita toxins (e.g., α-amanitin, β-amanitin, γ-amanitin, ε-amanitin, amanullin, amanullinic acid, amaninamide, amanin, and proamanullin) have a high selectivity for RNA polymerases.

DNA-Damaging Agents

The known DNA damaging agents include compounds that directly modify DNA bases, intercalate between bases, or form crosslinks in DNA. The DNA-alkylating agents including nitrogen mustards (e.g., cyclophosphamide, chlorambucil, and melphalan), nitrosoureas (e.g., carmustine, lomustine, and semustine) and triazenes (e.g., dacarbazine and temozolomide), alkylating-like platinum agents (e.g., cisplatin) and platinum-based analogs (e.g., carboplatin, and oxaliplatin) are used in the clinic. Antimetabolites including pyrimidine analogs (e.q., 5-fluorouracil, capecitabine, floxuridine, and gemcitabine) and purine analogs (e.g., 6-mercaptopurine, 8-azaguanine, fludarabine, and cladribine) mimic normal cellular molecules and interfere with DNA replication. Cytotoxic DNA-damaging antibiotics include anthracyclines (e.g., doxorubicin, daunorubicin, epirubicin, idarubicin, pirarubicin, aclarubicin, and mitoxantrone), bleomycins, mitomycins, actinomycin, and of enediyne antibiotics (e.g., calicheamicin and analogs), which either insert between base pairs on the two strands of DNA (DNA intercalation), or/and cause strand scission, or/and generate highly reactive free radicals, or/and induce DNA alkylation. Another class of DNA-damaging agents is topoisomerase I inhibitors (e.g., camptothecins and analogs), which bind topoisomerase I and stabilize the complex of topoisomerase I and DNA. As a result, DNA re-ligation is prevented, which leads to DNA damage.

Targeted Therapy and Targeted Delivery of Potent Cytotoxic Compounds

A significant proportion of cancer patients suffer from acquired resistance or relapse after long-term chemotherapy treatment. Further, non-targeted drugs have nonspecific toxicity which damages normal tissues, causing serious side effects and limiting their efficacy. In contrast to conventional chemotherapy, targeted therapy is designed to affect predominantly diseased tissue, but to spare healthy cells. The main categories of current targeted cancer therapy are small molecules (including serine/threonine kinase inhibitors and tyrosine-kinase inhibitors), monoclonal antibodies (mAbs), and antibody-drug conjugates (ADCs). In addition, various nanotechnology approaches for targeted therapy are under development.

Small-molecule or mAb targeted therapy alone often shows inadequate therapeutic activity due to its low cytotoxicity and poor penetration into solid tumors. An improved approach is to use ADCs, where a mAb is conjugated with a highly potent cytotoxic drug (or payload) through an appropriate linker. An ADC is designed as targeted therapy, which targets and kills only cancer cells while sparing healthy cells. The development of ADCs faces a number of challenges: i) the antibodies used in ADCs can elicit immunogenic responses and cause fast clearance from the circulation; ii) the cytotoxic drug can be insufficiently potent, and further conjugation might lead to decreased potency; iii) the insufficient presentation of targeted antigens at the surface of a diseased cell can lead to reduced potency or failure of an ADC; iv) poor tumor penetration of antibodies; v) the endocytotic uptake of an antibody requires endosomal escape of a drug to find its cellular target; vi) for many tumors, usable surface epitopes have not been found, and vii) tumor heterogeneity can lead to clonal selection of resistant cells, leading to a resumption of tumor growth.

Among potent cytotoxic compounds, Maytansinoids, their derivatives and analogs are exemplary of tubulin inhibitors, Amanitin, its derivatives and analogs are exemplary of RNA polymerase inhibitors, and calicheamicins and camptothecins, their derivatives and analogs are exemplary of DNA-damaging agents. Each of these and other potent cytotoxic compounds needs to be targeted to a tumor and delivered into cells—a task that is achieved by using pHLIP® technology.

pHLIP® Constructs

The invention provides compositions and methods to target tumors with pHLIP® to specifically deliver potent cytotoxic compounds to the acidic diseased tissue (such as tumors), bypass endocytotic uptake and deliver cytotoxic compounds into the cytoplasm of cells in targeted diseased tissue, and thus promote cell killing specifically within the targeted tissue only (or predominantly). As described above, a potent cytotoxic compound must be targeted to the diseased tissue otherwise side effects will preclude its clinical use.

General representations of pHLIP® compounds comprising pHLIP® peptides and cytotoxic compounds are shown in FIGS. 1-16 and described below.

FIG. 1 shows a cytotoxic compound (Drug) molecule linked to a pHLIP® peptide:

The combinations shown in FIGS. 2-12 are variations of the scheme shown in FIG. 1.

One or more modulator molecules (M) are optionally attached to the pHLIP® peptide membrane-inserting end, or linker, or Drug to potentially enhance therapeutic efficacy by reducing non-specific delivery of Drug into healthy tissue (FIG. 2). A modulator molecule(s) can be a polar molecule to prevent intracellular delivery of hydrophobic and moderately hydrophobic Drug molecules across membrane of healthy cells with normal extracellular pH.

FIG. 3 shows multiple Drug molecules linked to a single pHLIP© peptide.

Figure 4B:
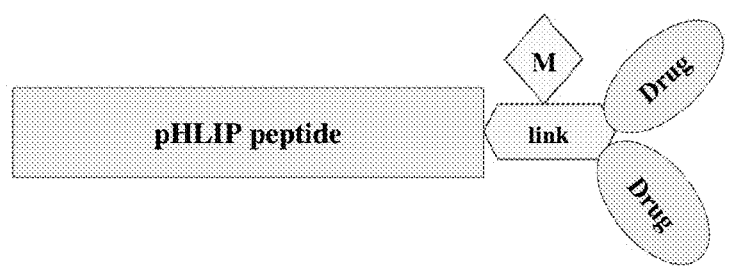
Figure 4C:
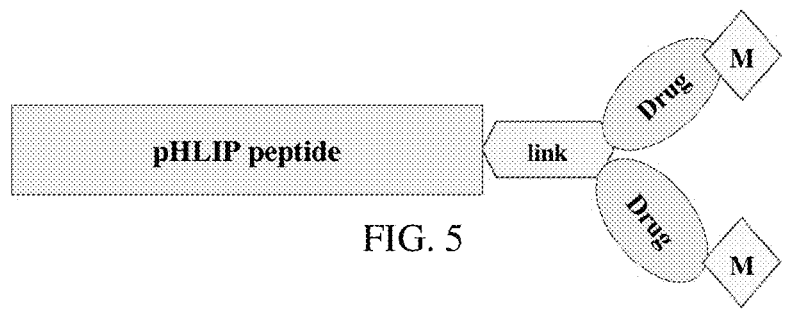
Figure 5:
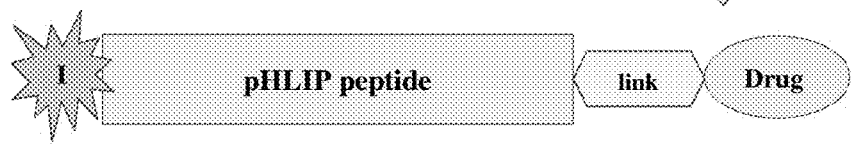
FIG. 5 is a diagram of a pHLIP® construct with a drug and an imaging agent (I) at the membrane non-inserting end.
Figure 6A:
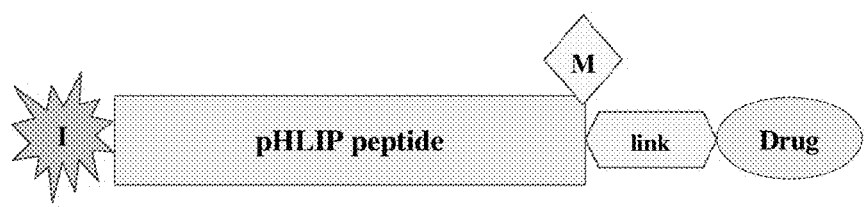
FIGS. 6A-C are diagrams of pHLIP© constructs with a drug and a M molecule and an imaging agent at the membrane non-inserting end. The modulator could be attached to pHLIP® peptide (FIG. 6A), linker (FIG. 6B) or Drug (FIG. 6C).
Figure 6B:
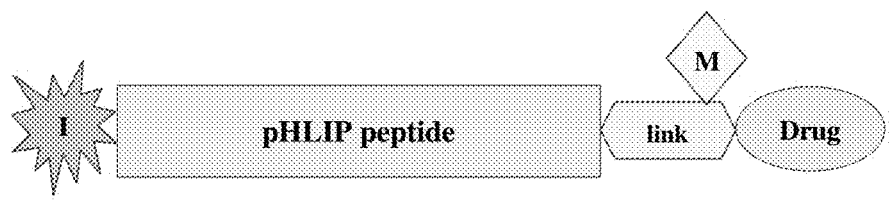
Figure 6C:
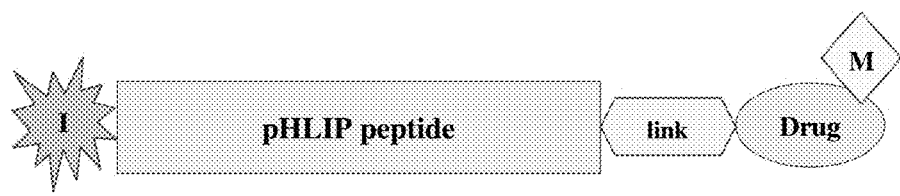
Figure 7:
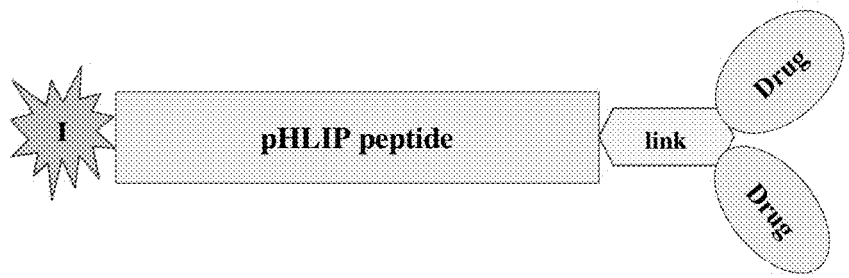
FIG. 7 is a diagram of a pHLIP© construct with multiple drugs and an imaging agent at the membrane non-inserting end. The drugs can be the same or different.
Figure 8A:
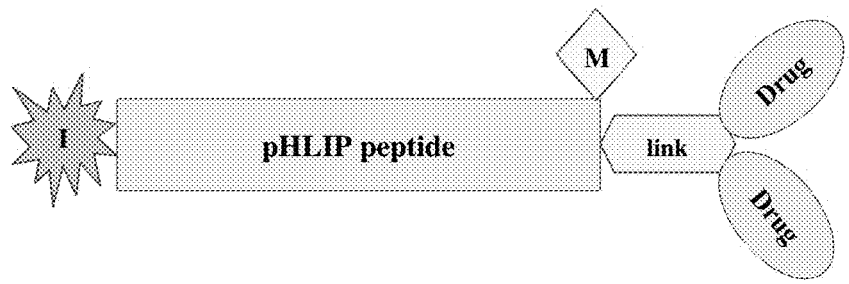
FIGS. 8A-C are diagrams of pHLIP® constructs with multiple drugs and M molecules and an imaging agent at the membrane non-inserting end. The drugs can be the same or different. The modulator could be attached to pHLIP® peptide (FIG. 8A), linker (FIG. 8B) or Drug (FIG. 8C).
Figure 8B:
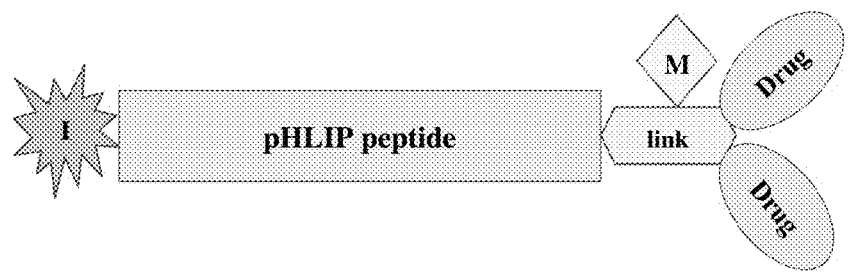
Figure 8C:
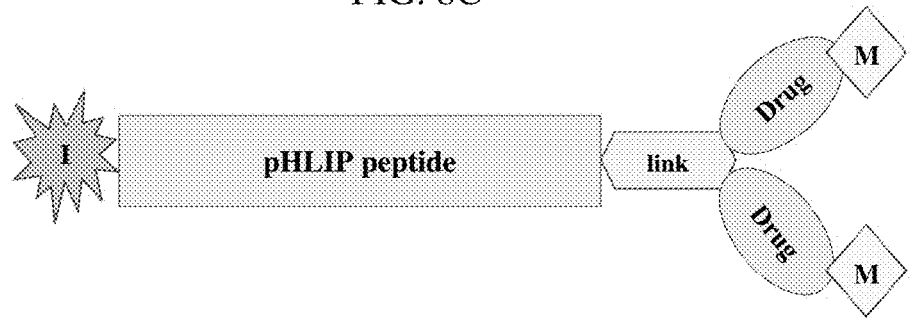

FIGS. 4A-C show multiple Drug molecules linked to a single pHLIP© peptide with one or more modulator molecules.

Figure 9:
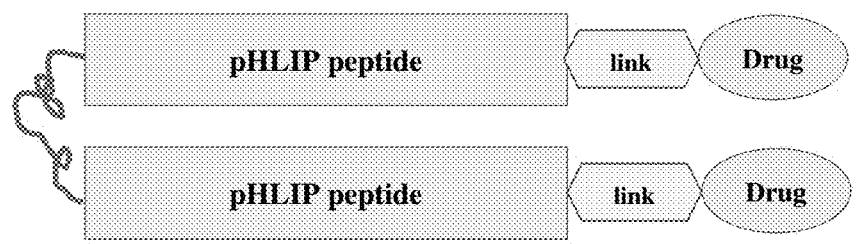
FIG. 9 is a diagram of two or more pHLIP® peptides connected to each other by PEG polymer, (or any other polymer shown by purple color) with drugs linked together via a linker molecule. The drugs can be the same or different.
Figure 10A:
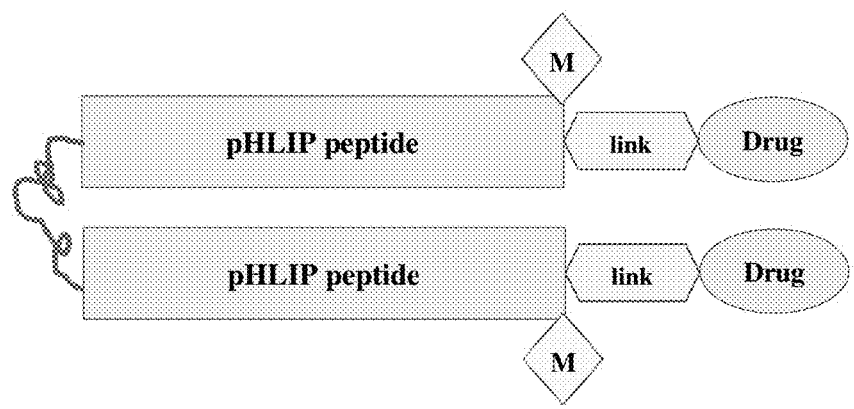
FIGS. 10A-C are diagrams of exemplary pHLIP® constructs with two or more pHLIP© peptides connected to each other by PEG polymer (or any other polymer, shown by purple color) with drugs linked together via a linker molecule. The drugs can be the same or different. The modulator could be attached to pHLIP® peptide (FIG. 10A), linker (FIG. 10B) or Drug (FIG. 10C).
Figure 10B:
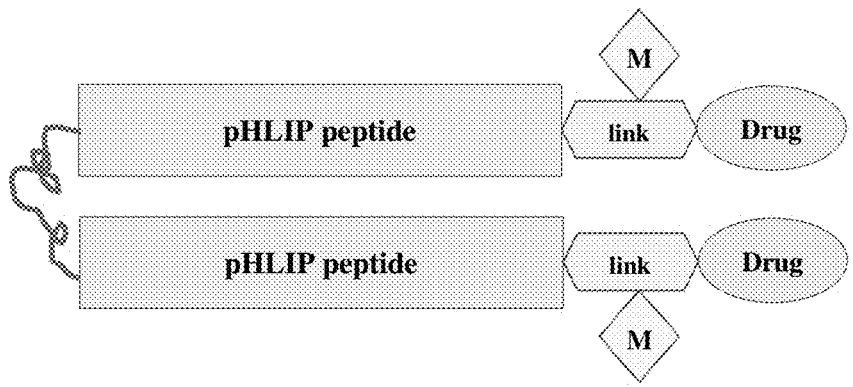
Figure 10C:
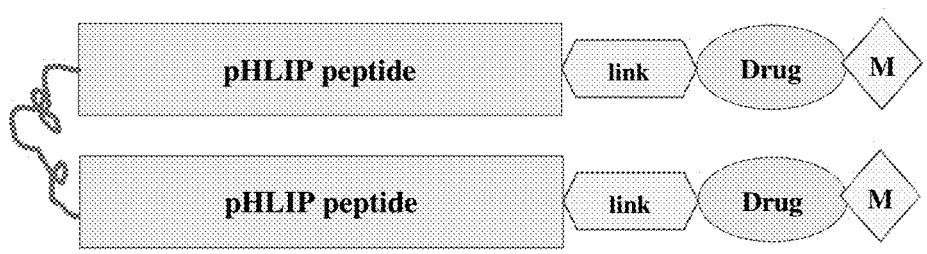
Figure 11:
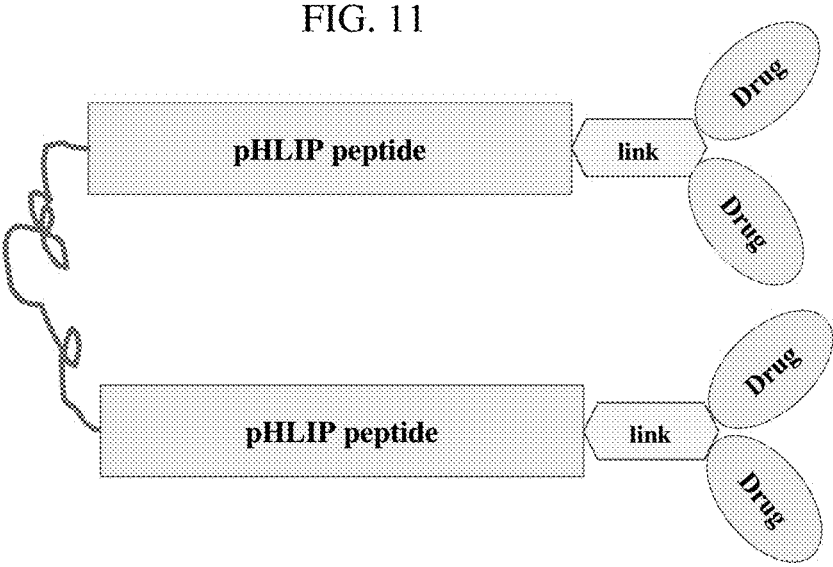
FIG. 11 is a diagram of an exemplary pHLIP® construct with two or more pHLIP® peptides connected to each other by PEG polymer (or any other polymer, shown by purple color) with drugs linked together via a linker molecule. The drugs can be the same or different.
Figure 12A:
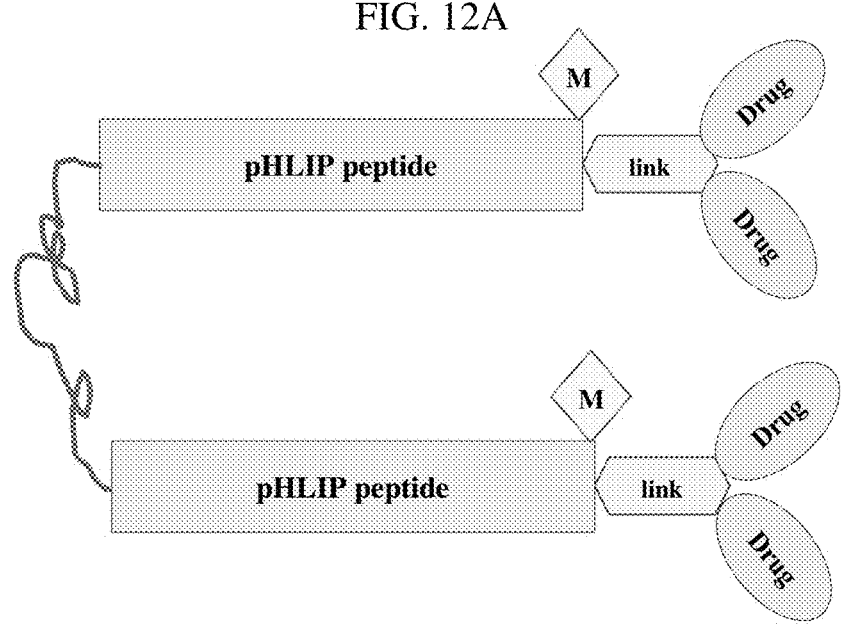
FIGS. 12A-C are diagrams of exemplary pHLIP® constructs with two or more pHLIP® peptides with drugs linked together via a linker molecule. The drugs can be the same or different. The modulator could be attached to pHLIP® peptide (FIG. 12A), linker (FIG. 12B) or Drug (FIG. 12C).
Figure 12B:
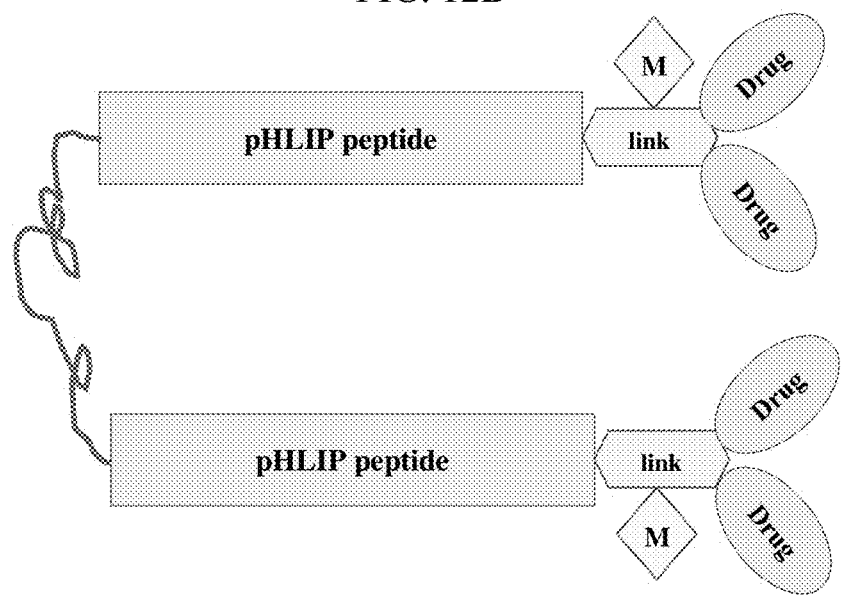
Figure 12C:
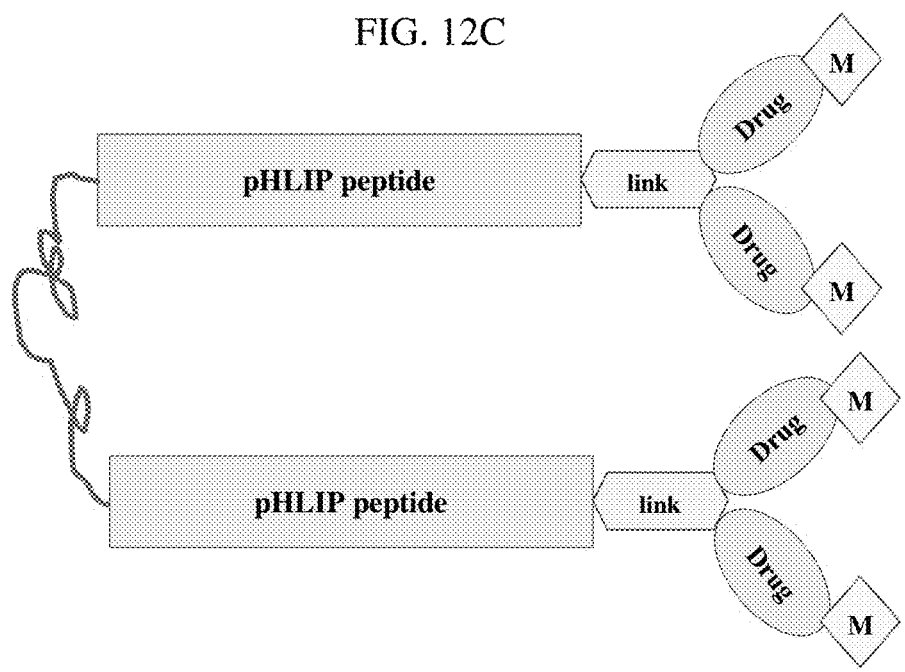

FIGS. 5, 6A-C, 7, and 8A-C depict pHLIP© compounds that can carry one or more imaging agents (I) (or other molecules) at pHLIP® peptide membrane-non-inserting end FIG. 9 shows two or more pHLIP® peptides with a Drug cargo linked together via linker molecule Exemplary constructs include a Var3 pHLIP® sequence ADDQNPWRAYLDLLFPTDTLLLDLLWCA (SEQ ID NO: 3) or ADDQNPWRAYLDLLFPTDTLLLDLLWKA (SEQ ID NO: 4) ADQDNPWRAYLDLLFPTDTLLLDLLWCA (SEQ ID NO: 5), or ADQDNPWRAYLDLLFPTDTLLLDLLWKA (SEQ ID NO: 6), or variations thereof, e.g., sequences provided in Tables below and in references cited herein (and incorporated by reference).

In one example, the Drug is a tubulin inhibitor molecule. A tubulin inhibitor molecule can target the tubulin system to promote tubulin polymerization thereby stabilizing microtubule structures or to inhibit tubulin polymerization thereby destabilizing microtubule structures. For example, a tubulin inhibitor molecule binds the tubulin maytansine site, resulting in the suppression of microtubule dynamics and causes cell cycle arrest in the G2/M phase. Non-limiting examples are maytansine, ansamitocin, maytansinol, D-alanyl maytansine, and maytansine derivatives and analogs (DM1, DM3 and DM4) bearing disulfide or thiol groups and their derivatives. Exemplary of maytansinoids is mertansine (or S-methyl-DM1, or DM1).

Alternatively, the Drug is an RNA polymerase inhibitor. An RNA polymerase inhibitor binds RNA polymerase and stops the production of functional RNA, including ribozymes, tRNA, control RNAs, and mRNA for protein synthesis. For example, an RNA polymerase inhibitor binds RNA polymerase II and III. Non-limiting examples include the *Amanita* toxins, and their derivatives and analogs. Exemplary of *Amanita* toxin is alpha-Amanitin.

In another example, the Drug is a DNA-damaging agent. DNA-damaging agents can cause strand scission or bind topoisomerase I-DNA complex. For example, a DNA-damaging agent binds DNA or topoisomerase I. Non-limiting examples are enediyne antibiotics and topoisomerase I inhibitors. Exemplary of enediyne antibiotics and topoisomerase I inhibitor are calicheamicin and camptothecins, their derivatives and analogs, respectively.

Drug(s) is linked to pHLIP© peptide(s) via cleavable link(s). For example, the cleavable link can be a disulfide bond, or acid-liable link. In other examples, the cleavable link is a self-immolating link.

Maytansinoids

The potent maytansinoid and auristatin cytotoxic tubulin inhibitors have poor therapeutic windows (low therapeutic indexes) due to a lack of tumor targeting combined with high toxicity. The low therapeutic indexes have led to failures of these potent tubulin inhibitors as chemotherapeutic anticancer agents. For example, maytansine used as anti-cancer drug exhibited significant dose-limiting toxicities including neurotoxicity, gastrointestinal toxicity, weakness, nausea, vomiting, and diarrhea. Only targeted therapy can address these limitations. Currently, maytansine- and auristatin— derivatives are validated payloads in ADCs and have been extensively investigated.

Maytansinoids are anti-mitotic tubulin inhibitors derived from maytansine, which bind to the maytansine site, resulting in the suppression of microtubule dynamics and cell cycle arrest in the G2/M phase. The maytansine site is a unique site on β-tubulin that is located at the longitudinal tubulin-tubulin interface in microtubules. Inhibitors binding this site readily destabilize microtubule assembly. Three distinctly different ligands that target the maytansine site have been introduced: maytansine, PM060184 and rhizoxin. Maytansine was one of the first potent cytotoxic compounds with picomolar $IC_{50}$ values and higher potency than taxane- and vinblastine-site inhibitors used as anti-cancer chemotherapeutic agents. Maytansine is generated from ansamitocins, which is obtained from fermenting microorganism *Actinosynnema pretiosum*. Maytansinoids, such as, maytansine analogs (DM1, DM3 and DM4), were introduced by employing of a semi-synthetic strategy. Mertansine (DM1 and, in some of its forms, emtansine) is one of the maytansine analogs.

Auristatins are derived from the natural product dolastatin-10 isolated from the sea hare *Dolabella auricularia*. Dolastatin-10 and its analogs inhibit tubulin-dependent GTP binding and block the binding of *vinca* alkaloids to tubulin in a noncompetitive manner. They are widely used as ADC payloads. Compounds of pHLIP© peptides of the WT family conjugated with monomethyl auristatin F (MMAF) and monomethyl auristatin E (MMAE) exhibit significant therapeutic efficacy in mouse models without overt toxicities [U.S. Patent Application No 20170267727; Burns K E, Hensley H, Robinson M K, Thévenin D. Therapeutic Efficacy of a Family of pHLIP-MMAF Conjugates in Cancer Cells and Mouse Models. Mol Pharm. 2017 14(2), 415-422; Burns K E, Robinson M K, Thévenin D. Inhibition of cancer cell proliferation and breast tumor targeting of pHLIP-monomethyl auristatin E conjugates. Mol Pharm. 2015 12(4), 1250-1258].

Amatoxins

Alpha-amanitin belongs to the most deadly class of all the amatoxins found in several species of the mushroom genus *Amanita* (*Amanita phalloides* and *A. virosa* and *A. bisporigera*). Alpha-amanitin is a potent inhibitor of RNA polymerase II, moderate inhibitor of RNA polymerase III and weak inhibitor of RNA polymerase IV. It blocks RNA polymerase and inhibits transcription of functional RNA, including tRNA, ribozymes, miRNA, and mRNA, and thus the subsequent synthesis of proteins, leading to cell death with 48 hours. It is a polar cyclic peptide, which cannot effectively diffuse across a plasma membrane by itself, except in liver cells, which have a special transporting system for the uptake of small cyclic molecules like phallo- and *amanita* toxins. The anti-proliferative effect of alpha-Amanitin conjugated with an anti-EpCAM antibody was tested on human cancer cell lines and assessed in vivo in immune-compromised mice bearing subcutaneous human pancreatic carcinoma xenograft tumors. The compounds of pHLIP® peptides conjugated with alpha-amanitin tested on cancer cell lines demonstrated concentration- and pH-dependent cytotoxicity [Wyatt L C, Moshnikova A, Crawford T, Engelman D M, Andreev O A, Reshetnyak Y K. Peptides of pHLIP family for targeted intracellular and extracellular delivery of cargo molecules to tumors. Proc Natl Acad Sci USA. 2018, 115 (12), E2811-E2818; Moshnikova A, Moshnikova V, Andreev O A, Reshetnyak Y K. Antiproliferative effect of pHLIP-amanitin. Biochemistry. 2013, 52 (7), 1171-1178]. Recent studies have indicated some tumors will be especially susceptible to alpha-amanitin treatment, since genomic deletion of the TP53 gene (that encodes the p53 protein) in some cancers is associated with suppression of neighboring genes, such as POLR2A gene, which encodes the catalytic subunit of RNA polymerase II. For example, POLR2A expression levels are tightly correlated with its gene copy numbers in human colorectal cancer. Thus, the use of alpha-Amanitin for potential treatment of colorectal cancer (or similar cancers with hemizygous TP53 and POLR2A deletions) is expected to be especially effective.

Calicheamicins

Calicheamicin compounds belong to the chemical group of naturally occurring enediyne antibiotics that damage DNA by double-strand cleavage. Calicheamicin was originally isolated from the bacterium *Micromonospora echinospora* and has been recognized as the most potent antitumor agent yet identified. Calicheamicin gamma is one the most active compounds used in ADCs. Calicheamicins inside a cell undergo reductive bond cleavage by glutathione, followed by spontaneous cyclization and generation of diradicals, which subsequently form abstract hydrogen atoms from DNA, resulting in a double-strand diradical. In the presence of oxygen, DNA double strands are cleaved, followed by cell death. Several ADCs employing calicheamicin as their payload are currently being tested in clinical trials.

Camptothecin Analogs

Camptothecin is a DNA topoisomerase I inhibitor isolated from the Chinese ornamental tree *Camptotheca acuminata*. Irinotecan (camptothecin-11) is a semisynthetic analog of camptothecin. Active metabolites of irinotecan known as exatecan mesylate (SN38 and DX-8951f) are used as payloads for ADCs. DX-8951f is a more water-soluble camptothecin analog, which is not an MDR1 substrate. Several ADCs employing camptothecin analogs and derivatives as their payload are currently being tested in clinical trials and obtained designation of breakthrough therapy.

pHLIP® Peptides

An example of a wild type pHLIP® peptide (WT) is AEQNPIYWARYADWLFTTPLLLLDLALLVDADEGT (SEQ ID NO: 7) in which AEQNPIY (SEQ ID NO: 8) represents a flanking sequence, WARYADWLFTTPLLLLDLALLV (SEQ ID NO: 9) represents a membrane-inserting sequence, and DADEGT (SEQ ID NO: 10) represents a flanking sequence.

Other exemplary pHLIP® peptides are shown in the Tables below.

TABLE 1

Exemplary pHLIP® peptides

| Name | Sequence | SEQ ID No. |
|---|---|---|
| Var3-1a | ADQDNPWRAYLDLLFPTDTLLLDLLWCA | SEQ. ID NO: 12 |
| Var3-1b | ADQDNPWRAYLDLLFPTDTLLLDLLWKA | SEQ. ID NO: 13 |
| WT-1 | GGEQNPIYWARYADWLFTTPLLLLDLALLVDADEGT | SEQ. ID NO. 14 |
| WT-2 | AEQNPIYWARYADWLFTTPLLLLDLALLVDADEGT | SEQ. ID NO. 15 |
| Var3-CK | ADDQNPWRAYLDLLFPTDTLLLDLLWCKA | SEQ. ID NO. 16 |
| Var3-WT-Cys | ADDQNPWRAYLDLLFPTDTLLLDLLWDADECG | SEQ. ID NO. 17 |
| Var3-WT-Lys | ADDQNPWRAYLDLLFPTDTLLLDLLWDADEKG | SEQ. ID NO. 18 |
| Var3-WT-KC | ADDQNPWRAYLDLLFPTDTLLLDLLWDADEKCG | SEQ. ID NO. 19 |
| Cys-Var3-WT | ACDDQNPWRAYLDLLFPTDTLLLDLLWDADEG | SEQ. ID NO. 20 |
| Lys-Var3-WT | AKDDQNPWRAYLDLLFPTDTLLLDLLWDADEG | SEQ. ID NO. 21 |
| WT-Cys1 | AAEQNPIYWARYADWLFTTPLLLLDLALLVDADEGTCG | SEQ. ID NO. 22 |
| WT-Cys2 | Ac-AEQNPIYWARYADWLFTTPLLLLDLALLVDADEGCT | SEQ. ID NO: 23 |
| WT-Cys3 | GGEQNPIYWARYADWLFTTPLLLLDLALLVDADEGTCG | SEQ. ID NO. 24 |
| Cys-WT1 | Ac-ACEQNPIYWARYADWLFTTPLLLLDLALLVDADEGTG | SEQ. ID NO. 25 |
| Var0-NT | ACEQNPIYWARYADWLFTTPLLLLDLALLVDADEGT | SEQ. ID NO. 26 |
| Lys-WT1 | AKEQNPIYWARYADWLFTTPLLLLDLALLVDADEGT | SEQ. ID NO. 27 |
| Lys-WT2 | Ac-AKEQNPIYWARYADWLFTTPLLLLDLALLVDADEGTG | SEQ. ID NO: 28 |
| WT-KC | AAEQNPIYWARYADWLFTTPLLLLDLALLVDADEGTKCG | SEQ. ID NO. 29 |
| K-WT-C | AKEQNPIYWARYADWLFTTPLLLLDLALLVDADECT | SEQ. ID NO. 30 |
| N-pHLIP | ACEQNPIYWARYANWLFTTPLLLLNLALLVDADEGTG | SEQ. ID NO. 31 |
| N-pHLIP-b | ACEQNPIYWARYANWLFTTPLLLLNLALLVDADEGT | SEQ. ID NO: 32 |
| K-pHLIP | ACEQNPIYWARYAKWLFTTPLLLLKLALLVDADEGTG | SEQ. ID NO. 33 |
| NNQ | GGEQNPIYWARYADWLFTTPLLLLDLALLVNANQGT | SEQ. ID NO. 34 |
| D25A | AAEQNPIYWARYADWLFTTPLLLLALALLVDADEGT | SEQ. ID NO. 35 |
| D25A-KC | Ac-AAEQNPIYWARYADWLFTTPLLLLELALLVDADEGTKCG | SEQ. ID NO: 36 |
| D14A | AAEQNPIYWARYAAWLFTTPLLLLDLALLVDADEGT | SEQ. ID NO. 37 |
| P20A | AAEQNPIYWARYADWLFTTALLLLDLALLVDADEGT | SEQ. ID NO. 38 |
| D25E | AAEQNPIYWARYADWLFTTPLLLLELALLVDADEGT | SEQ. ID NO. 39 |
| D14E | AAEQNPIYWARYAEWLFTTPLLLLDLALLVDADEGT | SEQ. ID NO. 40 |
| 3D | AAEQNPIIYWARYADWLFTDLPLLLLDLLALLVDADEGT | SEQ. ID NO. 41 |
| R11Q | GEQNPIYWAQYADWLFTTPLLLLDLALLVDADEGTCG | SEQ. ID NO. 42 |

TABLE 1-continued

Exemplary pHLIP® peptides

| Name | Sequence | SEQ ID No. |
|---|---|---|
| D25Up | GGEQNPIYWARYADWLFTTPLLLDLLALLVDADEGTCG | SEQ. ID NO. 43 |
| D25Down | GGEQNPIYWARYADWLFTTPLLLLLDALLVDADEGTCG | SEQ. ID NO. 44 |
| D14Up | GGEQNPIYWARYDAWLFTTPLLLLLDLALLVDADEGTCG | SEQ. ID NO. 45 |
| D14Down | GGEQNPIYWARYAWDLFTTPLLLLLDLALLVDADEGTCG | SEQ. ID NO. 46 |
| P20G | AAEQNPIYWARYADWLFTTGLLLLDLALLVDADEGT | SEQ. ID NO. 47 |
| H1-Cys | DDDEDNPIYWARYADWLFTTPLLLLHGALLVDADECT | SEQ. ID NO. 48 |
| H1 | DDDEDNPIYWARYADWLFTTPLLLLHGALLVDADET | SEQ. ID NO: 49 |
| H2-Cys | DDDEDNPIYWARYAHWLFTTPLLLLHGALLVDADEGCT | SEQ. ID NO. 50 |
| Cys-H2 | CDDDEDNPIYWARYAHWLFTTPLLLLHGALLVDADET | SEQ. ID NO: 51 |
| H2 | DDDEDNPIYWARYAHWLFTTPLLLLHGALLVDADEGT | SEQ. ID NO: 52 |
| H2N-Cys | DDDEDNPIYWARYAHWLFTTPLLLLHGALLVNADECT | SEQ. ID NO. 53 |
| H2N | DDDEDNPIYWARYAHWLFTTPLLLLHGALLVNADEGT | SEQ. ID NO. 54 |
| H2N2-Cys | DDDEDNPIYWARYAHWLFTTPLLLLHGALLVNANECT | SEQ. ID NO. 55 |
| H2N2 | DDDEDNPIYWARYAHWLFTTPLLLLHGALLVNANEGT | SEQ. ID NO. 56 |
| 1a-Trp | AEQNPIYWARYADFLFTTPLLLLDLALLVDADET | SEQ. ID NO. 57 |
| 1b-Trp | AEQNPIYFARYADWLFTTPLLLLDLALLVDADEGT | SEQ. ID NO. 58 |
| 1c-Trp | AEQNPIYFARYADFLFTTPLLLLDLALLWDADET | SEQ. ID NO. 59 |
| Fast-1 or Var1 | AKEDQNPYWARYADWLFTTPLLLLLDLALLVDG | SEQ. ID NO. 60 |
| Var1-2D1D | ACEDQNPYWARYADWLFTTPLLLLLDLALLVDG | SEQ. ID NO. 61 |
| Fast1-Cys or Var1-2D1D-Cys | AEDQNPYWARYADWLFTTPLLLLLDLALLVDCG | SEQ. ID NO. 62 |
| Fast1-E-Cys or Var1E | AEDQNPYWARYADWLFTTPLLLLELALLVECG | SEQ. ID NO. 63 |
| Fast1-E-Lys | AKEDQNDPYWARYADWLFTTPLLLLLDLALLVG | SEQ. ID NO: 64 |
| Fast2 or Var2 | AKEDQNPYWRAYADLFTPLTLLDLLALWDG | SEQ. ID NO: 65 |
| Fast2-E-Cys or Var2E | AEDQNPYWARYADWLFTTPLLLLELALLVCG | SEQ. ID NO: 66 |
| Var2-2D1D | ACEDQNPYWRAYADLFTPLTLLDLLALWDG | SEQ. ID NO. 67 |
| Var3-3D | ACDDQNPWRAYLDLLFPTDTLLLDLLW | SEQ. ID NO. 68 |
| Var3-3D-cys | AKDDQNPWRAYLDLLFPTDTLLLDLLWC | SEQ. ID NO. 69 |
| Var4-3E | ACEEQNPWRAYLELLFPTETLLLELLW | SEQ. ID NO: 70 |
| Var5-3Da | ACDDQNPWARYLDWLFPTDTLLLDL | SEQ. ID NO: 71 |
| Var6-3Db | CDNNNPWRAYLDLLFPTDTLLLDW | SEQ. ID NO: 72 |
| Var8-3Eb | CEEQQPWAQYLELLFPTETLLLEW | SEQ. ID NO: 73 |
| Var9-3Ec | CEEQQPWRAYLELLFPTETLLLEW | SEQ. ID NO: 74 |
| Var15-2N | CDDDDDNPNYWARYANWLFTTPLLLLLNGALLVEAEET | SEQ. ID NO: 75 |
| Var16-2P | CDDDDDNPNYWARYAPWLFTTPLLLLPGALLVEAEE | SEQ. ID NO: 76 |

TABLE 2

Exemplary pHLIP® peptides

| Name | Sequence | SEQ ID No. |
|---|---|---|
| Var14-Rev | Ac-TEDADVLLALDLLLLPTTFLWDAYRAWYPNQECA-Am | SEQ. ID NO. 77 |
| Sh | AEQNPIYWARYADWLFTTPL | SEQ. ID NO. 78 |
| Sh-Cys | AEQNPIYWARYADWLFTTPCL | SEQ. ID NO. 79 |
| Cys-Sh | ACEQNPIYWARYADWLFTTPL | SEQ. ID NO. 80 |
| Sh-1Trp | AEQNPIYFARYADWLFTTPL | SEQ. ID NO. 81 |
| Sh-W2 | AEQNPIYFARYADLLFPTTLAW | SEQ. ID NO: 82 |
| Sh-W1 | AEQNPIYWARYADLLFPTTLAF | SEQ. ID NO: 83 |
| Sh-2W | AEQNPIYWARYADLLFPTTLAW | SEQ. ID NO: 84 |
| Sh-1D | KEDQNPWARYADLLFPTTLAW | SEQ. ID NO: 85 |
| Sh-1Db | KEDQNPWARYADLLFPTTLW | SEQ. ID NO: 86 |
| Var12-1D | ACEDQNPWARYADLLFPTTLAW | SEQ. ID NO. 87 |
| Var10-2D | ACEDQNPWARYADWLFPTTLLLLD | SEQ. ID NO. 88 |
| Var13-1E | ACEEQNPWARYAELLFPTTLAW | SEQ. ID NO. 89 |
| Var11-2E | ACEEQNPWARYAEWLFPTTLLLLE | SEQ. ID NO. 90 |
| Var7-3E | ACEEQNPWARYLEWLFPTETLLLEL | SEQ. ID NO. 91 |
| Var7-3Eb | ACEEQNPQAEYAEWLFPTTLLLLE | SEQ. ID NO: 92 |

"Ac" means Acetylated N-terminus
"Am" means Amidated C-terminus

TABLE 3

Coded and exemplary non-coded amino acids including L-isomers, D-isomers, alpha-isomers, beta-isomers, glycol-, and methyl- modifications.

| No. | Abbrev | Name |
|---|---|---|
| 1 | Ala | Alanine |
| 2 | Arg | Arginine |
| 3 | Asn | Asparagine |
| 4 | Asp | Aspartic acid |
| 5 | Cys | Cysteine |
| 6 | Gln | Glutamine |
| 7 | Glu | Glutamic acid |
| 8 | Gly | Glycine |
| 9 | His | Histidine |
| 10 | Ile | Isoleucine |
| 11 | Leu | Leucine |
| 12 | Lys | Lysine |
| 13 | Met | Methionine |
| 14 | Phe | Phenylalanine |
| 15 | Pro | Proline |
| 16 | Ser | Serine |
| 17 | Thr | Threonine |
| 18 | Trp | Tryptophan |
| 19 | Tyr | Tyrosine |
| 20 | Val | Valine |
| 21 | Sec | Selenocysteine |
| 22 | Sem | Selenomethionine |
| 23 | Pyl | Pyrrolysine |
| 24 | Aad | Alpha-aminoadipic acid |
| 25 | Acpa | Amino-caprylic acid |
| 26 | Aecys | Aminoethyl cysteine |
| 27 | Afa | Aminophenyl acetate |
| 28 | Gaba | Gamma-aminobutyric acid |
| 29 | Aiba | Aminoisobutyric acid |
| 30 | Aile | Alloisoleucine |
| 31 | Alg | Allylglycine |
| 32 | Aba | Amino-butyric acid |
| 33 | Aphe | Amino-phenylalanine |
| 34 | Brphe | Bromo-phenylalanine |
| 35 | Cha | Cyclo-hexylalanine |
| 36 | Cit | Citrulline |
| 37 | Clala | Chloroalanine |
| 38 | Cie | Cycloleucine |
| 39 | Clphe | Fenclonine (or chlorophenylalanine) |
| 40 | Cya | Cysteic acid |
| 41 | Dab | Diaminobutyric acid |
| 42 | Dap | Diaminopropionic acid |
| 43 | Dap | Diaminopimelic acid |
| 44 | Dhp | Dehydro-proline |
| 45 | Dhphe | DOPA (or 3,4-dihydroxyphenylalanine) |
| 46 | Fphe | Fluorophenylalanine |
| 47 | Gaa | Glucosaminic acid |
| 48 | Gla | Gamma-carboxyglutamic acid |
| 49 | Hag | Homoarginine |
| 50 | Hlys | Hydroxylysine |
| 51 | Hnvl | Hydroxynorvaline |
| 52 | Hog | Homoglutamine |
| 53 | Hoph | Homophenylalanine |
| 54 | Has | Homoserine |
| 55 | Hse | Homocysteine |
| 56 | Hpr | Hydroxyproline |
| 57 | Iphe | Iodo-phenylalanine |
| 58 | Ise | Isoserine |
| 59 | Mle | Methyl-leucine |
| 60 | Msmet | Methionine-methylsulfonium chloride |
| 61 | Nala | Naphthyl-alanine |
| 62 | Nle | Norleucine (or 2-aminohexanoic acid) |

TABLE 3-continued

Coded and exemplary non-coded amino acids including L-isomers, D- isomers, alpha-isomers, beta-isomers, glycol-, and methyl- modifications.

| No. | Abbrev | Name |
|---|---|---|
| 63 | Nmala | N-methyl-alanine |
| 64 | Nva | Norvaline (or 2-aminopentanoic acid) |
| 65 | Obser | O-benzyl-serine |
| 66 | Obtyr | O-benzyl-tyro sine |
| 67 | Oetyr | O-ethyl-tyrosine |
| 68 | Omser | O-methyl-serine |
| 69 | Omthr | O-methy-threonine |
| 70 | Omtyr | O-methyl-tyrosine |
| 71 | Orn | Ornithine |
| 72 | Pen | Penicillamine |
| 73 | Pga | Pyroglutamic acid |
| 74 | Pip | Pipecolic acid |
| 75 | Sar | Sarcosine |
| 76 | Tfa | Trifluoro-alanine |
| 77 | Thphe | Hydroxy-Dopa |
| 78 | Vig | Vinylglycine |
| 79 | Aaspa | Amino-aminoethylsulfanylpropanoic acid |
| 80 | Ahdna | Amino-hydroxy-dioxanonanolic acid |
| 81 | Ahoha | Amino-hydroxy-oxahexanoic acid |
| 82 | Ahsopa | Amino-hydroxyethylsulfanylpropanoic acid |
| 83 | Tyr(Me) | Methoxyphenyl-methylpropanyl oxycarbonylamino propanoic acid |
| 84 | MTrp | Methyl-tryptophan |
| 85 | pTyr | Phosphorylated Tyr |
| 86 | pSer | Phosphorylated Ser |
| 87 | pThr | Phosphorylated Thr |
| 88 | BLys | BiotinLys |
| 89 | Hyp | Hydroproline |
| 90 | Phg | Phenylglycine |
| 91 | Cha | Cyclohexyl-alanine |
| 92 | Chg | Cyclohexylglycine |
| 93 | Nal | Naphthylalanine |
| 94 | Pal | Pyridyl-alanine |
| 95 | Pra | Propargylglycine |
| 96 | Gly(allyl) | Pentenoic acid |
| 97 | Pen | Penicillamine |
| 98 | MetO | Methionine sulfoxide |
| 99 | Pca | Pyroglutamic acid |
| 100 | Ac-Lys | Acetylation of Lys |

TABLE 4

Non-limiting examples of protonatable residues and their substitutions including L-isomers, D- isomers, alpha-isomers, and beta-isomers.

| Original Residue | Exemplary amino acids substitution |
|---|---|
| Asp (D) | Glu (E); Gla (Gla); Aad (Aad) |
| Glu (E) | Asp (D); Gla (Gla); Aad (Aad) |

TABLE 5

Examples of coded amino acid substitutions

| Original Residue | Substitution |
|---|---|
| Ala (A) | Gly; Ile; Leu; Met; Phe; Pro; Trp; Tyr; Val |
| Arg (R) | Lys |
| Asn (N) | Gln; His |
| Asp (D) | Glu |
| Cys (C) | Ser; Met |
| Gln (Q) | Asn; His |
| Glu (E) | Asp |
| Gly (G) | Ala; Ile; Leu; Met; Phe; Pro; Trp; Tyr; Val |
| His (H) | Asn; Gln |
| Ile (I) | Ala; Gly; Leu; Met; Phe; Pro; Trp; Tyr; Val |
| Leu (L) | Ala; Gly; Ile; Met; Phe; Pro; Trp; Tyr; Val |
| Lys (K) | Arg |
| Met (M) | Ala; Gly; Leu; Ile; Phe; Pro; Trp; Tyr; Val |
| Phe (F) | Ala; Gly; Leu; Ile; Met; Pro; Trp; Tyr; Val |
| Pro (P) | Ala; Gly; Leu; Ile; Met; Phe; Trp; Tyr; Val |
| Ser (S) | Thr |
| Thr (T) | Ser |
| Trp (W) | Ala; Gly; Leu; Ile; Met; Pro; Phe; Tyr; Val |
| Tyr (Y) | Ala; Gly; Leu; Ile; Met; Pro; Phe; Trp; Val |
| Val (V) | Ala; Gly; Leu; Ile; Met; Pro; Phe; Trp; Tyr |

TABLE 6

Non-limiting examples of membrane-inserting sequences belonging to different groups of pHLIP® peptides. Each protonatable residue (shown in bold) could be replaced by its substitution from Table 4. Each non-polar residue could be replaced by its coded amino acid substitution from Table 5, and/or non-coded amino acid substitutions from Table 3.

| Groups | Sequences | SEQ ID NO: |
|---|---|---|
| WT-BRC | WARYADWLFTTPLLLLDLALL | SEQ ID NO: 93 |
|  | YARYADWLFTTPLLLLDLALL | SEQ ID NO: 94 |
|  | WARYSDWLFTTPLLLYDLGLL | SEQ ID NO: 95 |
|  | WARYTDWFTTPLLLYDLALLA | SEQ ID NO: 96 |
|  | WARYTDWLFTTPLLLYDLGLL | SEQ ID NO: 97 |
|  | WARYADWLFTTPLLLLDLSLL | SEQ ID NO: 98 |
| WT-BRC Reverse | LLALDLLLLPTTFLWDAYRAW | SEQ ID NO: 99 |
|  | LLALDLLLLPTTFLWDAYRAY | SEQ ID NO: 100 |
|  | LLGLDYLLLPTTFLWDSYRAW | SEQ ID NO: 101 |
|  | ALLALDYLLLPTTFWDTYRAW | SEQ ID NO: 102 |
|  | LLGLDYLLLPTTFLWDTYRAW | SEQ ID NO: 103 |
|  | LLSLDLLLLPTTFLWDAYRAW | SEQ ID NO: 104 |
| ATRAM | GLAGLLGLEGLLGLPLGLLEGLWLGL | SEQ ID NO: 105 |
| ATRAM Reverse | LGLWLGELLGLPLGLLGELGLLGALG | SEQ ID NO: 106 |
| Var3 | WRAYLDLLFPTDTLLLDLLW | SEQ ID NO: 107 |
| Var3 Reverse | WLLDLLLTDTPFLLDLYARW | SEQ ID NO: 108 |

TABLE 6-continued

Non-limiting examples of membrane-inserting sequences belonging to different groups of pHLIP® peptides. Each protonatable residue (shown in bold) could be replaced by its substitution from Table 4. Each non-polar residue could be replaced by its coded amino acid substitution from Table 5, and/or non-coded amino acid substitutions from Table 3.

| Groups | Sequences | SEQ ID NO: |
| --- | --- | --- |
| Var7 | WARYLEWLFPTETLLLEL | SEQ ID NO: 109 |
|  | WAQYLELLFPTETLLLEW | SEQ ID NO: 110 |
| Var7 Reverse | LELLLTETPFLWELYRAW | SEQ ID NO: 111 |
|  | WELLLTETPFLLELYQAW | SEQ ID NO: 112 |
| Single D/E | WLFTTPLLLLNGALLVE | SEQ ID NO: 113 |
|  | WLFTTPLLLLPGALLVE | SEQ ID NO: 114 |
|  | WARYADLLFPTTLAW | SEQ ID NO: 115 |
| Single D/E Reverse | EVLLAGNLLLLPTTFLW | SEQ ID NO: 116 |
|  | EVLLAGPLLLLPTTFLW | SEQ ID NO: 117 |
|  | WALTTPFLLDAYRAW | SEQ ID NO: 118 |
| pHLIP®-Rho | NLEGFFATLGGEIALWSLVVLAIE | SEQ ID NO: 119 |
|  | EGFFATLGGEIALWSDVVLAIE | SEQ ID NO: 120 |
|  | EGFFATLGGEIPLWSDVVLAIE | SEQ ID NO: 121 |
| pHLIP®-Rho Reverse | EIALVVLSWLAIEGGLTAFFGELN | SEQ ID NO: 122 |
|  | EIALVVDSWLAIEGGLTAFFGE | SEQ ID NO: 123 |
|  | EIALVVDSWLPIEGGLTAFFGE | SEQ ID NO: 124 |
| pHLIP®-CA9 | ILDLVFGLLFAVTSVDFLVQW | SEQ ID NO: 125 |
| pHLIP®-CA9 Reverse | WQVLFDVSTVAFLLGFVLDLI | SEQ ID NO: 126 |

TABLE 7

Non-limiting examples of pHLIP® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
| --- | --- | --- |
| SEQ ID NO: 127 | WT-2D | AEQNPIYWARYADWLFTTPLLLLDLALLVDADET |
| SEQ ID NO: 128 | WT-6E | AEQNPIYWARYAEWLFTTPLLLLELALLVEAEET |
| SEQ ID NO: 129 | WT-3D | ADDQNPWRAYLDLLFPDTTDLLLLDLLWDADET |
| SEQ ID NO: 130 | WT-9E | AEEQNPWRAYLELLFPETTELLLLELLWEAEET |
| SEQ ID NO: 131 | WT-GlaD | AEQNPIYWARYA*Gla*WLFTTPLLLLDLALLVDADET |
| SEQ ID NO: 132 | WT-DGla | AEQNPIYWARYADWLFTTPLLLL*Gla*LALLVDADET |
| SEQ ID NO: 133 | WT-2Gla | AEQNPIYWARYA*Gla*WLFTTPLLLL*Gla*LALLVDADET |
| SEQ ID NO: 134 | WT-AadD | AEQNPIYWARYA*Aad*WLFTTPLLLLDLALLVDADET |
| SEQ ID NO: 135 | WT-DAad | AEQNPIYWARYADWLFTTPLLLL*Aad*LALLVDADET |
| SEQ ID NO: 136 | WT-2Aad | AEQNPIYWARYA*Aad*WLFTTPLLLL*Aad*LALLVDADET |
| SEQ ID NO: 137 | WT-GlaAad | AEQNPIYWARYA*Gla*WLFTTPLLLL*Aad*LALLVDADET |
| SEQ ID NO: 138 | WT-AadGla | AEQNPIYWARYA*Aad*WLFTTPLLLL*Gla*LALLVDADET |
| SEQ ID NO: 139 | WT-1 | GGEQNPIYWARYADWLFTTPLLLLDLALLVDADEGT |
| SEQ ID NO: 140 | WT-2 | GGEQNPIYWARYADWLFTTPLLLLLDLALLVDADEGT |
| SEQ ID NO: 141 | WT-3 | AAEQNPIYWARYADWLFTTPLLLLDLALLVDADEGT |
| SEQ ID NO: 142 | WT-4 | AEQNPIYWARYADWLFTTPLLLLDLALLVDADEGT |
| SEQ ID NO: 143 | WT-2N | AEQNPIYWARYANWLFTTPLLLLNLALLVDADEGT |

TABLE 7-continued

Non-limiting examples of pHLIP® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
|---|---|---|
| SEQ ID NO: 144 | WT-2K | AEQNPIYWARYAKWLFTTPLLLLKLALLVDADEGT |
| SEQ ID NO: 145 | WT-2DNANQ | GGEQNPIYWARYADWLFTTPLLLLDLALLVNANQGT |
| SEQ ID NO: 146 | WT-D25A | AAEQNPIYWARYADWLFTTPLLLLALALLVDADEGT |
| SEQ ID NO: 147 | WT-D14A | AAEQNPIYWARYAAWLFTTPLLLLDLALLVDADEGT |
| SEQ ID NO: 148 | WT-P20A | AAEQNPIYWARYADWLFTTALLLLDLALLVDADEGT |
| SEQ ID NO: 149 | WT-D25E | AAEQNPIYWARYADWLFTTPLLLLELALLVDADEGT |
| SEQ ID NO: 150 | WT-D14E | AAEQNPIYWARYAEWLFTTPLLLLDLALLVDADEGT |
| SEQ ID NO: 151 | WT-3D-2 | AAEQNPIIYWARYADWLFTDLPLLLLDLLALLVDADEGT |
| SEQ ID NO: 152 | WT-R11Q | GEQNPIYWAQYADWLFTTPLLLLDLALLVDADEG |
| SEQ ID NO: 153 | WT-D25Up | GGEQNPIYWARYADWLFTTPLLLDLLALLVDADEG |
| SEQ ID NO: 154 | WT-D25Down | GGEQNPIYWARYADWLFTTPLLLLLDALLVDADEG |
| SEQ ID NO: 155 | WT-D14Up | GGEQNPIYWARYDAWLFTTPLLLLLDLALLVDADEGT |
| SEQ ID NO: 156 | WT-D14Down | GGEQNPIYWARYAWDLFTTPLLLLLDLALLVDADEG |
| SEQ ID NO: 157 | WT-P20G | AAEQNPIYWARYADWLFTTGLLLLDLALLVDADEGT |
| SEQ ID NO: 158 | WT-DH | DDDEDNPIYWARYADWLFTTPLLLLHGALLVDAD |
| SEQ ID NO: 159 | WT-2H | DDDEDNPIYWARYAHWLFTTPLLLLHGALLVDADE |
| SEQ ID NO: 160 | WT-L16H | CEQNPIYWARYADWHFTTPLLLLDLALLVDADE |
| SEQ ID NO: 161 | WT-1Wa | AEQNPIYWARYADFLFTTPLLLLDLALLVDADET |
| SEQ ID NO: 162 | WT-1Wb | AEQNPIYFARYADWLFTTPLLLLDLALLVDADE |
| SEQ ID NO: 163 | WT-1Wc | AEQNPIYFARYADFLFTTPLLLLDLALLWDADET |
| SEQ ID NO: 164 | WT-W6 | ADNNPWIYARYADLTTFPLLLLDLALLVDFDD |
| SEQ ID NO: 165 | WT-W17 | ADNNPFIYARYADLTTWPLLLLDLALLVDFDD |
| SEQ ID NO: 166 | WT-W30 | ADNNPFIYARYADLTTFPLLLLDLALLVDWDD |
| SEQ ID NO: 167 | WT-W17-P7 | ADNNPFPYARYADLTTWILLLLDLALLVDFDD |
| SEQ ID NO: 168 | WT-W39-R11 | ADNNPFIAYRADLTTFPLLLLDLALLVDWDD |
| SEQ ID NO: 169 | WT-W30-R15 | ADNNPFIYATYADLRTFPLLLLDLALLVDWDD |
| SEQ ID NO: 170 | WT-Rev | Ac-TEDADVLLALDLLLLPTTFLWDAYRAWYPNQEA-Am |
| SEQ ID NO: 171 | Var1-3D | AEDQNPYWARYADWLFTTPLLLLDLALLVD |
| SEQ ID NO: 172 | Var1-1D2E | AEDQNPYWARYADWLFTTPLLLLELALLVE |
| SEQ ID NO: 173 | Var2-3D | AEDQNPYWRAYADLFTPLTLLDLLALWD |
| SEQ ID NO: 174 | Var3-3D | ADDQNPWRAYLDLLFPTDTLLLDLLW |
| SEQ ID NO: 175 | Var3-WT | ADDQNPWRAYLDLLFPTDTLLLDLLWDADE |
| SEQ ID NO: 176 | Var3-Gla2D | ADDQNPWRAYL*Gla*LLFPTDTLLLDLLW |
| SEQ ID NO: 177 | Var3-DGlaD | ADDQNPWRAYLDLLFPT*Gla*TLLLDLLW |
| SEQ ID NO: 178 | Var3-2DGla | ADDQNPWRAYLDLLFPTDTLLL*Gla*LLW |
| SEQ ID NO: 179 | Var3-2GlaD | ADDQNPWRAYL*Gla*LLFPT*Gla*TLLLDLLW |

TABLE 7-continued

Non-limiting examples of pHLIP® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
|---|---|---|
| SEQ ID NO: 180 | Var3-GlaDGla | ADDQNPWRAYL*Gla*LLFPTDTLLL*Gla*LLW |
| SEQ ID NO: 181 | Var3-D2Gla | ADDQNPWRAYLDLLFPT*Gla*TLLL*Gla*LLW |
| SEQ ID NO: 182 | Var3-3Gla | ADDQNPWRAYL*Gla*LLFPT*Gla*TLLL*Gla*LLW |
| SEQ ID NO: 183 | Var3-Aad2D | ADDQNPWRAYL*Aad*LLFPTDTLLLDLLW |
| SEQ ID NO: 184 | Var3-DAadD | ADDQNPWRAYLDLLFPT*Aad*TLLLDLLW |
| SEQ ID NO: 185 | Var3-2DAad | ADDQNPWRAYLDLLFPTDTLLL*Aad*LLW |
| SEQ ID NO: 186 | Var3-2AadD | ADDQNPWRAYL*Aad*LLFPT*Aad*TLLLDLLW |
| SEQ ID NO: 187 | Var3-AadDAad | ADDQNPWRAYL*Aad*LLFPTDTLLL*Aad*LLW |
| SEQ ID NO: 188 | Var3-D2Aad | ADDQNPWRAYLDLLFPT*Aad*TLLL*Aad*LLW |
| SEQ ID NO: 189 | Var3-3Aad | ADDQNPWRAYL*Aad*LLFPT*Aad*TLLL*Aad*LLW |
| SEQ ID NO: 190 | Var3-GlaAadD | ADDQNPWRAYL*Gla*LLFPT*Aad*TLLLDLLW |
| SEQ ID NO: 191 | Var3-GlaDAad | ADDQNPWRAYL*Gla*LLFPTDTLLL*Aad*LLW |
| SEQ ID NO: 192 | Var3-2GlaAad | ADDQNPWRAYL*Gla*LLFPT*Gla*TLLL*Aad*LLW |
| SEQ ID NO: 193 | Var3-AadGlaD | ADDQNPWRAYL*Aad*LLFPT*Gla*TLLLDLLW |
| SEQ ID NO: 194 | Var3-AadDGla | ADDQNPWRAYL*Aad*LLFPTDTLLL*Gla*LLW |
| SEQ ID NO: 195 | Var3-GlaAadGla | ADDQNPWRAYL*Gla*LLFPT*Aad*TLLL*Gla*LLW |
| SEQ ID NO: 196 | Var3-GLL | GEEQNPWLGAYLDLLFPLELLGLLELGLW |
| SEQ ID NO: 197 | Var3-M | ADDDDDDPWQAYLDLLFPTDTLLLDLLW |
| SEQ ID NO: 198 | Var4-3E | AEEQNPWRAYLELLFPTETLLLELLW |
| SEQ ID NO: 199 | Var5-3Da | ADDQNPWARYLDWLFPTDTLLLDL |
| SEQ ID NO: 200 | Var6-3Db | DNNNPWRAYLDLLFPTDTLLLDW |
| SEQ ID NO: 201 | Var7-3E | AEEQNPWARYLEWLFPTETLLLEL |
| SEQ ID NO: 202 | Var7-M | DDDDDDPWQAYLDLFPTDTLALDLW |
| SEQ ID NO: 203 | Var8-3E | EEQQPWAQYLELLFPTETLLLEW |
| SEQ ID NO: 204 | Var9-3E | EEQQPWRAYLELLFPTETLLLEW |
| SEQ ID NO: 205 | Var10-2D | AEDQNPWARYADWLFPTTLLLLD |
| SEQ ID NO: 206 | Var11-2E | AEEQNPWARYAEWLFPTTLLLLE |
| SEQ ID NO: 207 | Var12-1D | AEDQNPWARYADLLFPTTLAW |
| SEQ ID NO: 208 | Var13-1E | AEEQNPWARYAELLFPTTLAW |
| SEQ ID NO: 209 | Var15-2N | DDDDDNPNYWARYANWLFTTPLLLLNGALLVEAEET |
| SEQ ID NO: 210 | Var16-2P | DDDDDNPNYWARYAPWLFTTPLLLLPGALLVEAEET |
| SEQ ID NO: 211 | Var17 | AEQNPIYFARYADFLFTTPLLLLDLALLWDADET |
| SEQ ID NO: 212 | Var18 | AEQNPIYWARYADFLFTTPLLLLDLALLVDADET |
| SEQ ID NO: 213 | Var19a | AEQNPIYWARYADWLFTTPL |
| SEQ ID NO: 214 | Var20 | AEQNPIYFARYADLLFPTTLAW |
| SEQ ID NO: 215 | Var21 | AEQNPIYWARYADLLFPTTLAF |
| SEQ ID NO: 216 | Var22 | AEQNPIYWARYADLLFPTTLAW |

TABLE 7-continued

Non-limiting examples of pHLIP® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
|---|---|---|
| SEQ ID NO: 217 | Var23 | AEQNPIYFARYADWLFTTPL |
| SEQ ID NO: 218 | Var24 | EDQNPWARYADLLFPTTLAW |
| SEQ ID NO: 219 | ATRAM | GLAGLAGLLGLEGLLGLPLGLLEGLWLGLELEGN |
| SEQ ID NO: 220 | pHLIP-CA9 | EQNPIYILDLVFGLLFAVTSVDFLVQWDDAGD |
| SEQ ID NO: 221 | pHLIP-Rho | NLEGFFATLGGEIALWSLVVLAIE |
| SEQ ID NO: 222 | pHLIP-RhoM1 | NNEGFFATLGGEIALWSDVVLAIE |
| SEQ ID NO: 223 | pHLIP-RhoM2 | DNNEGFFATLGGEIPLWSDVVLAIE |

Methods for Treating Cancer, Inflammation, Atherosclerosis, or Targeting Senescent Cells in a Subject Included herein is a method of preventing or treating cancer, inflammation, atherosclerosis, or targeting senescent cells in a subject (e.g., killing cells in acidic diseased tissue) in a subject in need thereof. In further embodiments, the method comprises administering to the subject an effective amount of a composition comprising a pHLIP® peptide and a cytotoxic compound (e.g., a cytotoxic tubulin inhibitor, a cytotoxic RNA polymerase inhibitor, a cytotoxic DNA damaging compound, or a toposisomerase I inhibitor).

For example, methods for preventing or treating cancer, inflammation, atherosclerosis, or targeting senescent cells in a subject (e.g., killing cells in acidic diseased tissue) include administering a composition comprising an effective amount of a composition comprising a pHLIP® peptide and a cytotoxic compound.

In other embodiments, the methods for treating cancer, inflammation, atherosclerosis, or targeting senescent cells in a subject comprises administering to a subject a composition comprising a pHLIP® peptide and a cytotoxic compound produced according to the methods described herein, optionally in combination with other treatment methods. In particular, the combination treatment can include administering readily known treatments. For example, combination therapy may include hormonal, radiation and/or immunotherapy treatment in combination with administration of pHLIP-cytotoxic molecule.

Combination therapy may also include administration of corticosteroids or pHLIP linked to corticosteroid together with administration of pHLIP-cytotoxic molecule.

The described composition can be administered as a pharmaceutically or physiologically acceptable preparation or composition containing a physiologically acceptable carrier, excipient, or diluent, and administered to the tissues of the recipient organism of interest, including humans and non-human animals.

The composition comprising a pHLIP® peptide and a cytotoxic compound can be prepared by re-suspending in a suitable liquid or solution such as sterile physiological saline or other physiologically acceptable injectable aqueous liquids. The amounts of the components to be used in such compositions can be routinely determined by those having skill in the art.

In embodiments, a therapeutically effective amount of the composition (e.g., a composition comprising a pHLIP® peptide and a cytotoxic compound) in humans can be any therapeutically effective amount. In one embodiment, the composition (e.g., a composition comprising a pHLIP© peptide and a cytotoxic compound) is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

In an embodiment, the composition (e.g., a composition comprising a pHLIP® peptide and a cytotoxic compound) is administered once a week, or once every two weeks, or once every 3 weeks or once every 4 weeks for at least 1 week, in some embodiments for 1 to 4 weeks, from 2 to 6 weeks, from 2 to 8 weeks, from 2 to 10 weeks, or from 2 to 12 weeks, 2 to 16 weeks, or longer (e.g., 1, 2, 3, 4, 5, 6, 7, 8, 9, 10, 11, 12, 36, 48, or more weeks).

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1 pHLIP® peptides are described here and in U.S. Pat. Nos. 9,814,781 and 9,289,508 (hereby incorporated by reference) as well as U.S. Patent Publication 20180117183, 20180064648, 20180221500, 20180117183, 20180064648, 20160256560, 20150191508, 20150051153, and 20120142042, 20120039990, and 20080233107, each of which is hereby incorporated by reference.

Figure 13:
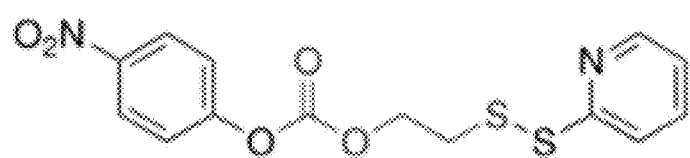
FIG. 13 is a structure of an exemplary heterobifunctional self-immolating linker useful to make pHLIP® constructs containing a drug (a therapeutic cargo).
Figure 14A:
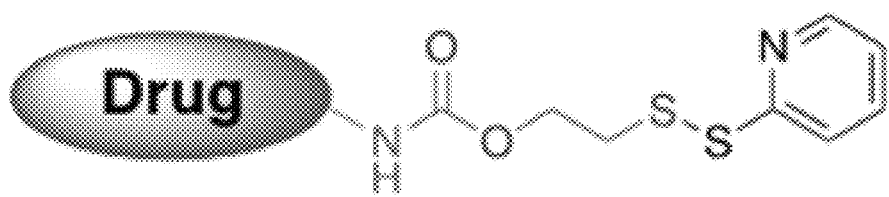
FIG. 14A is a structure of an exemplary self-immolating linker with Drug for S—S bond exchange with Cys residue of pHLIP® peptide.

Examples of potent cytotoxic compounds include: Maytansinoids, their derivatives and analogs, which are exemplary of tubulin inhibitors; alpha-amanitin, its derivatives and analogs, which are exemplary of RNA polymerase inhibitors; calicheamicins, their derivatives and analogs, which are exemplary of DNA-damaging agents; and camptothecins, their derivatives and analogs, which are exemplary of DNA-damaging topoisomerase I inhibitors. The use of these potent cytotoxic compounds has been hampered by delivery issues. FIGS. 13-14A-B show exemplary pHLIP©-linker-Drug constructs. As described above, it has not been possible to achieve an acceptable therapeutic window in the use of maytansinoids, alpha-amanitin, calicheamicins, camptothecins, and their derivates and analogs as anticancer agents alone, so targeted delivery is required. Constructs described here, e.g., a pHLIP®-linker-Drug construct, mediate targeting of maytansinoids, alpha-amanitin, calicheamicins, camptothecins, and their derivates and analogs to tumor cells (due to their surface low pH) and reduce delivery of these potent cytotoxic compounds to normal cells (with normal extracellular pH), thus avoiding or minimizing side effects, increasing the therapeutic window and enhancing the therapeutic index. The problem of targeting a potent cytotoxic compound, which is in this case maytansinoids, or alpha-amanitin, calicheamicins, or camptothecins, or the derivates and analogs of these compounds, is solved by the pHLIP®/drug compositions of the invention.

A linker could be relatively small, e.g., only a few atoms, or rather large (4-5 kDa). FIG. 13A show an exemplary heterobifunctional linker that reacts on one end with a free thiol to spontaneously form a disulfide bond, with thiopyridine as a leaving group, and on the other end reacts with activated with amine or hydroxyl groups in the presence of DIPEA, and in some cases DMAP or other activator base, to form a carbamate or carbonate, respectively.

Figure 14B:
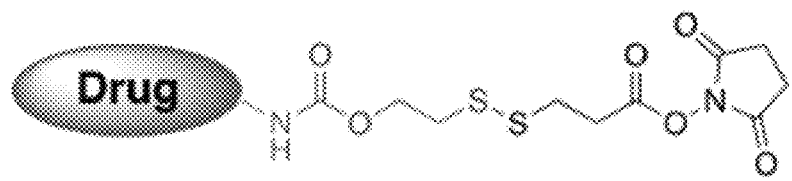
FIG. 14B is a structure of an exemplary self-immolating linker with Drug for conjugation with Lys residue at pHLIP® peptide.
Figure 15:
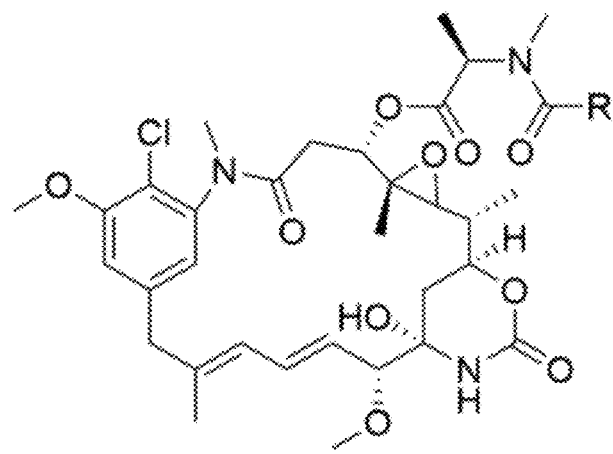
FIG. 15 is a chemical structure of maytansinoid, mertansine (DM1; CAS No.: 139504-50-0), where R=$CH_2CH_2SH$.
Figure 16:
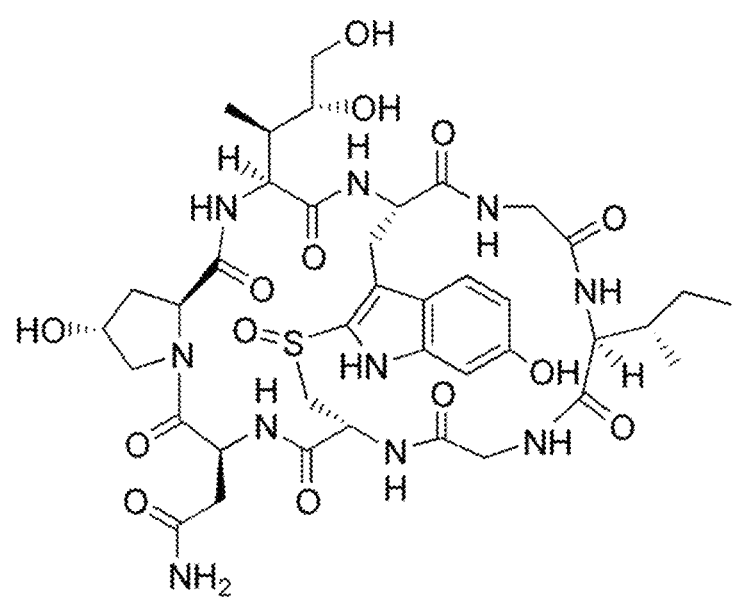
FIG. 16 is the chemical structure of alpha-amanitin.
Figure 17:
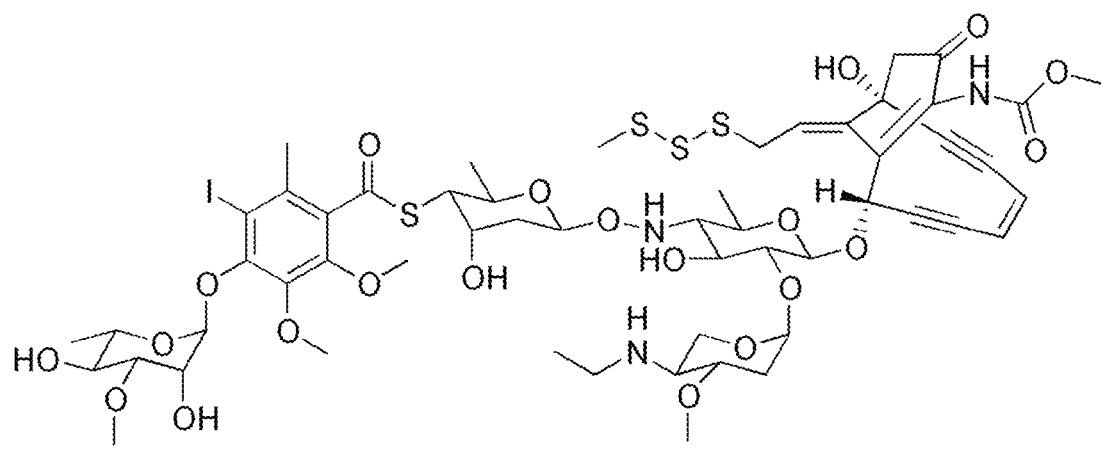
FIG. 17 is the chemical structure of the enediyne antibiotic, calicheamicin.
Figure 18:
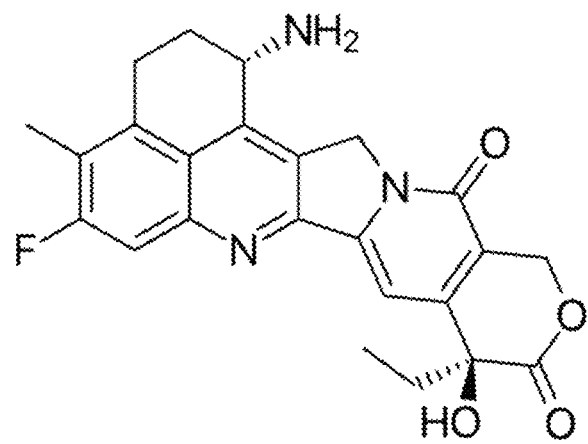
FIG. 18 is the chemical structure of a camptothecin chemical analog, exatecan (DX-8951f).

FIG. 14A is a linker-drug conjugate that reacts with a free thiol at pHLIP© peptide bearing a cysteine residue to spontaneously form a disulfide bond, with thiopyridine as a leaving group. FIG. 14B is a linker-drug conjugate that reacts with a free amino group at pHLIP® bearing a lysine residue, if pHLIP® is protected at its amino terminus, such as with N-acetylation.

In some examples, the following cross-linkers can be used: SPDP (succinimidyl 3-(2-pyridyldithio)propionate); LC-SPDP (succinimidyl 6-(3(2-pyridyldithio)propionamido)hexanoate); sulfo-LC-SPDP (sulfosuccinimidyl 6-(3'-(2-pyridyldithio)propionamido)hexanoate); PEG4-SPDP (PEGylated, long-chain SPDP crosslinker); PEG12-SPDP (PEGylated, long-chain SPDP crosslinker); SMCC (succinimidyl 4-(N-maleimidomethyl)cyclohexane-1-carboxylate); sulfo-SMCC (sulfosuccinimidyl 4-(N-maleimidomethyl)cyclohexane-1-carboxylate); SMPT (4-succinimidyloxycarbonyl-alpha-methyl-α(2-pyridyldithio)toluene); DTME (dithiobismaleimidoethane). The invention may encompass the following embodiments.

A compound having the formula:

Peptide-Mod-Linker-Drug (1), wherein:
Peptide is a pHLIP©,
Mod is a modulator, and is optional. Mod comprises a chemical entity to modulate the overall polarity of a Linker-Drug for optimized targeting by pHLIP®. To achieve optimized targeting the overall polarity of Mod-Linker-Drug can be guided by Log P, where P is the measured octanol-water partition coefficient, is preferably in the range $-1<\text{Log P}<1$. Optionally, the Mod can be attached to the inserting end of pHLIP®, the linker, or the drug.

In some cases, a potent cytotoxic compound or drug is polar or moderately hydrophobic. The average value of the measured Log P for drugs is about 2-3. Exemplary drugs are polar, moderately hydrophobic or hydrophobic as defined by the following characteristics. Polar: Log $P<-0.4$; Moderately hydrophobic: $2.5<\text{Log P}<-0.4$; and Hydrophobic: Log $P>2.5$. The polarity and/or hydrophobicity of a drug or compound to be delivered is measured using methods known in the art, e.g., by determining Log P, in which P is the octanol-water partition coefficient. A substance is dissolved into an octanol-water mixture, mixed, and allowed to come to equilibration. The amount of substance in each (or one) phases is then measured. The measurements itself could be in a number of ways known in the art, e.g., by measuring absorbance, or determining the amount using NMR, HPLC, or other known methods. If the cargo is polar (Log $P<-0.4$), the hydrophobic modulator will increase the Log P of (the cargo-modulator) (Log $P>-0.4$). If cargo is hydrophobic Log $P>2.5$, the polar modulator will decrease Log P of [cargo-modulator] (Log $P<2.5$).

Linker comprises a covalent bond or a chemical linker such that (1) is selected from the following:

(2)

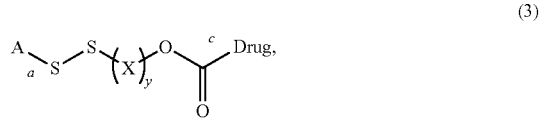
(3)

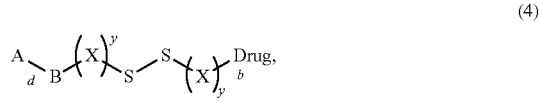
(4)

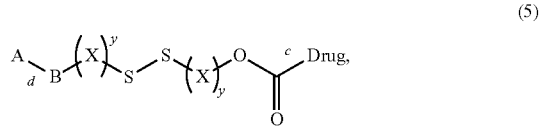
(5)

each occurrence of y may be present or absent and is independently an integer ranging from 1 to 4;
each occurrence of X is independently selected from the group consisting of $CH_2$, CH(alkyl), and C(alkyl)$_2$;
each occurrence of B may be present or absent and is independently selected from the group consisting of alkyl, aryl, and PEG;
bond a is formed between the sulfur and the thiol substituent of a cysteine residue in A;
bond b is formed between the carbon and a substituent on the Drug, wherein the substituent is selected from the group consisting of hydroxyl, carbonyl, amine, amide, sulfate, sulfonamide, phosphate, and phosphoramide;
bond c is formed between the carbonyl and a substituent on Drug, wherein the substituent is selected from the group consisting of primary amine, secondary amine, and hydroxyl;
bond d is formed between B and an amino acid residue in A, wherein the amino acid is selected from the group consisting of serine, threonine, tyrosine, tryptophan, histidine, lysine, and cysteine and comprises an amide, ester, carbamate, carbonate, or maleimide bond.

Drug comprises or consists of a potent cytotoxic drug or compound with anticancer activity. The potent cytotoxic compound (or a high-potency active pharmaceutical ingredient, HPAPI) is defined as an agent with an occupational exposure limit (OEL) at or below 10 μg/m$^3$ of air as an 8-h time-weighted average and a pharmacologically active ingredient or intermediate with high selectivity and/or with the potential to cause cancer, mutations, developmental effects, or reproductive toxicity at low doses.

Exemplary drugs are described below. The Drug is a tubulin inhibitor, which binds one of the following tubulin binding sites: maytansine, vinca, taxane, colchicine, pironetin, and laulimalide/peloruside. The composition of formula (1) may include a Drug that is a tubulin inhibitor. Alternatively, the Drug is selected from the group consisting of tubulin inhibitors and their derivatives including microtubule destabilizers: maytansine and its derivatives, dolastatin-10 and its derivatives, cryptopycin-1, cryptopycin-52, tubulysins D, hemiasterlin and its derivative (HTI-286), colchicine and CA4, and microtubule stabilizers: paclitaxel, discodermolide, taccalonolides A and B and their derivatives (taccalonolide AF and taccalonolide AJ), and taccalonolide AI-epoxide, laulimalide, and epothilones A and B:

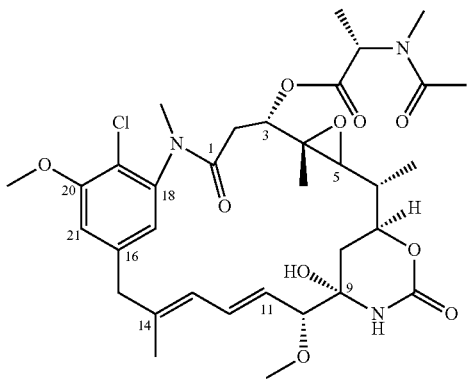

Maytansine (1)

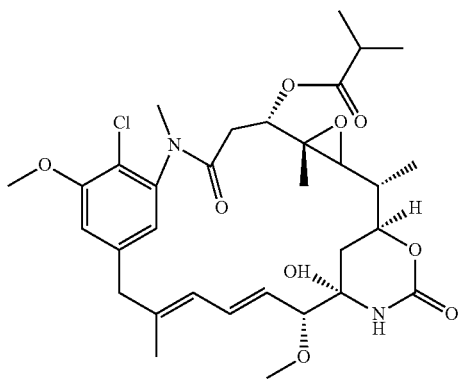

Ansamitocin P-3 (2)

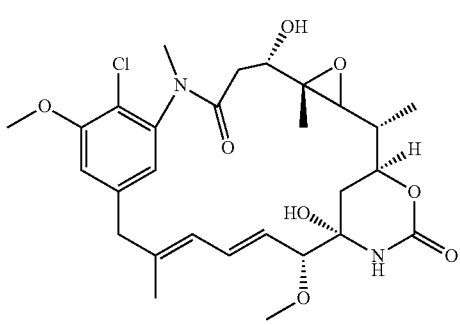

Maytansinol (3)

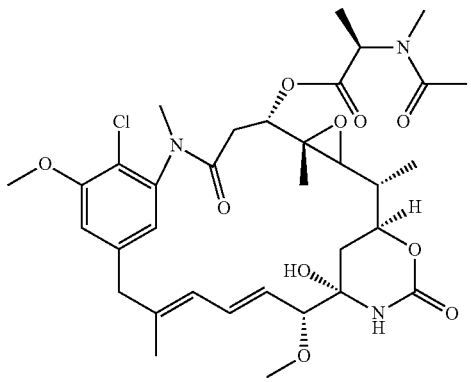

D-Alanyl maytansine (4)

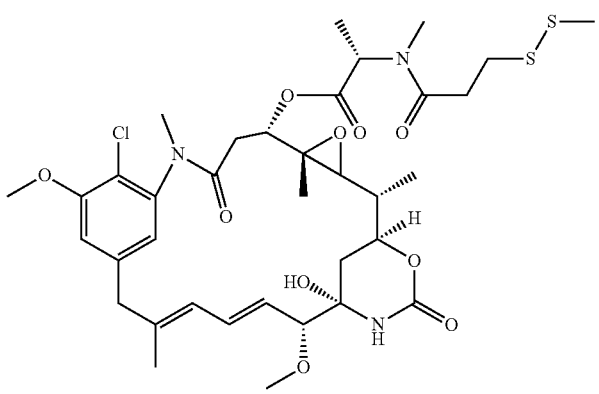

S-methyl-DM1 (5)

-continued
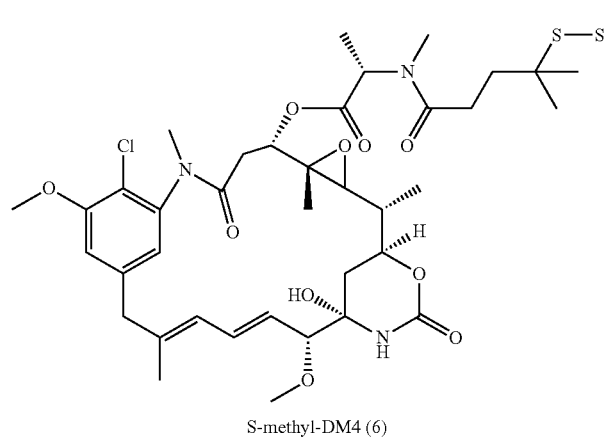
S-methyl-DM4 (6)
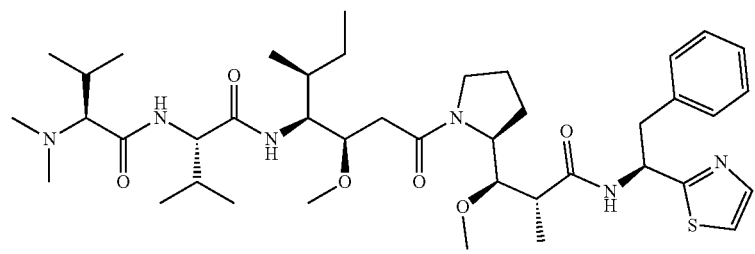
Dolastatin-10 (7)
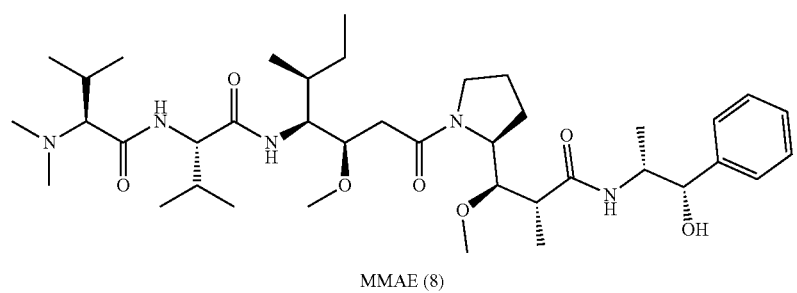
MMAE (8)
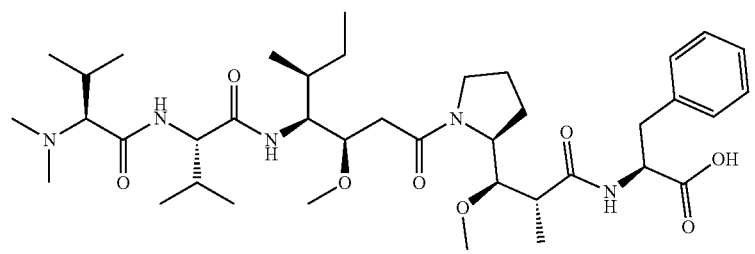
MMAF (9)

-continued
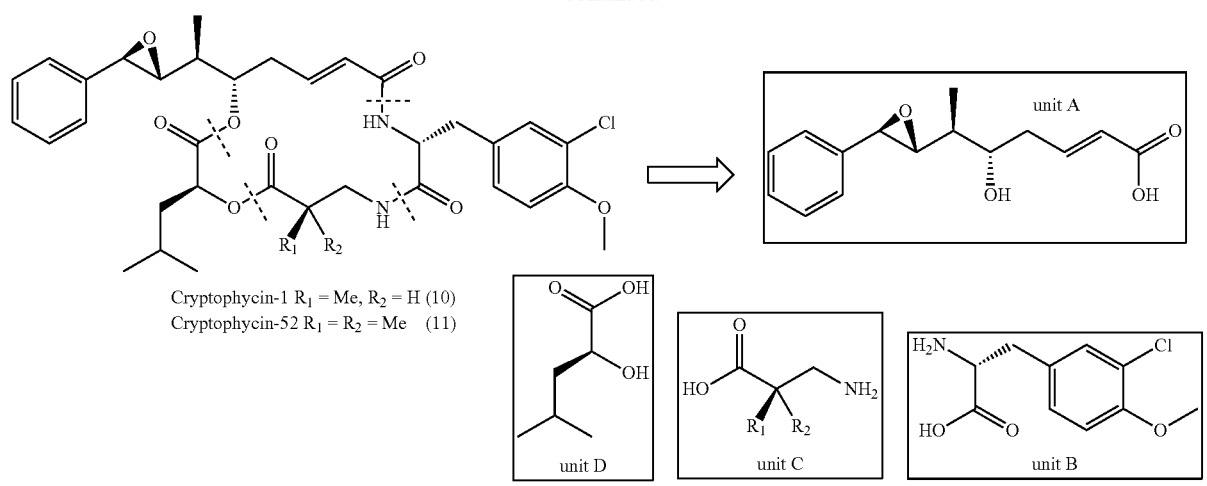
Cryptophycin-1 R₁ = Me, R₂ = H (10)
Cryptophycin-52 R₁ = R₂ = Me (11)
unit A
unit D
unit C
unit B
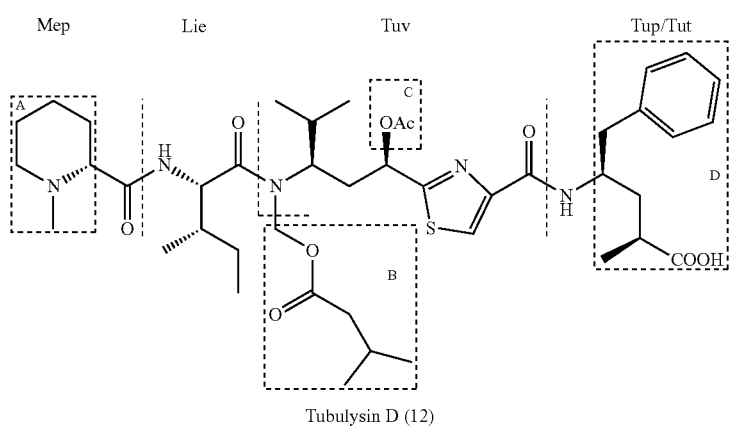
Mep    Lie    Tuv    Tup/Tut
Tubulysin D (12)
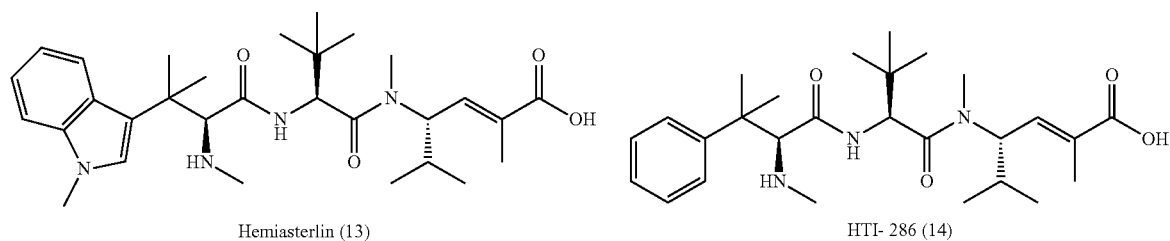
Hemiasterlin (13)                    HTI-286 (14)
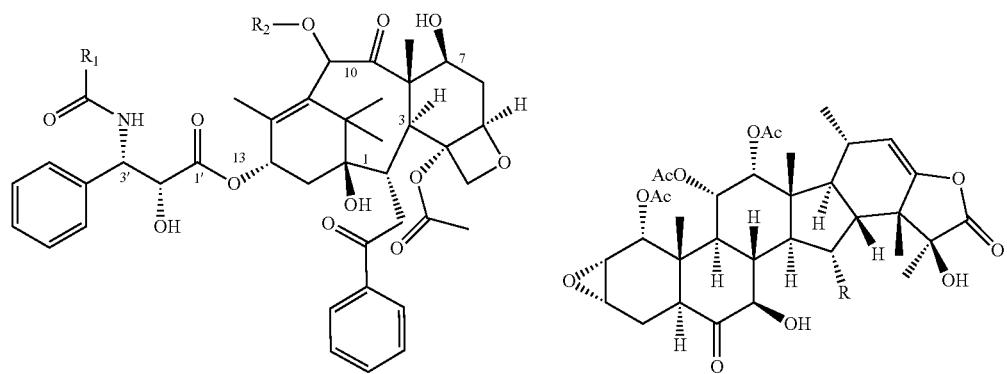
Paclitaxel R1 = Ph, R2 = Ac (15)
Docetaxel R1 = t-BuO, R2 = H (16)
Taccalonolide A: R = OAc (17)
Taccalonolide B: R = OH (18)

-continued
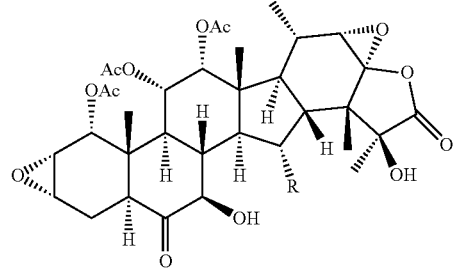
Taccalonolides AF: R = OAc (19)
Taccalonolides AJ: R = OH (20)
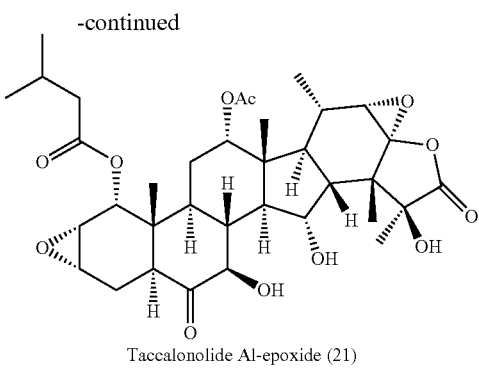
Taccalonolide AI-epoxide (21)
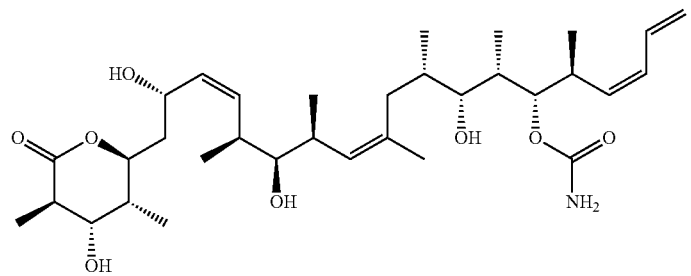
Discodermolide (22)
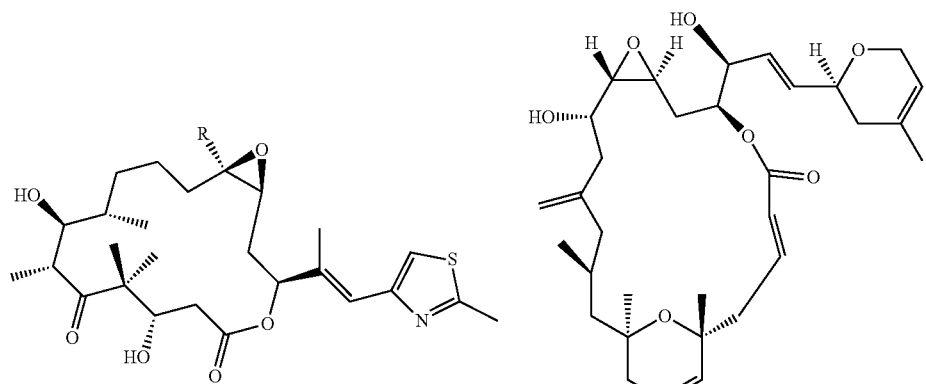
Epothilone A: R = H (23)
Epothilone B: R = Me (24)
Laulimalide (25)
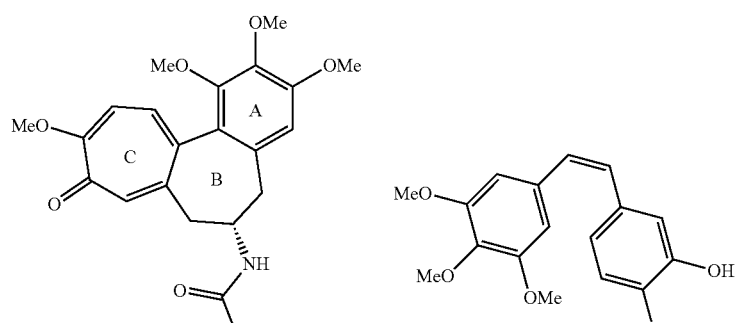
Colchicine (26)
CA-4 (27)

A compound of formula (1), wherein Drug is a maytansinoid, a tubulin inhibitor, which binds maytansine tubulin binding site.

A compound of formula (1), wherein Drug is selected from the group consisting of maytansinoids:

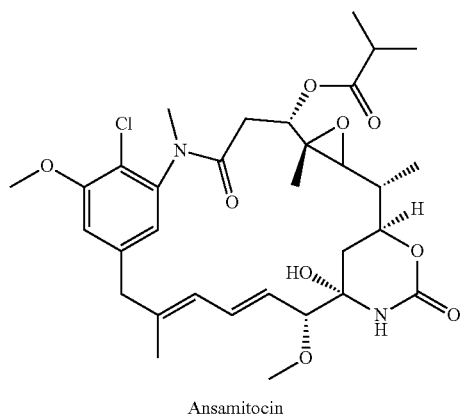

Ansamitocin

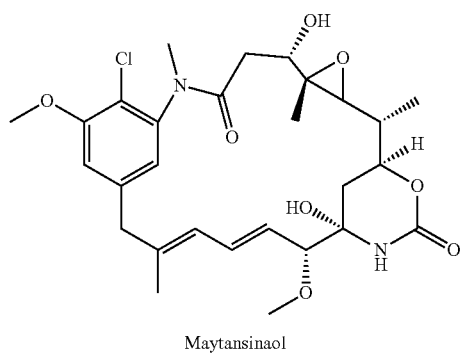

Maytansinaol

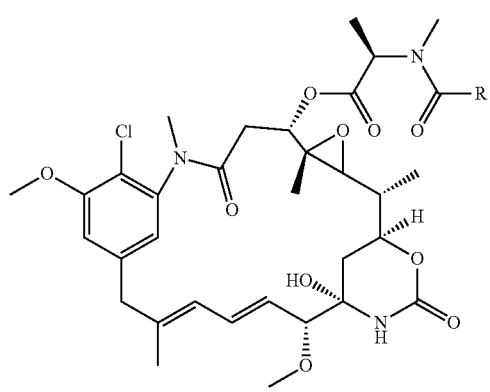

DM1-SMe, where R = CH$_2$CH$_2$SSMe

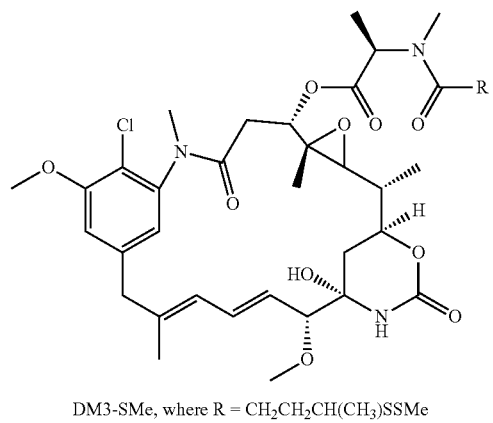

DM3-SMe, where R = CH$_2$CH$_2$CH(CH$_3$)SSMe

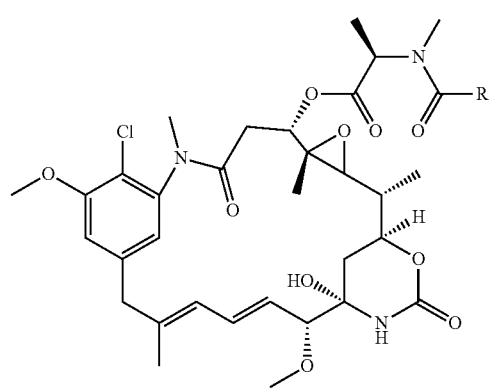

DM4-SMe, where R = CH$_2$CH$_2$C(CH$_3$)$_2$SSMe

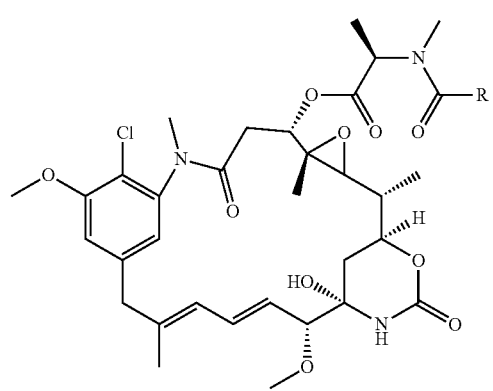

Mertansine (DM1), where R = CH$_2$CH$_2$SH

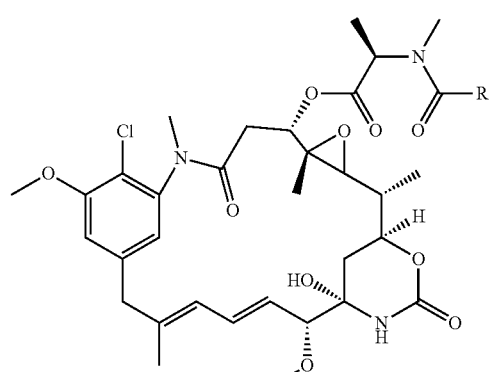

DM3, where R = CH$_2$CH$_2$CH(CH$_3$)SH

41
-continued

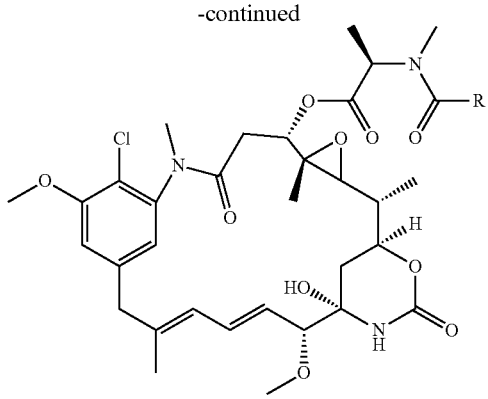

DM4, where R = CH₂CH₂C(CH₃)₂SH

Drug is an amatoxin, which binds RNA polymerase II.

A compound of formula (1), wherein Drug is an amatoxin. The sequence of amatoxins is Ile-Trp-Gly-Ile-Gly-Cys-Asn-Pro (SEQ ID NO: 11) with cross-linking between Trp and Cys via the sulfoxide (S=O) moiety.

A compound of formula (1), wherein Drug is selected from the group consisting of α-amanitin, β-amanitin, γ-amanitin, ε-amanitin, amanullin, amanullinic acid, amaninamide, amanin, and proamanullin:

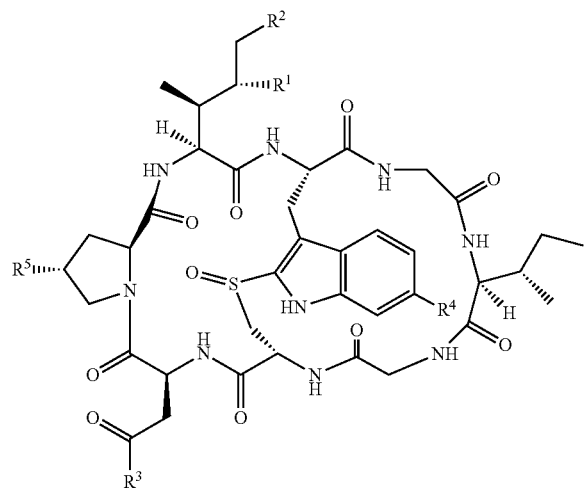

42 where α-amanitin ($R^1$=OH; $R^2$=OH; $R^3$=NH₂; $R^4$=OH; $R^5$=OH), β-amanitin ($R^1$=OH; $R^2$=OH; $R^3$=OH; $R^4$=OH; $R^5$=OH), γ-amanitin ($R^1$=OH; $R^2$=H; $R^3$=NH₂; $R^4$=OH; $R^5$=OH), ε-amanitin ($R^1$=OH; $R^2$=H; $R^3$=OH; $R^4$=OH; $R^5$=OH), amanullin ($R^1$=H; $R^2$=H; $R^3$=NH₂; $R^4$=OH; $R^5$=OH), amanullinic acid ($R^1$=H; $R^2$=H; $R^3$=OH; $R^4$=OH; $R^5$=OH), amaninamide ($R^1$=OH; $R^2$=OH; $R^3$=NH₂; $R^4$=H; $R^5$=OH), amanin ($R^1$=OH; $R^2$=OH; $R^3$=OH; $R^4$=H; $R^5$=OH), and proamanullin ($R^1$=H; $R^2$=H; $R^3$=NH₂; $R^4$=OH; $R^5$=H).

A compound of formula (1), wherein Drug is an alpha-amanitin:

and its analogs and derivatives.

Drug is a DNA-damaging agent, which binds minor groove of DNA and cause strand scission.

A compound of formula (1), wherein Drug is an enediyne antibiotic.

A compound of formula (1), wherein Drug is calicheamicin:

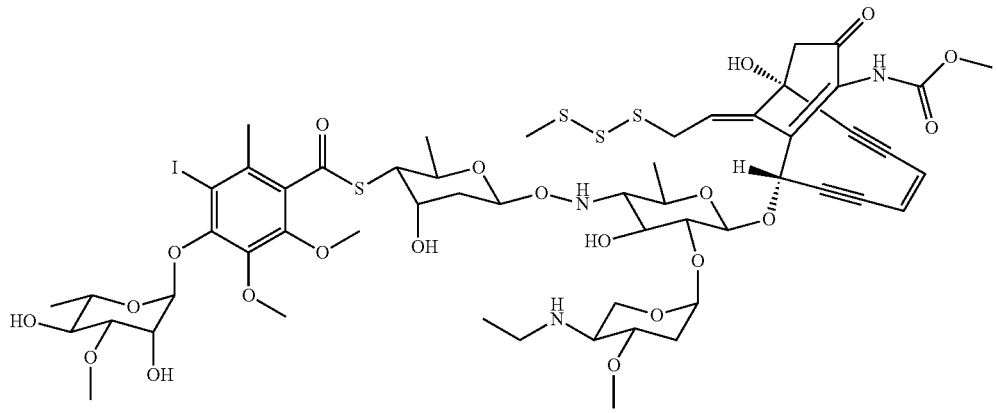 [SMILES: CCNC1COC(OC2C(O[C@H]3C#C/C=C\C#C[C@]4(O)CC(=O)C(NC(=O)OC)=C3/C4=C\CSSSC)OC(C)C(NOC3CC(O)C(SC(=O)c4c(C)c(I)c(OC5OC(C)C(O)C(OC)C5O)c(OC)c4OC)C(C)O3)C2O)CC1OC]

and its analogs and derivatives.

Drug is a DNA-damaging agent, which binds topoisomerase 1.

A compound of formula (1), wherein Drug is selected from the group consisting of camptothecin compounds:

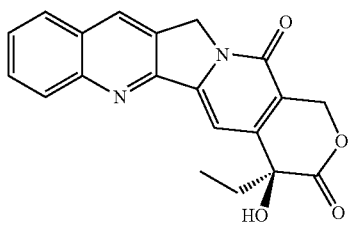 [SMILES: CC[C@@]1(O)C(=O)OCc2c1cc1n(c2=O)Cc2cc3ccccc3nc2-1]

A compound of formula (1), wherein Drug is an exatecan (DX-8951f):

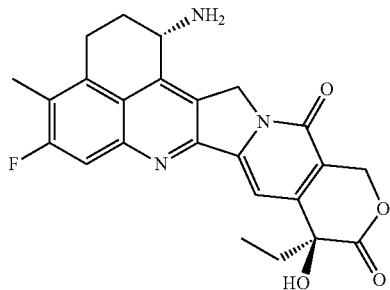 [SMILES: CC[C@@]1(O)C(=O)OCc2c1cc1n(c2=O)Cc2c-1nc1cc(F)c(C)c3c1c2[C@@H](N)CC3]

and its analogs and derivatives.

Figure 19A:
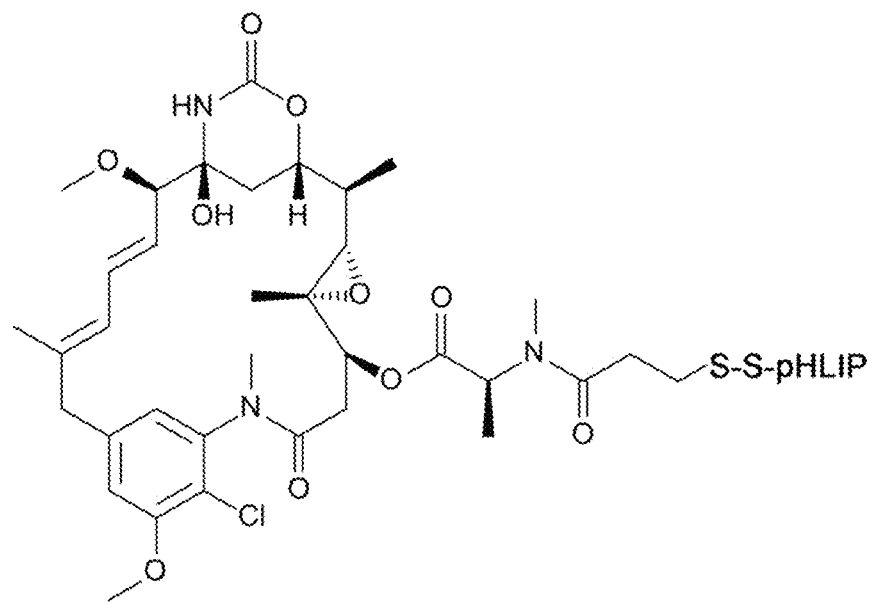
FIG. 19A is the chemical structure of pHLIP-S-S-mertansine construct.
Figure 19B:
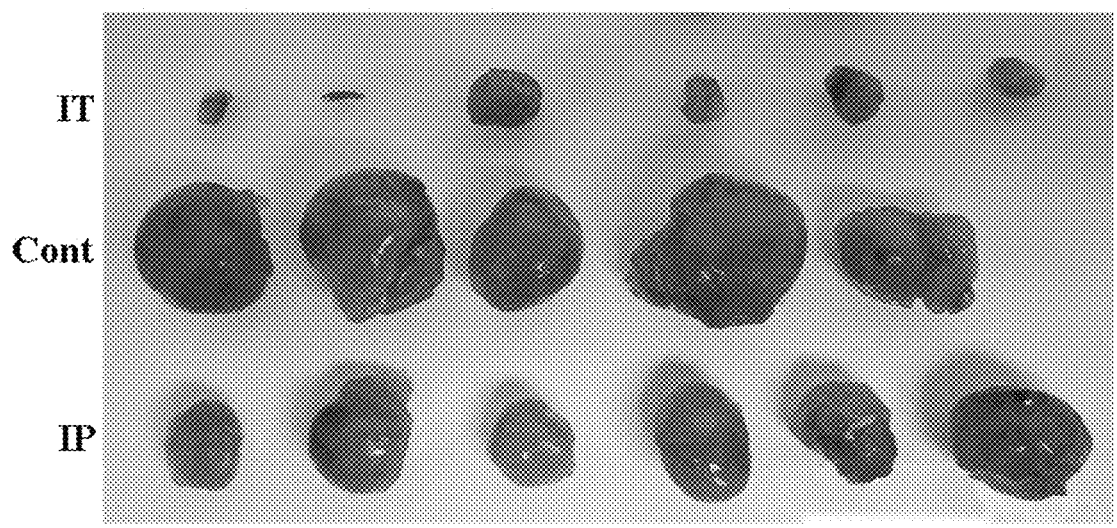
FIG. 19B depicts images of breast MDA-MB-231 tumors collected after intratumoral (IT) and intraperitoneal (IP) treatment with pHLIP-S-S-mertansine (see FIG. 21A) compared to the control group, which did not receive any treatment. The position indicated by "-" in IT treatment group indicates the tumor disappeared in the course of treatment and could not be collected.
Figure 19C:
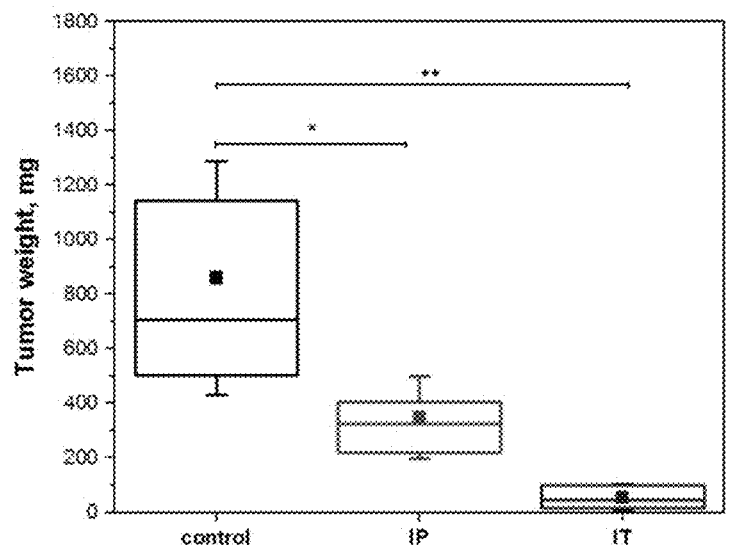
FIG. 19C depicts a box plot presenting mean (filled square), median, 25 and 75 percentiles (box itself) and standard deviation values of the tumor weights collected after IP and IT treatment with pHLIP-S-S-mertansine compared to the control (non-treated) group. P-level was calculated using two-tailed test.

Example 2: pHLIP®-Mediated Tumor Targeting and Cytoplasmic Delivery of Cytotoxic Tubulin Inhibitor, Mertansine, Group of Inhibitors of Tubulin's Maytansine Site Mertansine (DM1; CAS No: 139504-50-0) was conjugated to pHLIP® peptide membrane-inserting end via cleavable S-S link (FIG. 19A). The pHLIP® peptide used in the study: ADDQNPWRAYLDLLFPTDTLLLDLLWCA (SEQ ID NO: 3) was prepared by solid-phase synthesis. First, pHLIP-Cys was conjugated with Aldrithiol™-2 (2,2'-Dipyridyldisulfide; CAS No: 2127-03-9) to obtain pHLIP-S-S-Pyridine. pHLIP-S-S-Pyridine is purified by the reverse phase HPLC (the gradient: water and acetonitrile with 0.05% TFA). Then, mertansine was conjugated with pHLIP-S-S-Pyridine to exchange S-S bond and obtain pHLIP-S-S-mertansine followed by purification by RP-HPLC (the gradient: water and acetonitrile with 0.05% TFA) and lyophilization. The construct purity and identity was established by analytical RP-HPLC and surface-enhanced laser desorption/ionization time of flight (SELDI-TOF) mass spectroscopy, respectively. The construct concentration was calculated by absorbance at 280 nm for pHLIP® peptide with normalized from the absorbance of mertansine (see FIG. 19A).

pHLIP-S-S-mertansine dissolved in PBS and was given as multiple intraperitoneal (IP) or intratumoral (IT) injections (once in 3-4 days) into mice bearing MDA-MB-231 human triple negative breast or HeLa human cervical tumors in flanks of female athymic nude mice. The total combined dose of the multiple IP injections of pHLIP-S-S-mertansine was ~10 mg/kg, and the total combined dose of the multiple IT injections of pHLIP-S-S-mertansine was ~2.5 mg/kg. When the tumor reached a size of about 1 cm³ (about 1 g) in the control (non-treated) group, the animals were sacrificed; tumors were collected (FIG. 19B) and weighted (FIG. 19C).

About 60% of tumor weight reduction was observed after IP administration of pHLIP-S-S-mertansine, and more than 90% of tumor weight reduction was observed after IT administration of pHLIP-S-S-mertansine. In some cases the tumor disappeared after IT administration of the construct.

In a separate experiment, IT injections were performed, tumors disappeared and mice were left for several weeks. In 60% of these cases, no tumor re-growth was observed, and no signs of toxicity were observed in the course of IP or IT treatment.

Figure 20A:
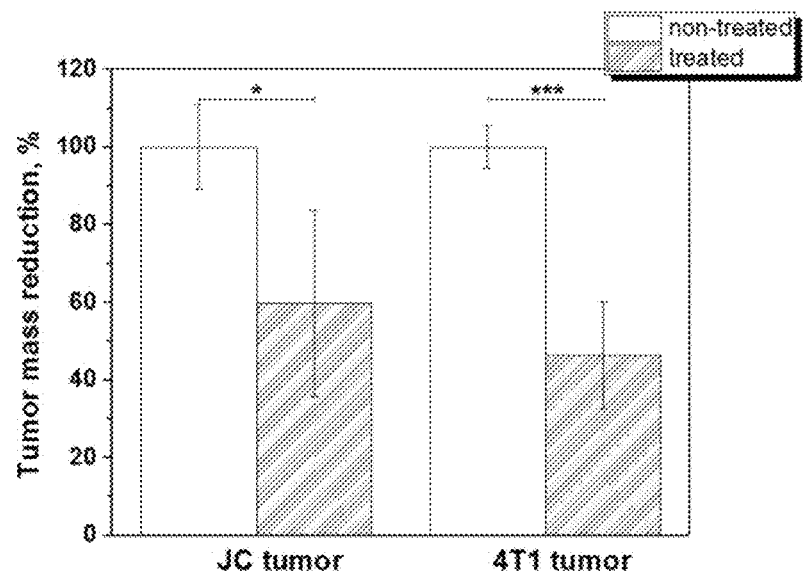
FIG. 20A is a bar graph depicting that tumor mass reduction was tested on mice bearing murine JC and 4T1 breast cancers after multiple IP administration of pHLIP-S-S-amanitin. P-level was calculated using two-tailed test.

Example 3: pHLIP©-Mediated Tumor Targeting and Cytoplasmic Delivery of Cytotoxic RNA Polymerase Inhibitor, Alpha-Amanitin, Group of Amatoxins Alpha-amanitin was conjugated to a pHLIP® peptide membrane-inserting end via cleavable S-S link. The pHLIP® peptide used in the study: ADDQNPWRAYLDLLFPTDTLLLDLLWCA (SEQ ID NO: 3) was prepared by solid-phase synthesis. To prepare pHLIP-S-S-amanitin, α-amanitin was conjugated to succinimidyl 3-(2-piridyldithio)propionate (SPDP) crosslinker, followed by purification using RP-HPLC (the gradient: water and acetonitrile with 0.05% TFA) and conjugation of the SPDP-amanitin to the C-terminal cysteine (bold and underlined in the sequence above) residues of pHLIP© peptide. Progression of the reaction and purification of pHLIP-S-S-amanitin was conducted using RP-HPLC (the gradient: water and acetonitrile with 0.05% TFA), followed lyophilization. The construct purity and identity was established by analytical RP-HPLC and surface-enhanced laser desorption/ionization time of flight (SELDI-TOF) mass spectroscopy, respectively. The construct concentration was calculated by absorbance at 310 nm, where, for α-amanitin, $\varepsilon_{310}$=13,000 M$^{-1}$ cm$^{-1}$.

pHLIP-S-S-amanitin dissolved in PBS and was given as multiple IP injections (once in 3-4 days) into female Balb/C mice bearing JC or 4T1 murine breast tumors in flank. The total combined dose of the multiple injections of pHLIP-S-S-amanitin was ~0.3 mg/kg. Each injection was accompanied by IP administration of 6.3 mg/kg of solution (200 μL) of glucose 30 min prior of pHLIP-S-S-amanitin administration. When the tumor reached a size of about 1 cm³ (about 1 g) in the control group, the animals were sacrificed, tumors were collected and weighted. About 40-50% reduction of tumor weight is observed (FIG. 20A).

The cytotoxic and highly polar agents, like amanitin, may be especially effective in topical applications. For example, the superficial bladder cancer may be treated with pHLIP-S-S-amantin, when the construct is administered via intravesical instillation. pHLIP-S-S-amanitin was tested on a panel of urinary bladder cancer cell lines at pH 7.4 and pH 6.0 to establish ratio, which demonstrated the difference in construct performance at different pHs, and, which could be interpreted as therapeutic index.

Figure 20B:
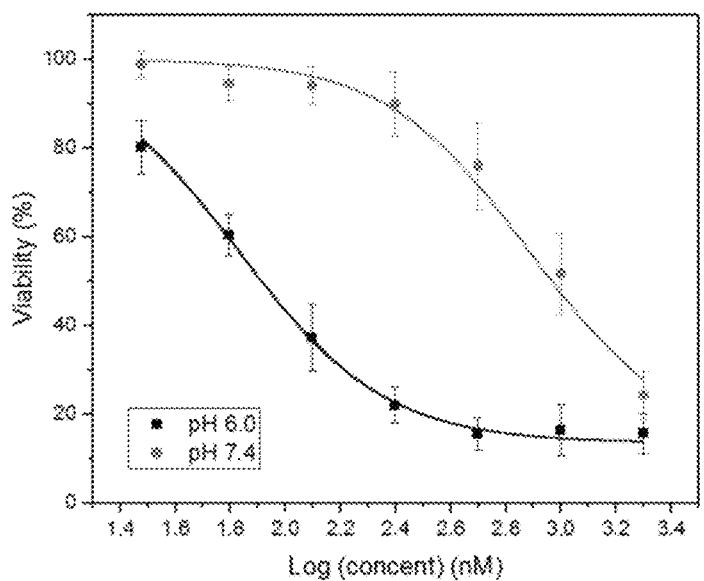
FIG. 20B is a line graph depicting cell viability after treatment with increasing concentrations of pHLIP-S-S-amanitin (in logarithmic scale) at pH 7.4 and pH 6.0.

Cancer cells were loaded in the wells of 96-well plates (5,000 cells/well) and incubated overnight. The standard growth medium was replaced with medium without FBS, at pH 6.0 or 7.4, containing increasing amounts of pHLIP-S-S-amanitin (from 0 to 2.0 μM). The pH 6.0 medium was prepared by mixing 13.3 g of dry DMEM in 1 L of deionized water. After two-hour incubation with the pHLIP-S-S-amanitin, the construct was removed and replaced with standard growth medium. Treatment with amanitin alone for two hours at concentrations up to 2 μM did not induce cell death. Cell viability was assessed after 48 hours using the colorimetric CellTiter 96 AQ$_{ueous}$ One Solution Cell Proliferation Assay by absorption measurement at 490 nm (FIG. 20B presents an example of the data obtained on SCaBER squamous cell carcinoma).

There was no difference in the viability of cells incubated with media, without construct, at pH 7.4 and pH 6.0; therefore, the role of pH was excluded from the consideration. Therapeutic index (TI) was calculated according to the equation:

$$TI = \frac{EC_{50}^{pH\,7.4}}{EC_{50}^{pH\,6.0}}$$

Table 8 below contains EC$_{50}$ values obtained for the treatment at pH 7.4 and pH 6.0 and calculated therapeutic index, which clearly indicated a pH-dependent cell action of pHLIP-S-S-amanitin. The ratio (TI) varied from 3.5 to 8 for different cell lines. pHLIP-S-S-amanitin distinguishes, binds to, and inserts into the cell membrane of cancer cells with low cell surface pH (pH5.5-6.5) from healthy cells with normal cell surface pH (pH7.4).

TABLE 8

The EC$_{50}$ values in nM calculated for treatment of pHLIP-S-S-amanitin with urinary bladder cancer cell lines at pH7.4 and pH6.0

|  | EC$_{50_{pH6.0}}$ | EC$_{50_{pH7.4}}$ | TI |
|---|---|---|---|
| HT-1197 cells: urinary bladder carcinoma | 193.8 | 804.8 | 4.2 |
| 5637 cells: grade II carcinoma | 89.9 | 378.2 | 4.2 |
| HT-1376 cells: grade III carcinoma | 766.7 | 3002.3 | 3.9 |
| SCaBER cells: squamous cell carcinoma | 127.8 | 1017.0 | 8.0 |
| J82 cells: transitional cell carcinoma | 83.7 | 549.1 | 6.6 |
| UM-UC-3 cells: transitional cell carcinoma | 446.2 | 2143.0 | 4.8 |
| SW780 cells: transitional cell carcinoma | 144.9 | 887.8 | 6.1 |
| T-24 cells: transitional cell carcinoma | 163.0 | 575.4 | 3.5 |
| TCCSUR cells: IV transitional cell carcinoma | 72.1 | 391.3 | 5.4 |
| RT4 cells: transitional cell papilloma | 107.3 | 473.3 | 4.4 |

Figure 21A:
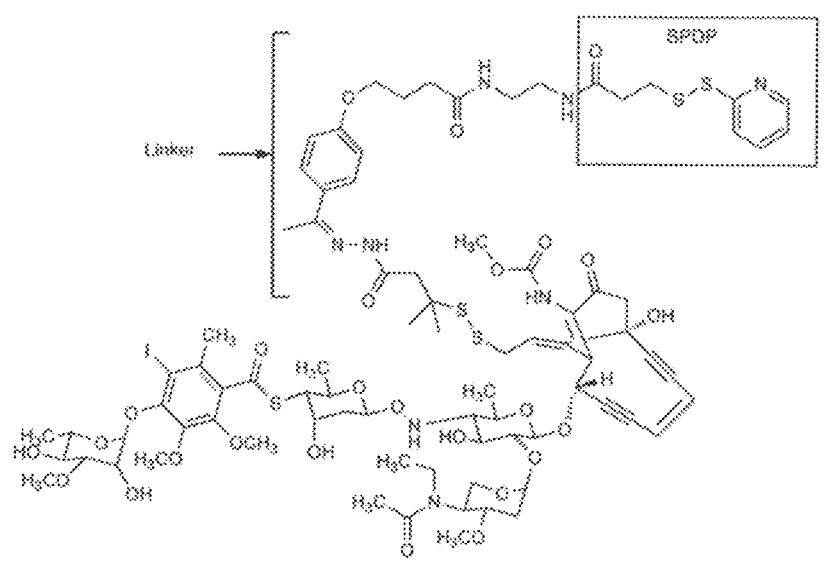
FIG. 21A depicts an image of a chemical structure of calicheamicin modified with succinimidyl 3-(2-pyridyldithio)propionate (SPDP) for direct conjugation with pHLIP containing a single Cys residue.

Example 4: pHLIP®-Mediated Tumor Targeting and Cytoplasmic Delivery of Cytotoxic DNA-Damaging Compound, Calicheamicin, Group of Enediyne Antibiotic Calicheamicin modified with SPDP was synthesized and purified by Cfm, GmbH (FIG. 21A). Calicheamicin-SPDP was used to conjugate with Cys residue of pHLIP® peptide's membrane-inserting end to obtain pHLIP-S-S-calicheamicin. The pHLIP® peptide used in the study: ADDQNPWRAYLDLLFPTDTLLLDLLWCA (SEQ ID NO: 3) was prepared by solid-phase synthesis. Purification of the pHLIP-S-S-calicheamicin was conducted using RP-HPLC (the gradient: 10 mM TEAA buffer and acetonitrile), followed by lyophilization. The construct purity and identity was established by analytical RP-HPLC and surface-enhanced laser desorption/ionization time of flight (SELDI-TOF) mass spectroscopy, respectively. Construct concentration was calculated by absorbance at 280 nm for pHLIP® peptide with correction on absorbance of calicheamicin. pHLIP-S-S-calicheamicin dissolved in PBS was given as multiple intraperitoneal (IP) or intratumoral (IT) injections (once in 3-4 days) into mice bearing HeLa human cervical tumors in flank of female athymic nude mice.

Figure 21B:
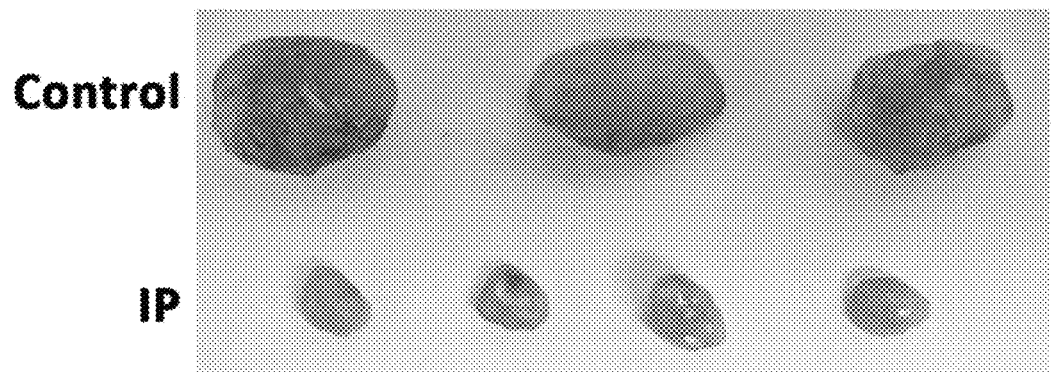
FIG. 21B depicts images of cervical HeLa tumors collected after IP treatment with pHLIP-S-S-calicheamicin compared to the control group, which did not receive any treatment.
Figure 21C:
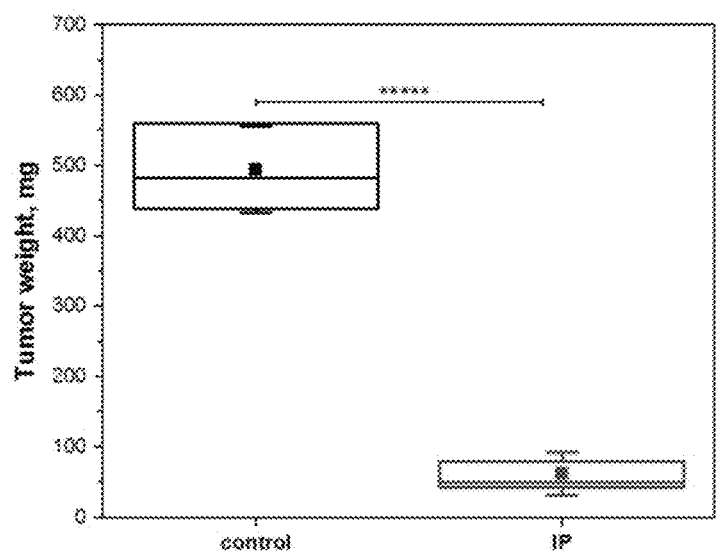
FIG. 21C depicts box plot presenting mean (filled squares), median, 25 and 75 percentiles (box) and standard deviation values of tumor weights after IP and IT treatment with pHLIP-S-S-calicheamicin compared to the control (non-treated) group. P-level was calculated using two-tailed test.

The total combined dose of the multiple IP injections of pHLIP-S-S-calicheamicin was ~1.5 mg/kg. When tumors reached about 0.5 g in the control (non-treated) group, the animals were sacrificed; tumors were collected (FIG. 21B) and weighted (FIG. 21C).

Figure 22:
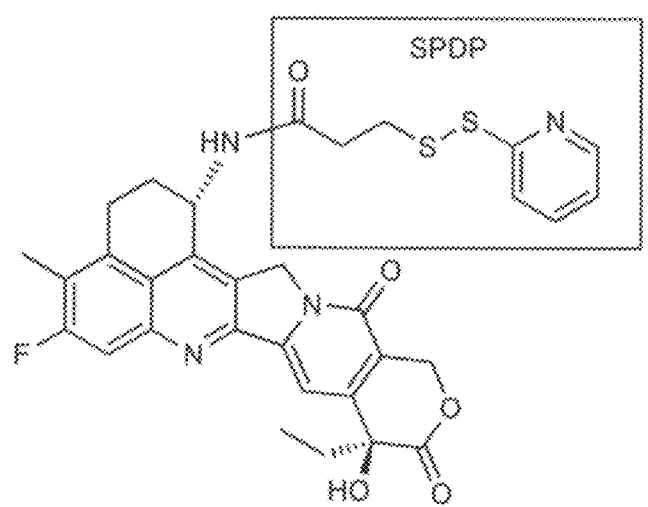
FIG. 22 depicts an image of a chemical structure of exatecan modified with SPDP for direct conjugation with pHLIP® containing single Cys residue.

About 88% of tumor weight reduction was observed after IP administration of pHLIP-S-S-calicheamicin Example 5: pHLIP®-Mediated Tumor Targeting and Cytoplasmic Delivery of Cytotoxic DNA-Damaging Compound, Topoisomerase I Inhibitor Exatecan, Group of Camptothecin Compounds Exatecan modified with SPDP is synthesized and purified by Cfm GmbH (FIG. 22). Exatecan-SPDP is conjugated with a single Cys residue of pHLIP® peptide's membrane-inserting end to obtain pHLIP-S-S-exatecan. The pHLIP® peptide used in the study: ADDQNPWRAYLDLLFPTDTLLLDLLWCA (SEQ ID NO: 3) is prepared by solid-phase synthesis. Purification of pHLIP-S-S-exatecan is conducted using RP-HPLC followed by lyophilization. The construct purity and identity are established by analytical RP-HPLC and surface-enhanced laser desorption/ionization time of flight (SELDI-TOF) mass spectroscopy, respectively. Construct concentration was calculated by absorbance at 280 nm for pHLIP® peptide with correction on absorbance of exatecan.

pHLIP-S-S-exatecan dissolved in PBS is given as multiple intraperitoneal (IP) injections (once in 3-4 days) into mice bearing HeLa human cervical tumors in flank of female athymic nude mice. When tumors reached about 1 cm$^3$ (about 1 g) in the control (non-treated) group, the animals are sacrificed; tumors were collected and weighted.

About 50-60% of tumor weight reduction is observed after IP administration of pHLIP-S-S-exatecan, and more than 70% of tumor weight reduction is observed after IT administration of pHLIP-S-S-exatecan.

Example 6

In aspects, provided herein is a composition comprising a potent cytotoxic compound and a pHLIP® peptide. For example, the cytotoxic compound is a cytotoxic tubulin inhibitor compound, which inhibits tubulin polymerization and destabilization of microtubule structures. In other embodiments, the cytotoxic tubulin inhibitor compound binds to a maytansine site.

In embodiments, the cytotoxic tubulin inhibitor compound includes a maytansine, ansamitocin, maytansinol, D-alanyl maytansine, or maytansine analogs bearing disulfide or thiol groups and their derivatives. For example, the cytotoxic tubulin inhibitor compound includes mertansine or a derivative thereof.

In embodiments, the cytotoxic compound is a cytotoxic RNA polymerase inhibitor. For example, the cytotoxic RNA polymerase inhibitor compound is an amatoxins. In other examples, the cytotoxic RNA polymerase inhibitor compound is an alpha-amanitin or a derivative thereof.

In embodiments, the cytotoxic compound is a cytotoxic DNA-damaging compound. For example, the cytotoxic DNA damaging compound is an enediyne antibiotic. In other examples, the cytotoxic DNA damaging compound is calicheamicin or a derivative thereof. In embodiments, the cytotoxic DNA damaging compound is a topoisomerase I inhibitor. For example, the cytotoxic topoisomerase I inhibitor compound is a camptothecin compound. In embodiments, the cytotoxic topoisomerase I inhibitor compound is exatecan or a derivative thereof.

In embodiments, the cytotoxic compound comprises limited targeting of tumors.

In embodiments, the composition described herein further includes a linker between said cytotoxic compound and said pHLIP® peptide. For example, the linker includes a disulfide bond or an acid-liable bond. In embodiments, the linker is cleavable. In other embodiments, the linker is not cleavable. In embodiments, the linker is self-immolating.

In embodiments, the composition described herein further includes a modulator of polarity.

In embodiments, also provided herein is a composition including a pHLIP® peptide, wherein the pHLIP® peptide has the sequence ADDQNPWRAYLDLLFPTDTLLLDLLWXA (SEQ ID NO: 1) or ADQDNPWRAYLDLLFPTDTLLLDLLWXA (SEQ ID NO: 2), wherein upper case "X" indicates any amino acid residue and can include a lysine (Lys), a cysteine (Cys), or an Azido-containing amino acid.

In embodiments, the composition has the following structure: Peptide-Link-B wherein "Peptide" is a first pHLIP® peptide comprising the sequence ADDQNPWRAYLDLLFPTDTLLLDLLWXA (SEQ ID NO: 1) or ADQDNPWRAYLDLLFPTDTLLLDLLWXA (SEQ ID NO: 2), "B" is a second pHLIP© peptide comprising the sequence ADDQNPWRAYLDLLFPTDTLLLDLLWXA (SEQ ID NO: 1) or ADQDNPWRAYLDLLFPTDTLLLDLLWXA (SEQ ID NO: 2), wherein upper case "X" indicates any amino acid residue and can include lysine (Lys), Cysteine (Cys), or Azido-containing amino acid; "Link" is a polyethylene glycol linker, and each "-" is a covalent bond.

In aspects, provided herein is a method of killing cells in acidic diseased tissue, comprising administering to a subject a composition comprising a cytotoxic compound and a pHLIP© peptide.

In other embodiments, the method includes that the subject has a solid tumor. For example, in embodiments, the subject has a bladder tumor.

In embodiments, the composition is injected directly into a tumor mass. In embodiments, the composition is instilled into a bladder.

In embodiments, the composition is topically applied. In other embodiments, the composition is systemically administered. In other embodiments, the tubulin inhibitor compound is delivered into the cytosols of cancer cells. In examples, the cytotoxic compound is delivered into the cytosols of senescent cells.

In embodiments, the cytotoxic compound is targeted to acidic tissue to induce a biological effect predominantly within targeted tissue.

In embodiments, the cytotoxic compound is delivered intracellularly to induce a biological effect. In other embodiments, the cytotoxic compound has limited tumor targeting ability in the absence of said pHLIP®.

In embodiments, the composition targets said cytotoxic compound preferentially to a diseased tissue compared to a healthy tissue, thereby minimizing damage to said healthy tissue.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means ±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) or polypeptide is free of the amino acid sequences, or nucleic acid sequences that flank it in its naturally-occurring state. Purified also defines a degree of sterility that is safe for administration to a human subject, e.g., lacking infectious or toxic agents. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. That is, an individual described as a "patient" does not necessarily have a given disease, but may be merely seeking medical advice.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A the "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of killing cells in acidic diseased tissue in a subject, comprising administering to the subject a composition comprising a cytotoxic compound and a pH low insertion peptide, wherein the pH low insertion peptide comprises the sequence ADQDNPWRAYLDLLFPTDTLLLDLLWXA (SEQ ID NO: 2), wherein upper case "X" indicates any amino acid residue or an Azido-containing amino acid.

2. The method of claim 1, further comprising a linker between said cytotoxic compound and said pH low insertion peptide.

3. The method of claim 2, wherein said linker comprises a disulfide bond linker.

4. The method of claim 1, wherein the acidic diseased tissue comprises breast cancer.

5. The method of claim 1, wherein said cytotoxic compound is a cytotoxic tubulin inhibitor compound, which inhibits tubulin polymerization and destabilization of microtubule structures.

6. The method of claim 5, wherein said cytotoxic tubulin inhibitor compound binds to a maytansine site.

7. The method of claim 5, wherein said cytotoxic tubulin inhibitor compound comprises a maytansine, ansamitocin, maytansinol, D-alanyl maytansine, or maytansine analogs bearing disulfide or thiol groups.

8. The method of claim 5, wherein said cytotoxic tubulin inhibitor compound comprises mertansine.

9. The method of claim 1, wherein said cytotoxic compound comprises a cytotoxic RNA polymerase inhibitor.

10. The method of claim 9, wherein said cytotoxic RNA polymerase inhibitor comprises an amatoxin.

11. The method of claim 9, wherein said cytotoxic RNA polymerase inhibitor comprises an alpha-amanitin.

12. The method of claim 1, wherein said cytotoxic compound comprises a cytotoxic DNA damaging compound.

13. The method of claim 12, wherein said cytotoxic DNA damaging compound comprises an enediyne antibiotic.

14. The method of claim 12, wherein said cytotoxic DNA damaging compound comprises a topoisomerase I inhibitor.

15. The method of claim 14, wherein said topoisomerase I inhibitor comprises camptothecin.

16. The method of claim 14, wherein said topoisomerase I inhibitor comprises exatecan.

17. The method of claim 2, wherein said linker comprises a disulfide bond or an acid-labile bond.

18. The method of claim 2, wherein said linker is cleavable.

19. The method of claim 2, wherein said linker is not cleavable.

20. The method of claim 2, wherein said linker is self-immolating.

21. The method of claim 1, wherein the composition further comprises a modulator of polarity.

22. The method of claim 1, wherein said composition comprises the following structure:

Peptide-Link-B wherein "Peptide" is the pH low insertion peptide comprising the sequence ADQDNPWRAYLDLLFPTDTLLLDLLWXZ (SEQ ID NO: 2), "B" is a second pH low insertion peptide comprising the sequence ADDQNPWRAYLDLLFPTDTLLLDLLWXA (SEQ ID NO: 1) or ADQDNPWRAYLDLLFPTDTLLLDLLWXA (SEQ ID NO: 2), wherein upper case "X" indicates any amino acid residue and can include an Azido-containing amino acid; wherein "Link" is a polyethylene glycol linker, and each "-" is a covalent bond.

23. The method of claim 1, wherein said subject comprises a solid tumor.

24. The method of claim 1, wherein said subject comprises a bladder tumor.

25. The method of claim 1, wherein said composition is injected directly into a tumor mass.

26. The method of claim 1, wherein said composition is instilled into a bladder.

27. The method of claim 1, wherein said composition is topically applied.

28. The method of claim 1, wherein said composition is systemically administered.

29. The method of claim 1, wherein said cytotoxic compound is delivered into the cytosols of cancer cells.

30. The method of claim 1, wherein said cytotoxic compound is delivered into the cytosols of senescent cells.

31. The method of claim 1, wherein said cytotoxic compound is targeted to acidic tissue to induce a biological effect predominantly within targeted tissue.

32. The method of claim 1, wherein said cytotoxic compound is delivered intracellularly to induce a biological effect.

33. The method of claim 1, wherein said cytotoxic compound comprises limited tumor targeting ability in the absence of said pH low insertion peptide.

34. The method of claim 1, wherein said composition targets said cytotoxic compound preferentially to a diseased tissue compared to a healthy tissue, thereby minimizing damage to said healthy tissue.

35. The method of claim 1, wherein the cytotoxic compound comprises a calicheamicin compound.

36. A method of killing cells in acidic diseased tissue in a subject, comprising administering to the subject a composition comprising a cytotoxic compound and a pH low insertion peptide, wherein the pH low insertion peptide comprises the sequence ADQDNPWRAYLDLLFPTDTLLLDLLWXA (SEQ ID NO: 2), wherein upper case "X" indicates any amino acid residue or an Azido-containing amino acid, and wherein the cytotoxic agent comprises a calicheamicin compound.

37. The method of claim 36, further comprising a linker between said cytotoxic compound and said pH low insertion peptide.

38. The method of claim 37, wherein said linker comprises a disulfide bond linker.

39. The method of claim 36, wherein the acidic diseased tissue comprises breast cancer.

40. The method of claim 36, wherein said cytotoxic compound further comprises a cytotoxic tubulin inhibitor compound, which inhibits tubulin polymerization and destabilization of microtubule structures.

41. The method of claim 40, wherein said cytotoxic tubulin inhibitor compound binds to a maytansine site.

42. The method of claim 40, wherein said cytotoxic tubulin inhibitor compound comprises a maytansine, ansamitocin, maytansinol, D-alanyl maytansine, or maytansine analogs bearing disulfide or thiol groups.

43. The method of claim 40, wherein said cytotoxic tubulin inhibitor compound comprises mertansine.

44. The method of claim 36, wherein said cytotoxic compound further comprises a cytotoxic RNA polymerase inhibitor.

45. The method of claim 44, wherein said cytotoxic RNA polymerase inhibitor comprises an amatoxin.

46. The method of claim 44, wherein said cytotoxic RNA polymerase inhibitor comprises an alpha-amanitin.

47. The method of claim 36, wherein said cytotoxic compound further comprises a cytotoxic DNA damaging compound.

48. The method of claim 47, wherein said cytotoxic DNA damaging compound comprises an enediyne antibiotic.

49. The method of claim 47, wherein said cytotoxic DNA damaging compound comprises a topoisomerase I inhibitor.

50. The method of claim 49, wherein said topoisomerase I inhibitor comprises camptothecin.

51. The method of claim 49, wherein said topoisomerase I inhibitor comprises exatecan.

52. The method of claim 37, wherein said linker comprises a disulfide bond or an acid-labile bond.

53. The method of claim 37, wherein said linker is cleavable.

54. The method of claim 37, wherein said linker is not cleavable.

55. The method of claim 37, wherein said linker is self-immolating.

56. The method of claim 36, wherein the composition further comprises a modulator of polarity.

57. The method of claim 36, wherein said subject comprises a solid tumor.

58. The method of claim 36, wherein said subject comprises a bladder tumor.

59. The method of claim 36, wherein said composition is injected directly into a tumor mass.

60. The method of claim 36, wherein said composition is instilled into a bladder.

61. The method of claim 36, wherein said composition is topically applied.

62. The method of claim 36, wherein said composition is systemically administered.

63. The method of claim 36, wherein said cytotoxic compound is delivered into the cytosols of senescent cells.

64. The method of claim 36, wherein said cytotoxic compound is targeted to acidic tissue to induce a biological effect predominantly within targeted tissue.

65. The method of claim 36, wherein said cytotoxic compound is delivered intracellularly to induce a biological effect.

66. The method of claim 36, wherein said cytotoxic compound comprises limited tumor targeting ability in the absence of said pH low insertion peptide.

67. The method of claim 36, wherein said composition targets said cytotoxic compound preferentially to a diseased tissue compared to a healthy tissue, thereby minimizing damage to said healthy tissue.

68. The method of claim 1, wherein said composition is an intravenous composition.

69. The method of claim 36, wherein said composition is an intravenous composition.

* * * * *

SEQUENCE LISTING

```
<160> NUMBER OF SEQ ID NOS: 223

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Any amino acid
<220> FEATURE:
<223> OTHER INFORMATION: See specification as filed for detailed
      description of substitutions and preferred embodiments

<400> SEQUENCE: 1

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Xaa Ala
            20                  25

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (27)..(27)
<223> OTHER INFORMATION: Any amino acid
<220> FEATURE:
<223> OTHER INFORMATION: See specification as filed for detailed
      description of substitutions and preferred embodiments

<400> SEQUENCE: 2

Ala Asp Gln Asp Asn Pro Trp Arg Ala Tyr Leu Asp Leu Leu Phe Pro
1               5                   10                  15

Thr Asp Thr Leu Leu Leu Asp Leu Leu Trp Xaa Ala
            20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Cys Ala
            20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Lys Ala
            20                  25

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Asp Gln Asp Asn Pro Trp Arg Ala Tyr Leu Asp Leu Leu Phe Pro
1               5                   10                  15

Thr Asp Thr Leu Leu Leu Asp Leu Leu Trp Cys Ala
            20                  25

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Asp Gln Asp Asn Pro Trp Arg Ala Tyr Leu Asp Leu Leu Phe Pro
```

```
                1               5                   10                  15
Thr Asp Thr Leu Leu Leu Asp Leu Leu Trp Lys Ala
                20                  25
```

<210> SEQ ID NO 7
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Ala Glu Gln Asn Pro Ile Tyr Trp Ala Arg Tyr Ala Asp Trp Leu Phe
1               5                   10                  15
Thr Thr Pro Leu Leu Leu Asp Leu Ala Leu Leu Val Asp Ala Asp
                20                  25                  30
Glu Gly Thr
        35
```

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Ala Glu Gln Asn Pro Ile Tyr
1               5
```

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Trp Ala Arg Tyr Ala Asp Trp Leu Phe Thr Thr Pro Leu Leu Leu Leu
1               5                   10                  15
Asp Leu Ala Leu Leu Val
            20
```

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Asp Ala Asp Glu Gly Thr
1               5
```

<210> SEQ ID NO 11
<211> LENGTH: 8
<212> TYPE: PRT
<213> ORGANISM: Unknown
<220> FEATURE:
<223> OTHER INFORMATION: Description of Unknown:
      Amatoxin peptide

```
<400> SEQUENCE: 11

Ile Trp Gly Ile Gly Cys Asn Pro
1               5

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Asp Gln Asp Asn Pro Trp Arg Ala Tyr Leu Asp Leu Leu Phe Pro
1               5                   10                  15

Thr Asp Thr Leu Leu Leu Asp Leu Leu Trp Cys Ala
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Asp Gln Asp Asn Pro Trp Arg Ala Tyr Leu Asp Leu Leu Phe Pro
1               5                   10                  15

Thr Asp Thr Leu Leu Leu Asp Leu Leu Trp Lys Ala
            20                  25

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr
        35

<210> SEQ ID NO 15
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Glu Gln Asn Pro Ile Tyr Trp Ala Arg Tyr Ala Asp Trp Leu Phe
1               5                   10                  15

Thr Thr Pro Leu Leu Leu Asp Leu Ala Leu Leu Val Asp Ala Asp
            20                  25                  30

Glu Gly Thr
        35
```

```
<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Cys Lys Ala
            20                  25

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Asp Ala Asp Glu Cys Gly
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Asp Ala Asp Glu Lys Gly
            20                  25                  30

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Asp Ala Asp Glu Lys Cys
            20                  25                  30

Gly

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 20

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp Asp Ala Asp Glu Gly
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Lys Asp Asp Gln Asn Pro Trp Arg Ala Tyr Leu Asp Leu Leu Phe
1               5                   10                  15

Pro Thr Asp Thr Leu Leu Leu Asp Leu Leu Trp Asp Ala Asp Glu Gly
            20                  25                  30

<210> SEQ ID NO 22
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
            35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Cys Thr
            35

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Gly Glu Gln Asn Pro Ile Tyr Trp Ala Arg Tyr Ala Asp Trp Leu
1               5                   10                  15
```

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 28
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Lys Glu Gln Asn Pro Ile Tyr Trp Ala Arg Tyr Ala Asp Trp Leu
1               5                   10                  15

```
Phe Thr Thr Pro Leu Leu Leu Leu Asp Leu Ala Leu Leu Val Asp Ala
            20                  25                  30

Asp Glu Gly Thr Gly
        35

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Cys Thr
        35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30

Asp Glu Gly Thr Gly
        35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Cys Glu Gln Asn Pro Ile Tyr Trp Ala Arg Tyr Ala Asn Trp Leu
```

```
               1               5                   10                  15
Phe Thr Thr Pro Leu Leu Leu Asn Leu Ala Leu Leu Val Asp Ala
               20                  25                  30
Asp Glu Gly Thr
        35

<210> SEQ ID NO 33
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Cys Glu Gln Asn Pro Ile Tyr Trp Ala Arg Tyr Ala Lys Trp Leu
1               5                   10                  15
Phe Thr Thr Pro Leu Leu Leu Lys Leu Ala Leu Leu Val Asp Ala
               20                  25                  30
Asp Glu Gly Thr Gly
        35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Gly Glu Gln Asn Pro Ile Tyr Trp Ala Arg Tyr Ala Asp Trp Leu
1               5                   10                  15
Phe Thr Thr Pro Leu Leu Leu Asp Leu Ala Leu Leu Val Asn Ala
               20                  25                  30
Asn Gln Gly Thr
        35

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Ala Glu Gln Asn Pro Ile Tyr Trp Ala Arg Tyr Ala Asp Trp Leu
1               5                   10                  15
Phe Thr Thr Pro Leu Leu Leu Ala Leu Ala Leu Leu Val Asp Ala
               20                  25                  30
Asp Glu Gly Thr
        35

<210> SEQ ID NO 36
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36
```

```
Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr Lys Cys Gly
        35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Ala Glu Gln Asn Pro Ile Tyr Trp Ala Arg Tyr Ala Asp Trp Leu
1               5                   10                  15

Phe Thr Thr Ala Leu Leu Leu Leu Asp Leu Ala Leu Leu Val Asp Ala
            20                  25                  30

Asp Glu Gly Thr
        35

<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40
```

Ala Ala Glu Gln Asn Pro Ile Tyr Trp Ala Arg Tyr Ala Glu Trp Leu
1               5                   10                  15

Phe Thr Thr Pro Leu Leu Leu Asp Leu Ala Leu Leu Val Asp Ala
            20                  25                  30

Asp Glu Gly Thr
        35

<210> SEQ ID NO 41
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Ala Glu Gln Asn Pro Ile Ile Tyr Trp Ala Arg Tyr Ala Asp Trp
1               5                   10                  15

Leu Phe Thr Asp Leu Pro Leu Leu Leu Asp Leu Leu Ala Leu Leu
            20                  25                  30

Val Asp Ala Asp Glu Gly Thr
        35

<210> SEQ ID NO 42
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Glu Gln Asn Pro Ile Tyr Trp Ala Gln Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr Cys Gly
        35

<210> SEQ ID NO 43
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
            20                  25                  30

Asp Glu Gly Thr Cys Gly
        35

<210> SEQ ID NO 44
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
        35

<210> SEQ ID NO 45
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 46
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Gly Glu Gln Asn Pro Ile Tyr Trp Ala Arg Tyr Ala Trp Asp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Ala Glu Gln Asn Pro Ile Tyr Trp Ala Arg Tyr Ala Asp Trp Leu
1               5                   10                  15

Phe Thr Thr Gly Leu Leu Leu Leu Asp Leu Ala Leu Leu Val Asp Ala
            20                  25                  30

Asp Glu Gly Thr
        35

<210> SEQ ID NO 48
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Thr
        35

<210> SEQ ID NO 50
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Gly Cys Thr
        35

<210> SEQ ID NO 51
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Cys Asp Asp Asp Glu Asp Asn Pro Ile Tyr Trp Ala Arg Tyr Ala His
1               5                   10                  15

Trp Leu Phe Thr Thr Pro Leu Leu Leu His Gly Ala Leu Leu Val
            20                  25                  30

Asp Ala Asp Glu Thr
        35

<210> SEQ ID NO 52
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Gly Thr
        35

<210> SEQ ID NO 53
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 54
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Gly Thr
        35

<210> SEQ ID NO 55
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 56
<211> LENGTH: 37
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 56

Asp Asp Asp Glu Asp Asn Pro Ile Tyr Trp Ala Arg Tyr Ala His Trp
1               5                   10                  15
Leu Phe Thr Thr Pro Leu Leu Leu His Gly Ala Leu Leu Val Asn
            20                  25                  30
Ala Asn Glu Gly Thr
        35

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 57

Ala Glu Gln Asn Pro Ile Tyr Trp Ala Arg Tyr Ala Asp Phe Leu Phe
1               5                   10                  15
Thr Thr Pro Leu Leu Leu Leu Asp Leu Ala Leu Leu Val Asp Ala Asp
            20                  25                  30
Glu Thr

<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 58

Ala Glu Gln Asn Pro Ile Tyr Phe Ala Arg Tyr Ala Asp Trp Leu Phe
1               5                   10                  15
Thr Thr Pro Leu Leu Leu Leu Asp Leu Ala Leu Leu Val Asp Ala Asp
            20                  25                  30
Glu Gly Thr
        35

<210> SEQ ID NO 59
<211> LENGTH: 34
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 59

Ala Glu Gln Asn Pro Ile Tyr Phe Ala Arg Tyr Ala Asp Phe Leu Phe
1               5                   10                  15
Thr Thr Pro Leu Leu Leu Leu Asp Leu Ala Leu Leu Trp Asp Ala Asp
            20                  25                  30
Glu Thr

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

Ala Lys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp Cys Gly
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu Cys Gly
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Lys Glu Asp Gln Asn Asp Pro Tyr Trp Ala Arg Tyr Ala Asp Trp
1               5                   10                  15

Leu Phe Thr Thr Pro Leu Leu Leu Leu Asp Leu Ala Leu Leu Val Gly
            20                  25                  30

```
<210> SEQ ID NO 65
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ala Lys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 66
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Cys Gly
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 68
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Lys Asp Asp Gln Asn Pro Trp Arg Ala Tyr Leu Asp Leu Leu Phe
```

```
1               5                   10                  15
Pro Thr Asp Thr Leu Leu Leu Asp Leu Leu Trp Cys
            20                  25

<210> SEQ ID NO 70
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Cys Glu Glu Gln Asn Pro Trp Arg Ala Tyr Leu Glu Leu Leu Phe
1               5                   10                  15

Pro Thr Glu Thr Leu Leu Leu Glu Leu Leu Trp
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Asp Asn Asn Asn Pro Trp Arg Ala Tyr Leu Asp Leu Leu Phe Pro
1               5                   10                  15

Thr Asp Thr Leu Leu Leu Asp Trp
            20

<210> SEQ ID NO 73
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Glu Glu Gln Gln Pro Trp Ala Gln Tyr Leu Glu Leu Leu Phe Pro
1               5                   10                  15

Thr Glu Thr Leu Leu Leu Glu Trp
            20

<210> SEQ ID NO 74
<211> LENGTH: 24
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 74

Cys Glu Glu Gln Gln Pro Trp Arg Ala Tyr Leu Glu Leu Leu Phe Pro
1               5                   10                  15

Thr Glu Thr Leu Leu Leu Glu Trp
            20

<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Cys Asp Asp Asp Asp Asn Pro Asn Tyr Trp Ala Arg Tyr Ala Asn
1               5                   10                  15

Trp Leu Phe Thr Thr Pro Leu Leu Leu Asn Gly Ala Leu Leu Val
            20                  25                  30

Glu Ala Glu Glu Thr
        35

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Cys Asp Asp Asp Asp Asn Pro Asn Tyr Trp Ala Arg Tyr Ala Pro
1               5                   10                  15

Trp Leu Phe Thr Thr Pro Leu Leu Leu Pro Gly Ala Leu Leu Val
            20                  25                  30

Glu Ala Glu Glu
        35

<210> SEQ ID NO 77
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Thr Glu Asp Ala Asp Val Leu Leu Ala Leu Asp Leu Leu Leu Pro
1               5                   10                  15

Thr Thr Phe Leu Trp Asp Ala Tyr Arg Ala Trp Tyr Pro Asn Gln Glu
            20                  25                  30

Cys Ala

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 78

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Glu Gln Asn Pro Ile Tyr Trp Ala Arg Tyr Ala Asp Trp Leu Phe
1               5                   10                  15

Thr Thr Pro Cys Leu
            20

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Cys Glu Gln Asn Pro Ile Tyr Trp Ala Arg Tyr Ala Asp Trp Leu
1               5                   10                  15

Phe Thr Thr Pro Leu
            20

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Glu Gln Asn Pro Ile Tyr Phe Ala Arg Tyr Ala Asp Trp Leu Phe
1               5                   10                  15

Thr Thr Pro Leu
            20

<210> SEQ ID NO 82
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 83
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Glu Gln Asn Pro Ile Tyr Trp Ala Arg Tyr Ala Asp Leu Leu Phe
1               5                   10                  15

Pro Thr Thr Leu Ala Trp
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Glu Asp Gln Asn Pro Trp Ala Arg Tyr Ala Asp Leu Leu Phe Pro
1               5                   10                  15

Thr Thr Leu Ala Trp
            20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Glu Asp Gln Asn Pro Trp Ala Arg Tyr Ala Asp Leu Leu Phe Pro
1               5                   10                  15

Thr Thr Leu Trp
            20

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Cys Glu Asp Gln Asn Pro Trp Ala Arg Tyr Ala Asp Leu Leu Phe
1               5                   10                  15
```

```
Pro Thr Thr Leu Ala Trp
            20

<210> SEQ ID NO 88
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 89
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Cys Glu Glu Gln Asn Pro Trp Ala Arg Tyr Ala Glu Leu Leu Phe
1               5                   10                  15

Pro Thr Thr Leu Ala Trp
            20

<210> SEQ ID NO 90
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Cys Glu Glu Gln Asn Pro Trp Ala Arg Tyr Ala Glu Trp Leu Phe
1               5                   10                  15

Pro Thr Thr Leu Leu Leu Leu Glu
            20

<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Cys Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 92
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 92

Ala Cys Glu Glu Gln Asn Pro Gln Ala Glu Tyr Ala Glu Trp Leu Phe
1               5                   10                  15

Pro Thr Thr Leu Leu Leu Leu Glu
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 93

Trp Ala Arg Tyr Ala Asp Trp Leu Phe Thr Thr Pro Leu Leu Leu Leu
1               5                   10                  15

Asp Leu Ala Leu Leu
            20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 94

Tyr Ala Arg Tyr Ala Asp Trp Leu Phe Thr Thr Pro Leu Leu Leu Leu
1               5                   10                  15

Asp Leu Ala Leu Leu
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 95

Trp Ala Arg Tyr Ser Asp Trp Leu Phe Thr Thr Pro Leu Leu Leu Tyr
1               5                   10                  15

Asp Leu Gly Leu Leu
            20

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
```

-continued description of substitutions and preferred embodiments

<400> SEQUENCE: 96

Trp Ala Arg Tyr Thr Asp Trp Phe Thr Thr Pro Leu Leu Leu Tyr Asp
1               5                   10                  15

Leu Ala Leu Leu Ala
            20

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 97

Trp Ala Arg Tyr Thr Asp Trp Leu Phe Thr Thr Pro Leu Leu Leu Tyr
1               5                   10                  15

Asp Leu Gly Leu Leu
            20

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 98

Trp Ala Arg Tyr Ala Asp Trp Leu Phe Thr Thr Pro Leu Leu Leu Leu
1               5                   10                  15

Asp Leu Ser Leu Leu
            20

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 99

Leu Leu Ala Leu Asp Leu Leu Leu Leu Pro Thr Thr Phe Leu Trp Asp
1               5                   10                  15

Ala Tyr Arg Ala Trp
            20

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: See specification as filed for detailed
      description of substitutions and preferred embodiments

<400> SEQUENCE: 100

Leu Leu Ala Leu Asp Leu Leu Leu Pro Thr Thr Phe Leu Trp Asp
1               5                   10                  15

Ala Tyr Arg Ala Tyr
            20

<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 101

Leu Leu Gly Leu Asp Tyr Leu Leu Leu Pro Thr Thr Phe Leu Trp Asp
1               5                   10                  15

Ser Tyr Arg Ala Trp
            20

<210> SEQ ID NO 102
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 102

Ala Leu Leu Ala Leu Asp Tyr Leu Leu Leu Pro Thr Thr Phe Trp Asp
1               5                   10                  15

Thr Tyr Arg Ala Trp
            20

<210> SEQ ID NO 103
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 103

Leu Leu Gly Leu Asp Tyr Leu Leu Leu Pro Thr Thr Phe Leu Trp Asp
1               5                   10                  15

Thr Tyr Arg Ala Trp
            20

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: See specification as filed for detailed
      description of substitutions and preferred embodiments

<400> SEQUENCE: 104

Leu Leu Ser Leu Asp Leu Leu Leu Leu Pro Thr Thr Phe Leu Trp Asp
1               5                   10                  15

Ala Tyr Arg Ala Trp
            20

<210> SEQ ID NO 105
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 105

Gly Leu Ala Gly Leu Leu Gly Leu Glu Gly Leu Leu Gly Leu Pro Leu
1               5                   10                  15

Gly Leu Leu Glu Gly Leu Trp Leu Gly Leu
            20                  25

<210> SEQ ID NO 106
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 106

Leu Gly Leu Trp Leu Gly Glu Leu Leu Gly Leu Pro Leu Gly Leu Leu
1               5                   10                  15

Gly Glu Leu Gly Leu Leu Gly Ala Leu Gly
            20                  25

<210> SEQ ID NO 107
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 107

Trp Arg Ala Tyr Leu Asp Leu Leu Phe Pro Thr Asp Thr Leu Leu Leu
1               5                   10                  15

Asp Leu Leu Trp
            20

<210> SEQ ID NO 108
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: See specification as filed for detailed
      description of substitutions and preferred embodiments

<400> SEQUENCE: 108

Trp Leu Leu Asp Leu Leu Leu Thr Asp Thr Pro Phe Leu Leu Asp Leu
1               5                   10                  15

Tyr Ala Arg Trp
            20

<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 109

Trp Ala Arg Tyr Leu Glu Trp Leu Phe Pro Thr Glu Thr Leu Leu Leu
1               5                   10                  15

Glu Leu

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 110

Trp Ala Gln Tyr Leu Glu Leu Leu Phe Pro Thr Glu Thr Leu Leu Leu
1               5                   10                  15

Glu Trp

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 111

Leu Glu Leu Leu Leu Thr Glu Thr Pro Phe Leu Trp Glu Leu Tyr Arg
1               5                   10                  15

Ala Trp

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:

-continued

<223> OTHER INFORMATION: See specification as filed for detailed
      description of substitutions and preferred embodiments

<400> SEQUENCE: 112

Trp Glu Leu Leu Leu Thr Glu Thr Pro Phe Leu Leu Glu Leu Tyr Gln
1               5                   10                  15

Ala Trp

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 113

Trp Leu Phe Thr Thr Pro Leu Leu Leu Leu Asn Gly Ala Leu Leu Val
1               5                   10                  15

Glu

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 114

Trp Leu Phe Thr Thr Pro Leu Leu Leu Leu Pro Gly Ala Leu Leu Val
1               5                   10                  15

Glu

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 115

Trp Ala Arg Tyr Ala Asp Leu Leu Phe Pro Thr Thr Leu Ala Trp
1               5                   10                  15

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 116

Glu Val Leu Leu Ala Gly Asn Leu Leu Leu Pro Thr Thr Phe Leu
1               5                   10                  15

Trp

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 117

Glu Val Leu Leu Ala Gly Pro Leu Leu Leu Pro Thr Thr Phe Leu
1               5                   10                  15

Trp

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 118

Trp Ala Leu Thr Thr Pro Phe Leu Leu Asp Ala Tyr Arg Ala Trp
1               5                   10                  15

<210> SEQ ID NO 119
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 119

Asn Leu Glu Gly Phe Phe Ala Thr Leu Gly Gly Glu Ile Ala Leu Trp
1               5                   10                  15

Ser Leu Val Val Leu Ala Ile Glu
            20

<210> SEQ ID NO 120
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 120

Glu Gly Phe Phe Ala Thr Leu Gly Gly Glu Ile Ala Leu Trp Ser Asp
1               5                   10                  15

Val Val Leu Ala Ile Glu

```
                           20

<210> SEQ ID NO 121
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 121

Glu Gly Phe Phe Ala Thr Leu Gly Gly Glu Ile Pro Leu Trp Ser Asp
1               5                   10                  15

Val Val Leu Ala Ile Glu
            20

<210> SEQ ID NO 122
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 122

Glu Ile Ala Leu Val Val Leu Ser Trp Leu Ala Ile Glu Gly Gly Leu
1               5                   10                  15

Thr Ala Phe Phe Gly Glu Leu Asn
            20

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 123

Glu Ile Ala Leu Val Val Asp Ser Trp Leu Ala Ile Glu Gly Gly Leu
1               5                   10                  15

Thr Ala Phe Phe Gly Glu
            20

<210> SEQ ID NO 124
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 124

Glu Ile Ala Leu Val Val Asp Ser Trp Leu Pro Ile Glu Gly Gly Leu
1               5                   10                  15
```

Thr Ala Phe Phe Gly Glu
            20

<210> SEQ ID NO 125
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 125

Ile Leu Asp Leu Val Phe Gly Leu Leu Phe Ala Val Thr Ser Val Asp
1               5                   10                  15

Phe Leu Val Gln Trp
            20

<210> SEQ ID NO 126
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 126

Trp Gln Val Leu Phe Asp Val Ser Thr Val Ala Phe Leu Leu Gly Phe
1               5                   10                  15

Val Leu Asp Leu Ile
            20

<210> SEQ ID NO 127
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 128
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ala Glu Gln Asn Pro Ile Tyr Trp Ala Arg Tyr Ala Glu Trp Leu Phe
1               5                   10                  15

Thr Thr Pro Leu Leu Leu Leu Glu Leu Ala Leu Leu Val Glu Ala Glu
            20                  25                  30

Glu Thr

```
<210> SEQ ID NO 129
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129
```

Ala Asp Asp Gln Asn Pro Trp Arg Ala Tyr Leu Asp Leu Leu Phe Pro
1               5                   10                  15

Asp Thr Thr Asp Leu Leu Leu Leu Asp Leu Leu Trp Asp Ala Asp Glu
            20                  25                  30

Thr

```
<210> SEQ ID NO 130
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130
```

Ala Glu Glu Gln Asn Pro Trp Arg Ala Tyr Leu Glu Leu Leu Phe Pro
1               5                   10                  15

Glu Thr Thr Glu Leu Leu Leu Leu Glu Leu Leu Trp Glu Ala Glu Glu
            20                  25                  30

Thr

```
<210> SEQ ID NO 131
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gla

<400> SEQUENCE: 131
```

Ala Glu Gln Asn Pro Ile Tyr Trp Ala Arg Tyr Ala Xaa Trp Leu Phe
1               5                   10                  15

Thr Thr Pro Leu Leu Leu Leu Asp Leu Ala Leu Leu Val Asp Ala Asp
            20                  25                  30

Glu Thr

```
<210> SEQ ID NO 132
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Gla

<400> SEQUENCE: 132
```

Ala Glu Gln Asn Pro Ile Tyr Trp Ala Arg Tyr Ala Asp Trp Leu Phe

```
                   1               5                  10                  15
Thr Thr Pro Leu Leu Leu Leu Xaa Leu Ala Leu Leu Val Asp Ala Asp
            20                  25                  30

Glu Thr

<210> SEQ ID NO 133
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gla
<220> FEATURE:
<221> NAME/KEY: MOD_RES
<222> LOCATION: (24)..(24)
<223> OTHER INFORMATION: Gla

<400> SEQUENCE: 133

Ala Glu Gln Asn Pro Ile Tyr Trp Ala Arg Tyr Ala Xaa Trp Leu Phe
1               5                  10                  15

Thr Thr Pro Leu Leu Leu Leu Xaa Leu Ala Leu Leu Val Asp Ala Asp
            20                  25                  30

Glu Thr

<210> SEQ ID NO 134
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Aad

<400> SEQUENCE: 134

Ala Glu Gln Asn Pro Ile Tyr Trp Ala Arg Tyr Ala Xaa Trp Leu Phe
1               5                  10                  15

Thr Thr Pro Leu Leu Leu Leu Asp Leu Ala Leu Leu Val Asp Ala Asp
            20                  25                  30

Glu Thr

<210> SEQ ID NO 135
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Aad

<400> SEQUENCE: 135

Ala Glu Gln Asn Pro Ile Tyr Trp Ala Arg Tyr Ala Asp Trp Leu Phe
1               5                  10                  15

Thr Thr Pro Leu Leu Leu Leu Xaa Leu Ala Leu Leu Val Asp Ala Asp
            20                  25                  30

Glu Thr
```

```
<210> SEQ ID NO 136
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Aad
<220> FEATURE:
<221> NAME/KEY: MOD_RES
<222> LOCATION: (24)..(24)
<223> OTHER INFORMATION: Aad

<400> SEQUENCE: 136

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 137
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gla
<220> FEATURE:
<221> NAME/KEY: MOD_RES
<222> LOCATION: (24)..(24)
<223> OTHER INFORMATION: Aad

<400> SEQUENCE: 137

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 138
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Aad
<220> FEATURE:
<221> NAME/KEY: MOD_RES
<222> LOCATION: (24)..(24)
<223> OTHER INFORMATION: Gla

<400> SEQUENCE: 138

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30
```

Glu Thr

<210> SEQ ID NO 139
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 140
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 141
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 142
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

```
Glu Gly Thr
        35

<210> SEQ ID NO 143
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ala Glu Gln Asn Pro Ile Tyr Trp Ala Arg Tyr Ala Asn Trp Leu Phe
1               5                   10                  15

Thr Thr Pro Leu Leu Leu Leu Asn Leu Ala Leu Leu Val Asp Ala Asp
            20                  25                  30

Glu Gly Thr
        35

<210> SEQ ID NO 144
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ala Glu Gln Asn Pro Ile Tyr Trp Ala Arg Tyr Ala Lys Trp Leu Phe
1               5                   10                  15

Thr Thr Pro Leu Leu Leu Leu Lys Leu Ala Leu Leu Val Asp Ala Asp
            20                  25                  30

Glu Gly Thr
        35

<210> SEQ ID NO 145
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 146
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
```

-continued

```
               20                  25                  30

Asp Glu Gly Thr
        35

<210> SEQ ID NO 147
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Ala Ala Glu Gln Asn Pro Ile Tyr Trp Ala Arg Tyr Ala Ala Trp Leu
1               5                   10                  15

Phe Thr Thr Pro Leu Leu Leu Asp Leu Ala Leu Leu Val Asp Ala
            20                  25                  30

Asp Glu Gly Thr
        35

<210> SEQ ID NO 148
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ala Ala Glu Gln Asn Pro Ile Tyr Trp Ala Arg Tyr Ala Asp Trp Leu
1               5                   10                  15

Phe Thr Thr Ala Leu Leu Leu Asp Leu Ala Leu Leu Val Asp Ala
            20                  25                  30

Asp Glu Gly Thr
        35

<210> SEQ ID NO 149
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Ala Ala Glu Gln Asn Pro Ile Tyr Trp Ala Arg Tyr Ala Asp Trp Leu
1               5                   10                  15

Phe Thr Thr Pro Leu Leu Leu Glu Leu Ala Leu Leu Val Asp Ala
            20                  25                  30

Asp Glu Gly Thr
        35

<210> SEQ ID NO 150
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ala Ala Glu Gln Asn Pro Ile Tyr Trp Ala Arg Tyr Ala Glu Trp Leu
1               5                   10                  15
```

```
Phe Thr Thr Pro Leu Leu Leu Leu Asp Leu Ala Leu Leu Val Asp Ala
                20                  25                  30

Asp Glu Gly Thr
        35

<210> SEQ ID NO 151
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ala Ala Glu Gln Asn Pro Ile Ile Tyr Trp Ala Arg Tyr Ala Asp Trp
1               5                   10                  15

Leu Phe Thr Asp Leu Pro Leu Leu Leu Asp Leu Leu Ala Leu Leu
                20                  25                  30

Val Asp Ala Asp Glu Gly Thr
        35

<210> SEQ ID NO 152
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gly Glu Gln Asn Pro Ile Tyr Trp Ala Gln Tyr Ala Asp Trp Leu Phe
1               5                   10                  15

Thr Thr Pro Leu Leu Leu Leu Asp Leu Ala Leu Leu Val Asp Ala Asp
                20                  25                  30

Glu Gly

<210> SEQ ID NO 153
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
                20                  25                  30

Asp Glu Gly
        35

<210> SEQ ID NO 154
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gly Gly Glu Gln Asn Pro Ile Tyr Trp Ala Arg Tyr Ala Asp Trp Leu
1               5                   10                  15
```

```
Phe Thr Thr Pro Leu Leu Leu Leu Asp Ala Leu Leu Val Asp Ala
            20                  25                  30

Asp Glu Gly
        35

<210> SEQ ID NO 155
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 156
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gly Gly Glu Gln Asn Pro Ile Tyr Trp Ala Arg Tyr Ala Trp Asp Leu
1               5                   10                  15

Phe Thr Thr Pro Leu Leu Leu Leu Asp Leu Ala Leu Leu Val Asp Ala
            20                  25                  30

Asp Glu Gly
        35

<210> SEQ ID NO 157
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ala Ala Glu Gln Asn Pro Ile Tyr Trp Ala Arg Tyr Ala Asp Trp Leu
1               5                   10                  15

Phe Thr Thr Gly Leu Leu Leu Leu Asp Leu Ala Leu Leu Val Asp Ala
            20                  25                  30

Asp Glu Gly Thr
        35

<210> SEQ ID NO 158
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Asp Asp Asp Glu Asp Asn Pro Ile Tyr Trp Ala Arg Tyr Ala Asp Trp
1               5                   10                  15
```

Leu Phe Thr Thr Pro Leu Leu Leu Leu His Gly Ala Leu Leu Val Asp
            20                  25                  30

Ala Asp

<210> SEQ ID NO 159
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu
        35

<210> SEQ ID NO 160
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Cys Glu Gln Asn Pro Ile Tyr Trp Ala Arg Tyr Ala Asp Trp His Phe
1               5                   10                  15

Thr Thr Pro Leu Leu Leu Leu Asp Leu Ala Leu Leu Val Asp Ala Asp
            20                  25                  30

Glu

<210> SEQ ID NO 161
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 162
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp

```
            20                  25                  30

Glu

<210> SEQ ID NO 163
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 164
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Ala Asp Asn Asn Pro Trp Ile Tyr Ala Arg Tyr Ala Asp Leu Thr Thr
1               5                   10                  15

Phe Pro Leu Leu Leu Leu Asp Leu Ala Leu Leu Val Asp Phe Asp Asp
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Ala Asp Asn Asn Pro Phe Ile Tyr Ala Arg Tyr Ala Asp Leu Thr Thr
1               5                   10                  15

Trp Pro Leu Leu Leu Leu Asp Leu Ala Leu Leu Val Asp Phe Asp Asp
            20                  25                  30

<210> SEQ ID NO 166
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Ala Asp Asn Asn Pro Phe Ile Tyr Ala Arg Tyr Ala Asp Leu Thr Thr
1               5                   10                  15

Phe Pro Leu Leu Leu Leu Asp Leu Ala Leu Leu Val Asp Trp Asp Asp
            20                  25                  30

<210> SEQ ID NO 167
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 167

Ala Asp Asn Asn Pro Phe Pro Tyr Ala Arg Tyr Ala Asp Leu Thr Thr
1               5                   10                  15

Trp Ile Leu Leu Leu Leu Asp Leu Ala Leu Leu Val Asp Phe Asp Asp
                20                  25                  30

<210> SEQ ID NO 168
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Ala Asp Asn Asn Pro Phe Ile Tyr Ala Tyr Arg Ala Asp Leu Thr Thr
1               5                   10                  15

Phe Pro Leu Leu Leu Leu Asp Leu Ala Leu Leu Val Asp Trp Asp Asp
                20                  25                  30

<210> SEQ ID NO 169
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Ala Asp Asn Asn Pro Phe Ile Tyr Ala Thr Tyr Ala Asp Leu Arg Thr
1               5                   10                  15

Phe Pro Leu Leu Leu Leu Asp Leu Ala Leu Leu Val Asp Trp Asp Asp
                20                  25                  30

<210> SEQ ID NO 170
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Thr Glu Asp Ala Asp Val Leu Leu Ala Leu Asp Leu Leu Leu Leu Pro
1               5                   10                  15

Thr Thr Phe Leu Trp Asp Ala Tyr Arg Ala Trp Tyr Pro Asn Gln Glu
                20                  25                  30

Ala

<210> SEQ ID NO 171
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Ala Glu Asp Gln Asn Pro Tyr Trp Ala Arg Tyr Ala Asp Trp Leu Phe
1               5                   10                  15
```

Thr Thr Pro Leu Leu Leu Leu Asp Leu Ala Leu Leu Val Asp
            20                  25                  30

<210> SEQ ID NO 172
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu
            20                  25                  30

<210> SEQ ID NO 173
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Glu Asp Gln Asn Pro Tyr Trp Arg Ala Tyr Ala Asp Leu Phe Thr
1               5                   10                  15

Pro Leu Thr Leu Leu Asp Leu Leu Ala Leu Trp Asp
            20                  25

<210> SEQ ID NO 174
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp
            20                  25

<210> SEQ ID NO 175
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Asp Ala Asp Glu
            20                  25                  30

<210> SEQ ID NO 176
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (12)..(12)
<223> OTHER INFORMATION: Gla

<400> SEQUENCE: 176

Ala Asp Asp Gln Asn Pro Trp Arg Ala Tyr Leu Xaa Leu Leu Phe Pro
1               5                   10                  15

Thr Asp Thr Leu Leu Leu Asp Leu Leu Trp
            20                  25

<210> SEQ ID NO 177
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Gla

<400> SEQUENCE: 177

Ala Asp Asp Gln Asn Pro Trp Arg Ala Tyr Leu Asp Leu Leu Phe Pro
1               5                   10                  15

Thr Xaa Thr Leu Leu Leu Asp Leu Leu Trp
            20                  25

<210> SEQ ID NO 178
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Gla

<400> SEQUENCE: 178

Ala Asp Asp Gln Asn Pro Trp Arg Ala Tyr Leu Asp Leu Leu Phe Pro
1               5                   10                  15

Thr Asp Thr Leu Leu Leu Xaa Leu Leu Trp
            20                  25

<210> SEQ ID NO 179
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Gla

<400> SEQUENCE: 179

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25
```

```
<210> SEQ ID NO 180
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (23)..(23)
<223> OTHER INFORMATION: Gla

<400> SEQUENCE: 180

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 181
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Gla
<220> FEATURE:
<221> NAME/KEY: MOD_RES
<222> LOCATION: (23)..(23)
<223> OTHER INFORMATION: Gla

<400> SEQUENCE: 181

Ala Asp Asp Gln Asn Pro Trp Arg Ala Tyr Leu Asp Leu Leu Phe Pro
1               5                   10                  15

Thr Xaa Thr Leu Leu Leu Xaa Leu Leu Trp
            20                  25

<210> SEQ ID NO 182
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Gla
<220> FEATURE:
<221> NAME/KEY: MOD_RES
<222> LOCATION: (23)..(23)
<223> OTHER INFORMATION: Gla

<400> SEQUENCE: 182

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25
```

```
<210> SEQ ID NO 183
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad

<400> SEQUENCE: 183

Ala Asp Asp Gln Asn Pro Trp Arg Ala Tyr Leu Xaa Leu Leu Phe Pro
1               5                   10                  15

Thr Asp Thr Leu Leu Leu Asp Leu Leu Trp
            20                  25

<210> SEQ ID NO 184
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Aad

<400> SEQUENCE: 184

Ala Asp Asp Gln Asn Pro Trp Arg Ala Tyr Leu Asp Leu Leu Phe Pro
1               5                   10                  15

Thr Xaa Thr Leu Leu Leu Asp Leu Leu Trp
            20                  25

<210> SEQ ID NO 185
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aad

<400> SEQUENCE: 185

Ala Asp Asp Gln Asn Pro Trp Arg Ala Tyr Leu Asp Leu Leu Phe Pro
1               5                   10                  15

Thr Asp Thr Leu Leu Leu Xaa Leu Leu Trp
            20                  25

<210> SEQ ID NO 186
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (18)..(18)
```

<223> OTHER INFORMATION: Aad

<400> SEQUENCE: 186

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 187
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (23)..(23)
<223> OTHER INFORMATION: Aad

<400> SEQUENCE: 187

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 188
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)
<223> OTHER INFORMATION: Aad

<400> SEQUENCE: 188

Ala Asp Asp Gln Asn Pro Trp Arg Ala Tyr Leu Asp Leu Leu Phe Pro
1               5                   10                  15

Thr Xaa Thr Leu Leu Leu Xaa Leu Leu Trp
            20                  25

<210> SEQ ID NO 189
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)

<223> OTHER INFORMATION: Aad

<400> SEQUENCE: 189

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 190
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Aad

<400> SEQUENCE: 190

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 191
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (23)..(23)
<223> OTHER INFORMATION: Aad

<400> SEQUENCE: 191

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 192
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Gla
<220> FEATURE:
<221> NAME/KEY: MOD_RES
<222> LOCATION: (23)..(23)

<223> OTHER INFORMATION: Aad

<400> SEQUENCE: 192

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 193
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (18)..(18)
<223> OTHER INFORMATION: Gla

<400> SEQUENCE: 193

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 194
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (23)..(23)
<223> OTHER INFORMATION: Gla

<400> SEQUENCE: 194

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 195
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)

<223> OTHER INFORMATION: Gla

<400> SEQUENCE: 195

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 196
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Glu Glu Gln Asn Pro Trp Leu Gly Ala Tyr Leu Asp Leu Leu Phe
1               5                   10                  15

Pro Leu Glu Leu Leu Gly Leu Leu Glu Leu Gly Leu Trp
            20                  25

<210> SEQ ID NO 197
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ala Asp Asp Asp Asp Asp Asp Pro Trp Gln Ala Tyr Leu Asp Leu Leu
1               5                   10                  15

Phe Pro Thr Asp Thr Leu Leu Leu Asp Leu Leu Trp
            20                  25

<210> SEQ ID NO 198
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Glu Glu Gln Asn Pro Trp Arg Ala Tyr Leu Glu Leu Leu Phe Pro
1               5                   10                  15

Thr Glu Thr Leu Leu Leu Glu Leu Leu Trp
            20                  25

<210> SEQ ID NO 199
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Asp Asp Gln Asn Pro Trp Ala Arg Tyr Leu Asp Trp Leu Phe Pro
1               5                   10                  15

Thr Asp Thr Leu Leu Leu Asp Leu
            20

-continued

```
<210> SEQ ID NO 200
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asp Asn Asn Asn Pro Trp Arg Ala Tyr Leu Asp Leu Leu Phe Pro Thr
1               5                   10                  15

Asp Thr Leu Leu Leu Asp Trp
            20

<210> SEQ ID NO 201
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Glu Glu Gln Asn Pro Trp Ala Arg Tyr Leu Glu Trp Leu Phe Pro
1               5                   10                  15

Thr Glu Thr Leu Leu Leu Glu Leu
            20

<210> SEQ ID NO 202
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asp Asp Asp Asp Asp Asp Pro Trp Gln Ala Tyr Leu Asp Leu Phe Pro
1               5                   10                  15

Thr Asp Thr Leu Ala Leu Asp Leu Trp
            20                  25

<210> SEQ ID NO 203
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Glu Glu Gln Gln Pro Trp Ala Gln Tyr Leu Glu Leu Leu Phe Pro Thr
1               5                   10                  15

Glu Thr Leu Leu Leu Glu Trp
            20

<210> SEQ ID NO 204
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Glu Glu Gln Gln Pro Trp Arg Ala Tyr Leu Glu Leu Leu Phe Pro Thr
```

Glu Thr Leu Leu Leu Glu Trp
            20

<210> SEQ ID NO 205
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Glu Asp Gln Asn Pro Trp Ala Arg Tyr Ala Asp Trp Leu Phe Pro
1               5                   10                  15

Thr Thr Leu Leu Leu Leu Asp
            20

<210> SEQ ID NO 206
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ala Glu Glu Gln Asn Pro Trp Ala Arg Tyr Ala Glu Trp Leu Phe Pro
1               5                   10                  15

Thr Thr Leu Leu Leu Leu Glu
            20

<210> SEQ ID NO 207
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ala Glu Asp Gln Asn Pro Trp Ala Arg Tyr Ala Asp Leu Leu Phe Pro
1               5                   10                  15

Thr Thr Leu Ala Trp
            20

<210> SEQ ID NO 208
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala Glu Glu Gln Asn Pro Trp Ala Arg Tyr Ala Glu Leu Leu Phe Pro
1               5                   10                  15

Thr Thr Leu Ala Trp
            20

<210> SEQ ID NO 209
<211> LENGTH: 36
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 209

Asp Asp Asp Asp Asp Asn Pro Asn Tyr Trp Ala Arg Tyr Ala Asn Trp
1               5                   10                  15

Leu Phe Thr Thr Pro Leu Leu Leu Asn Gly Ala Leu Leu Val Glu
            20                  25                  30

Ala Glu Glu Thr
        35

<210> SEQ ID NO 210
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Asp Asp Asp Asp Asp Asn Pro Asn Tyr Trp Ala Arg Tyr Ala Pro Trp
1               5                   10                  15

Leu Phe Thr Thr Pro Leu Leu Leu Pro Gly Ala Leu Leu Val Glu
            20                  25                  30

Ala Glu Glu Thr
        35

<210> SEQ ID NO 211
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 212
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 213
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 213

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 214
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 215
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 216
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Glu Gln Asn Pro Ile Tyr Trp Ala Arg Tyr Ala Asp Leu Leu Phe
1               5                   10                  15

Pro Thr Thr Leu Ala Trp
            20

<210> SEQ ID NO 217
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Glu Gln Asn Pro Ile Tyr Phe Ala Arg Tyr Ala Asp Trp Leu Phe
1               5                   10                  15

Thr Thr Pro Leu
            20

```
<210> SEQ ID NO 218
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Glu Asp Gln Asn Pro Trp Ala Arg Tyr Ala Asp Leu Leu Phe Pro Thr
1               5                   10                  15

Thr Leu Ala Trp
            20

<210> SEQ ID NO 219
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gly Leu Ala Gly Leu Ala Gly Leu Leu Gly Leu Glu Gly Leu Leu Gly
1               5                   10                  15

Leu Pro Leu Gly Leu Leu Glu Gly Leu Trp Leu Gly Leu Glu Leu Glu
            20                  25                  30

Gly Asn

<210> SEQ ID NO 220
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Glu Gln Asn Pro Ile Tyr Ile Leu Asp Leu Val Phe Gly Leu Leu Phe
1               5                   10                  15

Ala Val Thr Ser Val Asp Phe Leu Val Gln Trp Asp Asp Ala Gly Asp
            20                  25                  30

<210> SEQ ID NO 221
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asn Leu Glu Gly Phe Phe Ala Thr Leu Gly Gly Glu Ile Ala Leu Trp
1               5                   10                  15

Ser Leu Val Val Leu Ala Ile Glu
            20

<210> SEQ ID NO 222
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222
```

```
Asn Asn Glu Gly Phe Phe Ala Thr Leu Gly Gly Glu Ile Ala Leu Trp
1               5                   10                  15

Ser Asp Val Val Leu Ala Ile Glu
            20

<210> SEQ ID NO 223
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Asp Asn Asn Glu Gly Phe Phe Ala Thr Leu Gly Gly Glu Ile Pro Leu
1               5                   10                  15

Trp Ser Asp Val Val Leu Ala Ile Glu
            20                  25
```